US006395955B1

(12) United States Patent
Roe et al.

(10) Patent No.: US 6,395,955 B1
(45) Date of Patent: *May 28, 2002

(54) DIAPER INCLUDING FECES MODIFICATION AGENT

(75) Inventors: Donald C. Roe, West Chester; Nicholas A. Ahr, Cincinnati, both of OH (US); Christopher P. Bewick-Sonntag, Pescara (IT); Mattias Schmidt, Idstein (DE); Stephen A. Goldman, Pescara (IT); John Christison, Mississauga (CA); David Joseph Kenneth Goulait, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/342,395

(22) Filed: Jun. 29, 1999

Related U.S. Application Data

(63) Continuation-in-part of application No. 09/107,561, filed on Jun. 29, 1998, now Pat. No. 6,149,636, and a continuation-in-part of application No. 09/106,225, filed on Jun. 29, 1998, now Pat. No. 6,186,991
(60) Provisional application No. 60/091,076, filed on Jun. 29, 1998, and provisional application No. 60/090,993, filed on Jun. 29, 1998.

(51) Int. Cl.[7] ............................................. A61F 13/15
(52) U.S. Cl. ..................... 604/361; 604/362; 604/375; 604/385.19
(58) Field of Search ................................. 604/361, 364, 604/367, 368, 385.01, 385.101, 385.12, 375, 385.19

(56) References Cited

U.S. PATENT DOCUMENTS

| 2,127,538 A | 8/1938 | Seiger | 128/238 |
|---|---|---|---|
| 2,681,032 A | 6/1954 | Shaw | 116/114 |
| 2,926,667 A | 3/1960 | Burger et al. | 128/285 |
| 3,490,454 A | 1/1970 | Goldfarb et al. | 128/285 |
| 3,814,101 A | 6/1974 | Kozak | 128/287 |
| 3,881,491 A | 5/1975 | Whyte | 128/287 |
| 3,903,232 A | * 9/1975 | Wood et al. | 264/157 |
| 3,921,232 A | 11/1975 | Whyte | 5/91 |
| 3,935,363 A | * 1/1976 | Burkholder et al. | 428/281 |
| 3,987,792 A | 10/1976 | Hernandez et al. | 128/284 |
| 4,022,211 A | * 5/1977 | Timmons et al. | 128/287 |
| 4,246,900 A | 1/1981 | Schröder | 128/287 |
| 4,315,761 A | * 2/1982 | Larrson et al. | 71/21 |
| 4,356,818 A | * 11/1982 | Macias et al. | 128/138 |
| 4,401,712 A | 8/1983 | Morrison | 428/289 |
| 4,636,474 A | 1/1987 | Ogura et al. | 435/291 |
| 4,657,537 A | 4/1987 | Zimmerer | 604/360 |
| 4,681,577 A | 7/1987 | Stern et al. | 604/378 |
| 4,705,050 A | 11/1987 | Markham | 128/749 |
| 4,732,930 A | 3/1988 | Tanaka et al. | 524/742 |
| 4,747,166 A | 5/1988 | Kuntz | 4/144.1 |
| 4,753,643 A | * 6/1988 | Kassai | 604/359 |

(List continued on next page.)

FOREIGN PATENT DOCUMENTS

| EP | 0 612 520 A2 | 8/1994 | A61K/9/52 |
|---|---|---|---|
| EP | 0 804 912 | 11/1997 | A61F/13/15 |
| EP | 0 804 913 | 11/1997 | A61F/13/15 |

(List continued on next page.)

Primary Examiner—John G. Weiss
Assistant Examiner—Jamisue A Webb
(74) Attorney, Agent, or Firm—Michael P. Hayden; David M. Weirich; Ken K. Patel

(57) ABSTRACT

An article to be fitted to a wearer including an agent which is available in an effective concentration to physically or chemically modify some or all of the fecal material or other bodily exudates deposited in the article. The modification of the feces may improve acceptance and/or retention of the exudates within the article to reduce the spreading of fecal material within the diaper and/or to reduce the tendency of the fecal material to adhere to the wearer's skin.

43 Claims, 19 Drawing Sheets

U.S. PATENT DOCUMENTS

| | | | |
|---|---|---|---|
| 4,753,645 A | 6/1988 | Johnson | 604/378 |
| 4,754,264 A | 6/1988 | Okada et al. | 340/573 |
| 4,776,331 A | 10/1988 | Simjian | 128/169 |
| 4,778,459 A | 10/1988 | Fuisz | 604/378 |
| 4,787,896 A | 11/1988 | Houghton et al. | 604/385.1 |
| 4,790,836 A | 12/1988 | Brecher | 604/359 |
| 4,796,014 A | 1/1989 | Chia | 340/573 |
| 4,834,733 A | 5/1989 | Huntoon et al. | 604/361 |
| 4,842,593 A | 6/1989 | Jordan et al. | 604/360 |
| 4,981,465 A | 1/1991 | Ballan et al. | 600/32 |
| 5,002,541 A | 3/1991 | Conkling et al. | 604/319 |
| 5,100,933 A | 3/1992 | Tanaka et al. | 523/300 |
| 5,118,607 A | 6/1992 | Bignami et al. | 435/7.1 |
| 5,181,905 A | 1/1993 | Flam | 602/41 |
| 5,264,830 A | 11/1993 | Kline et al. | 340/604 |
| 5,330,459 A | 7/1994 | Lavon et al. | 604/385.1 |
| 5,341,127 A | 8/1994 | Smith | 340/604 |
| 5,342,343 A | 8/1994 | Kitaoka et al. | 604/385.2 |
| 5,409,771 A * | 4/1995 | Dahmen et al. | 428/327 |
| 5,416,469 A | 5/1995 | Colling | 340/573 |
| 5,468,236 A | 11/1995 | Everhart et al. | 604/361 |
| 5,520,674 A | 5/1996 | Lavon et al. | 604/385.1 |
| 5,558,655 A | 9/1996 | Jezzi et al. | 604/378 |
| 5,568,128 A | 10/1996 | Nair | 340/604 |
| 5,582,604 A | 12/1996 | Ahr et al. | 604/385.1 |
| 5,599,916 A * | 2/1997 | Dutkiewicz et al. | 536/20 |
| 5,607,417 A | 3/1997 | Batich et al. | 604/890.1 |
| 5,612,411 A * | 3/1997 | Gross | 525/54.3 |
| 5,641,562 A | 6/1997 | Larson et al. | 442/394 |
| 5,643,241 A | 7/1997 | Ahr et al. | 604/385.1 |
| 5,649,914 A | 7/1997 | Glaug et al. | 604/361 |
| 5,653,862 A | 8/1997 | Parris | 205/777.5 |
| 5,658,268 A | 8/1997 | Johns et al. | 604/361 |
| 5,678,564 A | 10/1997 | Lawrence et al. | 128/761 |
| 5,681,298 A | 10/1997 | Brunner et al. | 604/361 |
| 5,702,376 A | 12/1997 | Glaug et al. | 604/361 |
| 5,728,125 A | 3/1998 | Salinas | 604/361 |
| 5,733,272 A | 3/1998 | Brunner et al. | 604/359 |
| 5,736,590 A | 4/1998 | Rasmussen | 523/113 |
| 5,760,694 A * | 6/1998 | Nissim et al. | 340/604 |
| 5,769,834 A | 6/1998 | Reiter et al. | 604/385.1 |
| 5,797,892 A | 8/1998 | Glaug et al. | 604/361 |
| 5,801,220 A * | 9/1998 | Desai et al. | 524/13 |
| 5,876,393 A | 3/1999 | Ahr et al. | 604/387 |
| 5,957,907 A * | 9/1999 | Sauer | 604/385.2 |
| 5,977,430 A * | 11/1999 | Roe et al. | 604/378 |
| 5,998,695 A * | 12/1999 | Roe et al. | 604/367 |
| 6,018,093 A * | 1/2000 | Roe et al. | 604/367 |
| 6,093,869 A * | 7/2000 | Roe et al. | 604/361 |
| 6,160,198 A * | 12/2000 | Roe et al. | 604/361 |

FOREIGN PATENT DOCUMENTS

| | | | |
|---|---|---|---|
| EP | 0 804 914 A1 | 11/1997 | A61F/13/15 |
| EP | 0 804 915 | 11/1997 | A61F/13/15 |
| EP | 0 804 916 | 11/1997 | A61F/13/15 |
| EP | 0 804 917 | 11/1997 | A61F/13/15 |
| EP | 0 806 194 | 11/1997 | A61F/13/15 |
| EP | 0 806 195 | 11/1997 | A61F/13/15 |
| EP | 0 815 818 A1 | 1/1998 | A61F/13/15 |
| EP | 0 815 821 A2 | 1/1998 | A61F/13/15 |
| JP | 59106501 | 6/1984 | |
| JP | 10-62369 | 3/1998 | G01N/27/00 |
| JP | 11004852 | 1/1999 | |
| WO | WO 92/02005 A | 2/1992 | G08F/8/00 |
| WO | WO 95/00089 | 1/1995 | A61F/13/15 |
| WO | WO 95/00090 | 1/1995 | A61F/13/15 |
| WO | WO 95/32697 | 12/1995 | A61F/13/15 |
| WO | WO 95/32698 | 12/1995 | A61F/13/15 |
| WO | WO 97/16149 | 5/1997 | A61F/13/42 |
| WO | WO 97/24150 | 7/1997 | A61L/15/62 |
| WO | WO 97/42613 | 11/1997 | G08B/21/100 |
| WO | WO 97/45082 | 12/1997 | A61F/13/15 |
| WO | WO 98/12996 | 4/1998 | A61F/5/00 |
| WO | WO 98/18505 | 5/1998 | A61L/15/60 |
| WO | WO 98/22063 | 5/1998 | A61F/13/15 |
| WO | WO 98/29501 | 7/1998 | C08L/1/28 |
| WO | WO 99/07317 | 2/1999 | A61F/13/15 |

* cited by examiner

DIAPER INCLUDING FECES MODIFICATION AGENT

This appln is a C-I-P of Ser. No. 09/107,561 filed Jun. 29, 1998, U.S. Pat. No. 6,149,636 and a C-I-P of Ser. No. 09/106,225 filed Jun. 29, 1998, U.S. Pat. No. 6,186,991 and claims benefit of Prov. Nos. 60/091,076 and 60/090,993 both filed Jun. 29, 1998.

FIELD OF THE INVENTION

The present invention relates to articles which absorb and/or contain bodily exudates, including disposable absorbent articles such as diapers, adult incontinence products, sanitary napkins and the like. More particularly, the invention relates to disposable absorbent articles including one or more agents which act to modify the physical properties of feces or other bodily wastes which may be deposited in the article.

BACKGROUND OF THE INVENTION

The major function of absorbent articles such as diapers and adult incontinence briefs is to prevent body exudates from soiling, wetting, or otherwise contaminating clothing or other articles, such as bedding, that may come in contact with the wearer. In recent years, disposable diapers, such as those disclosed in U.S. Pat. No. 5,151,092 issued to Buell et al., have become very popular and have generally replaced durable cloth absorbent articles because of their convenience and reliability. However, despite the effectiveness of such disposable absorbent articles, body exudates often still leak or are stored in the diaper such that the exudates soil and/or irritate the skin of the wearer. Additionally, body exudates often adhere aggressively to skin, increasing the difficulty of cleaning and increasing the likelihood of chronic residual contamination. The fundamental causes of these, and other key problems with absorbent articles of the art lie in the mobility under applied shear stress and adhesiveness of the feces.

The undesirable effects of leakage and/or improper containment, difficult cleanup, and/or residual skin contamination are especially evident with regard to fecal matter deposited in the diaper. Feces contained in the diaper can harm the skin of the wearer over time and feces leaking from the diaper almost invariably presents unpleasant, messy clean-ups. Thus, several attempts have been made to add features to diapers such as barriers, pockets, spacers, transverse barriers, apertured topsheets and the like to limit the movement of the fecal material across the topsheet and/or to better confine the fecal matter in the diaper. However, such attempts have been generally unsuccessful because they fail to address the fundamental causes of these problems (i.e., the properties of feces) and, because of their cost and complexity. Further, many of the means for isolating or containing feces are directed to fecal material with certain physical properties (e.g., viscosity, free water content and particle size) and are not effective with exudates with physical properties outside a very small range.

U.S. Pat. No. 4,790,836 discloses a diaper including layer of medicated powder located between the absorbent core and a water-soluble film. The medicated powder is used to promote drying of the infant's skin after the wearer wets the diaper. However, as shown in Table II, below, the embodiments disclosed in this patent do not function to provide the feces modification benefit of the present invention.

Accordingly, it would be desirable to provide an absorbent article with improved feces management properties. Further, it would be advantageous to provide an economical disposable article with the ability to minimize the negative effects of feces or other viscous bodily waste on the wearer or the caregiver. It would also be advantageous to provide an article which is designed to chemically or physically interact with the feces and to change the properties of the feces in order to improve acceptance of feces into the article and/or immobilization of the feces within the article and/or reduce the contamination of the wearer's skin with feces. Also, it would be desirable to provide an article having sufficient effective capacity and retention capability to store the physically or chemically modified feces safely and cleanly away from the wearer's skin and/or clothing throughout the expected time of use.

SUMMARY OF THE INVENTION

In order to help resolve at least some of the problems described above and otherwise found in the absorbent articles of the prior art, the present invention provides an article including an agent which is available in an effective concentration to physically or chemically modify some or all of the fecal material or other bodily exudates deposited in the article. The modification of the feces may improve acceptance and/or retention of the exudates within the article to reduce the spreading of fecal material within the diaper and/or to reduce the tendency of the fecal material to adhere to the wearer's skin. The present invention may also provide an absorbent article capable of accepting, storing and/or immobilizing the exudates in their modified form to reduce the likelihood that the waste will migrate back toward the wearer's skin once the waste is imbibed by the article. Accordingly, the absorbent article of the present invention may reduce the likelihood of harm to the wearer's skin and/or the inconvenience to the caregiver normally associated with bowel movements.

BRIEF DESCRIPTION OF THE DRAWINGS

While the specification concludes with claims particularly pointing out and distinctly claiming the subject matter which is regarded as the present invention, it is believed that the description will be better understood from the following descriptions which are taken in conjunction with the accompanying drawings in which like designations are used to designate substantially identical elements.

DETAILED DESCRIPTION OF THE INVENTION

As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner). (As used herein, the term "disposed" is used to mean that an element(s) of the diaper is formed (joined or positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) A "unitary" absorbent article refers to absorbent articles which are formed of separate parts united together to form a coordinated entity so that they do not require separate manipulative parts like a separate holder and liner.

Figure 1:
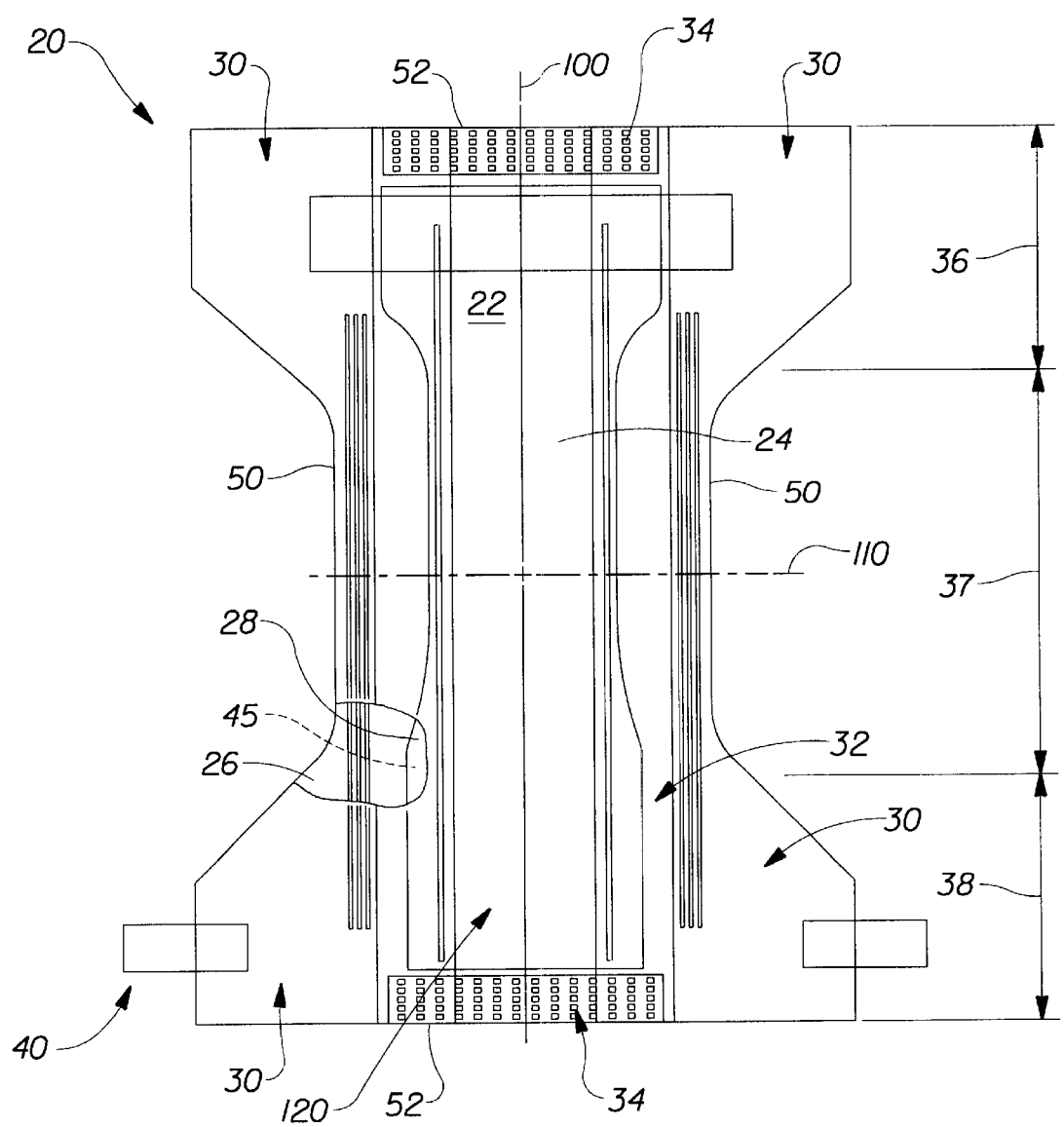
FIG. 1 is a plan view of an absorbent article embodiment of the present invention having portions cut away to reveal the underlying structure, the body-facing surface of the diaper facing the viewer.

A preferred embodiment of an absorbent article of the present invention is the unitary disposable absorbent article, diaper 20, shown in FIG. 1. (As used herein, the term "diaper" refers to an absorbent article generally worn by infants and incontinent persons about the lower torso.) However, the present invention is also applicable to other absorbent articles such as incontinence briefs, incontinence undergarments, absorbent inserts, diaper holders and liners, feminine hygiene garments, wipes, mops, bandages and the like. The present invention is also applicable to absorbent or nonabsorbent feces collection devices which can be separately applied to the wearer's perianal region.

FIG. 1 is a plan view of the diaper 20 of the present invention in a flat-out, state with portions of the structure being cut-away to more clearly show the construction of the diaper 20. The portion of the diaper 20 which faces the wearer is oriented towards the viewer. As shown in FIG. 1, the diaper 20 preferably comprises a liquid pervious topsheet 24; a liquid impervious backsheet 26; an absorbent core 28, which is preferably positioned between at least a portion of the topsheet 24 and the backsheet 26; side panels 30; elasticized leg cuffs 32; an elastic waist feature 34; and a fastening system generally designated 40. Diaper 20 is shown in FIG. 1 to have a first waist region 36, a second waist region 38 opposed to the first waist region 36 and a crotch region 37 located between the first waist region and the second waist region. The periphery of the diaper 20 is defined by the outer edges of the diaper 20 in which the longitudinal edges 50 run generally parallel to the longitudinal centerline 100 of the diaper 20 and the end edges 52 run between the longitudinal edges 50 generally parallel to the lateral centerline 110 of the diaper 20.

The chassis 22 of the diaper 20 comprises the main body of the diaper 20. The chassis 22 comprises at least a portion of the absorbent core 28 and preferably an outer covering layer including the topsheet 24 and the backsheet 26. If the absorbent article comprises a separate holder and a liner, the chassis 22 generally comprises the holder and the liner. (For example, the holder may comprise one or more layers of material to form the outer cover of the article and the liner may comprise an absorbent assembly including a topsheet, a backsheet, and an absorbent core. In such cases, the holder and/or the liner may include a fastening element which is used to hold the liner in place throughout the time of use.) For unitary absorbent articles, the chassis 22 comprises the main structure of the diaper with other features added to form the composite diaper structure.

While the topsheet 24, the backsheet 26, and the absorbent core 26 may be assembled in a variety of well known configurations, preferred diaper configurations are described generally in U.S. Pat. No. 3,860,003 entitled "Contractible Side Portions for Disposable Diaper" which issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" which issued to Roe et al. on Sep. 10, 1996; U.S. Pat. No. 5,569,234 entitled "Disposable Pull-On Pant" which issued to Buell et al. on Oct. 29, 1996; and U.S. Pat. No. 5,580,411 entitled "Zero Scrap Method For Manufacturing Side Panels For Absorbent Articles" which issued to Nease et al. on December 3; each of which is incorporated herein by reference.

The backsheet 26 is generally that portion of the diaper 20 positioned adjacent the garment facing surface 45 of the absorbent core 28 which prevents the exudates absorbed and contained therein from soiling articles which may contact the diaper 20, such as bedsheets and undergarments. Suitable backsheet films include those manufactured by Tredegar Industries Inc. of Terre Haute, Ind. and sold under the trade names X15306, X10962 and X10964. Other suitable backsheet materials may include breathable materials such as woven webs, nonwoven webs, composite materials such as film-coated nonwoven webs, and microporous films such as manufactured by Mitsui Toatsu Co., of Japan under the designation ESPOIR NO, Exxon Chemical Co., of Bay City, Tex., under the designation EXXAIRE; or monolithic films such as manufactured by Clopay Corporation, Cincinnati, Ohio under the name HYTREL blend P18-3097. Some breathable composite materials are described in greater detail in PCT Application No. WO 95/16746, published on Jun. 22, 1995 in the name of E. I. DuPont; copending U.S. Pat. No. 5,865,823 issued to Curro on Feb. 2, 1999 and U.S. Pat. No. 5,571,096 issued to Dobrin et al. on Nov. 5, 1996. Each of these references is hereby incorporated by reference herein.

The backsheet 26, or any portion thereof, may be elastically extensible in one or more directions. In one embodiment, the backsheet 26 may comprise a structural elastic-like film ("SELF") web as described in U.S. Pat. No. 5,518,801 entitled Web Materials Exhibiting Elastic-Like Behavior, which issued to Chappell, et, al. on May 21, 1996, which is incorporated herein by reference. In alternate embodiments, the backsheet 26 may comprise elastomeric films, foams, strands, or combinations of these or other suitable materials with nonwovens or synthetic films.

The topsheet 24 is preferably compliant, soft feeling, and non-irritating to the wearer's skin. Further, at least a portion of the topsheet 24 is liquid pervious, permitting liquids to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the topsheet includes fibers, the fibers may be spunbond, carded, wet-laid, meltblown, hydroentangled, or otherwise processed as is known in the art. One suitable topsheet 24 comprising a web of staple length polypropylene fibers is manufactured by Veratec, Inc., a Division of International Paper Company, of Walpole, Mass. under the designation P-8.

Suitable formed film topsheets are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; and U.S. Pat. No. 5,006,394 "Multilayer Polymeric Film" issued to Baird on Apr. 9, 1991. Other suitable topsheets 30 are made in accordance with U.S. Pat. Nos. 4,609,518 and 4,629,643 which issued to Curro et al. on Sep. 2, 1986 and Dec. 16, 1986, respectively, and both of which are incorporated herein by reference. Such formed films are available from The Procter & Gamble Company of Cincinnati, Ohio as "DRI-WEAVE" and from Tredegar Corporation of Terre Haute, Ind. as "CLIFF-T."

The topsheet 24 may be made of a hydrophobic material or be treated to be hydrophobic in order to isolate the wearer's skin from liquids contained in the absorbent core 28. If the topsheet 24 is made of a hydrophobic material, preferably at least the upper surface of the topsheet 24 is treated to be hydrophilic so that liquids will transfer through the topsheet more rapidly. The topsheet 24 can be rendered hydrophilic by treating it with a surfactant or by incorporating a surfactant into the topsheet. Suitable methods for treating the topsheet 24 with a surfactant or incorporating a surfactant in a topsheet are described in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991, and U.S. Statutory Invention Registration No. H1670, published on Jul. 1, 1997 in the names of Aziz et al. Each of these references is hereby incorporated by reference herein.

Any portion of the topsheet 24 may be coated with a lotion as is known in the art. Examples of suitable lotions include those described in U.S. Pat. No. 5,607,760 entitled "Disposable Absorbent Article Having A Lotioned Topsheet Containing an Emollient and a Polyol Polyester Immobilizing Agent" which issued to Roe on Mar. 4, 1997; U.S. Pat. No. 5,609,587 entitled "Diaper Having A Lotion Topsheet Comprising A Liquid Polyol Polyester Emollient And An Immobilizing Agent" which issued to Roe on Mar. 11, 1997; U.S. Pat. No. 5,635,191 entitled "Diaper Having A Lotioned Topsheet Containing A Polysiloxane Emollient" which issued to Roe et al. on Jun. 3, 1997: and U.S. Pat. No. 5,643,588 entitled "Diaper Having A Lotioned Topsheet" which issued to Roe et al. on Jul. 1, 1997. The lotion may function alone or in combination with another agent as the hydrophobizing treatment described above. The topsheet may also include or be treated with antibacterial agents, some examples of which are disclosed in PCT Publication No. WO 95/24173 entitled "Absorbent Articles Containing Antibacterial Agents in the Topsheet For Odor Control" which was published on Sep. 14, 1995 in the name of Theresa Johnson. Further, the topsheet 24, the backsheet 26 or any portion of the topsheet or backsheet may be embossed and/or matte finished to provide a more cloth like appearance.

The topsheet 24, the backsheet 26 may be joined to each other, the absorbent core 28 or any other element of the diaper 20 by any attachment means known in the art. For example, the attachment means may include a uniform continuous layer of adhesive, a patterned layer of adhesive, or an array of separate lines, spirals, or spots of adhesive. Alternatively, the attachment means may comprise heat bonds, pressure bonds, ultrasonic bonds, dynamic mechanical bonds, or any other suitable attachment means or combinations of these attachment means as are known in the art.

The absorbent core 28 may comprise any absorbent material known in the art. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform: chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 28 may also be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures).

Exemplary absorbent structures for use as the absorbent core are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997. Each of these patents is incorporated herein by reference.

The diaper 20 may also comprise one or more waist features 34 to help provide improved fit and containment. The elastic waist feature 34 may be constructed in a number of different configurations including those described in U.S. Pat. No. 4,515,595 issued to Kievit et al. on May 7, 1985; U.S. Pat. No. 4,710,189 issued to Lash on Dec. 1, 1987; U.S. Pat. No. 5,151,092 issued to Buell on Sep. 9, 1992; and U.S. Pat. No. 5,221,274 issued to Buell on Jun. 22, 1993. Other suitable waist configurations may include waistcap features such as those described in U.S. Pat. No. 5,026,364 issued to Robertson on Jun. 25, 1991 and U.S. Pat. No. 4,816,025 issued to Foreman on Mar. 28, 1989. All of the above mentioned references are incorporated herein by reference.

The diaper 20 may also include a fastening system 40. Some exemplary fastening systems are disclosed in U.S. Pat. No. 3,848,594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; and the herein before referenced U.S. Pat. No. 5,151,092 issued to Buell on Sep. 9, 1992; and U.S. Pat. No. 5,221,274 issued to Buell on Jun. 22, 1993. The fastening system may also provide a means for holding the article in a disposal configuration as disclosed in U.S. Pat. No. 4,963,140 issued to Robertson et al. on Oct. 16, 1990. Each of these patents is incorporated herein by reference. In alternative embodiments, opposing sides of the garment may be seamed or welded to form a pant so as to allow the article to be used as a pull-on type diaper, such as a training pant.

The diaper 20 may also include side panels 30 constructed and joined to the chassis in any suitable configuration. Examples of diapers with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151,092 issued to Buell on Sep. 9, 1992; and U.S. Pat. No. 5, 221,274 issued to Buell on Jun. 22, 1993; U.S. Pat. No. 5,669,897 issued to LaVon, et al. on Sep. 23, 1997 entitled "Absorbent Articles Providing Sustained Dynamic Fit"; EPO Publication No. WO 95/13775 A1, published May 26, 1995 entitled "Absorbent Article With Multi-Directional Extensible Side Panels"; each of which is incorporated herein by reference.

The diaper 20 preferably further includes leg cuffs 32 to help provide improved containment of liquids and other body exudates. Leg cuffs may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) which improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs. In some embodiments, it may be desirable to treat all or a portion of the leg cuffs with a lotion, as described above.

Embodiments of the present invention may also include pockets for receiving and containing waste, spacers which provide voids for waste, barriers for limiting the movement of waste in the article, compartments or voids which accept and contain waste materials deposited in the diaper, and the like, or any combinations thereof Examples of pockets and spacers for use in absorbent products are described in U.S. Pat. No. 5,514,121 issued to Roe et al. on May 7, 1996, entitled "Diaper Having Expulsive Spacer"; U.S. Pat. No.

5,171,236 issued to Dreier et al on Dec. 15, 1992, entitled "Disposable Absorbent Article Having Core Spacers"; U.S. Pat. No. 5,397,318 issued to Dreier on Mar. 14, 1995, entitled "Absorbent Article Having A Pocket Cuff"; U.S. Pat. No. 5,540,671 issued to Dreier on Jul. 30, 1996, entitled "Absorbent Article Having A Pocket Cuff With An Apex"; and PCT Application WO 93/25172 published Dec. 3, 1993, entitled "Spacers For Use In Hygienic Absorbent Articles And Disposable Absorbent Articles Having Such Spacer"; and U.S. Pat. No. 5,306,266, entitled "Flexible Spacers For Use In Disposable Absorbent Articles", issued to Freeland on Apr. 26, 1994. Examples of compartments or voids are disclosed in U.S. Pat. No. 4,968,312, entitled "Disposable Fecal Compartmenting Diaper", issued to Khan on Nov. 6, 1990; U.S. Pat. No. 4,990,147, entitled "Absorbent Article With Elastic Liner For Waste Material Isolation", issued to Freeland on Feb. 5, 1991; U.S. Pat. No. 5,62,840, entitled "Disposable Diapers", issued to Holt et al on Nov. 5, 1991; and U.S. Pat. No. 5,269,755 entitled "Trisection Topsheets For Disposable Absorbent Articles And Disposable Absorbent Articles Having Such Trisection Topsheets", issued to Freeland et al on Dec. 14, 1993. Examples of suitable transverse barriers are described in U.S. Pat. No. 5,554,142 entitled "Absorbent Article Having Multiple Effective Height Transverse Partition" issued Sep. 10, 1996 in the name of Dreier et al.; PCT Patent WO 94/14395 entitled "Absorbent Article Having An Upstanding Transverse Partition" published Jul. 7, 1994 in the name of Freeland, et al.; and U.S. Pat. No. 5,653,703 Absorbent Article Having Angular Upstanding Transverse Partition, issued Aug. 5, 1997 to Roe, et al. All of the above-cited references are hereby incorporated by reference herein.

Figure 5:
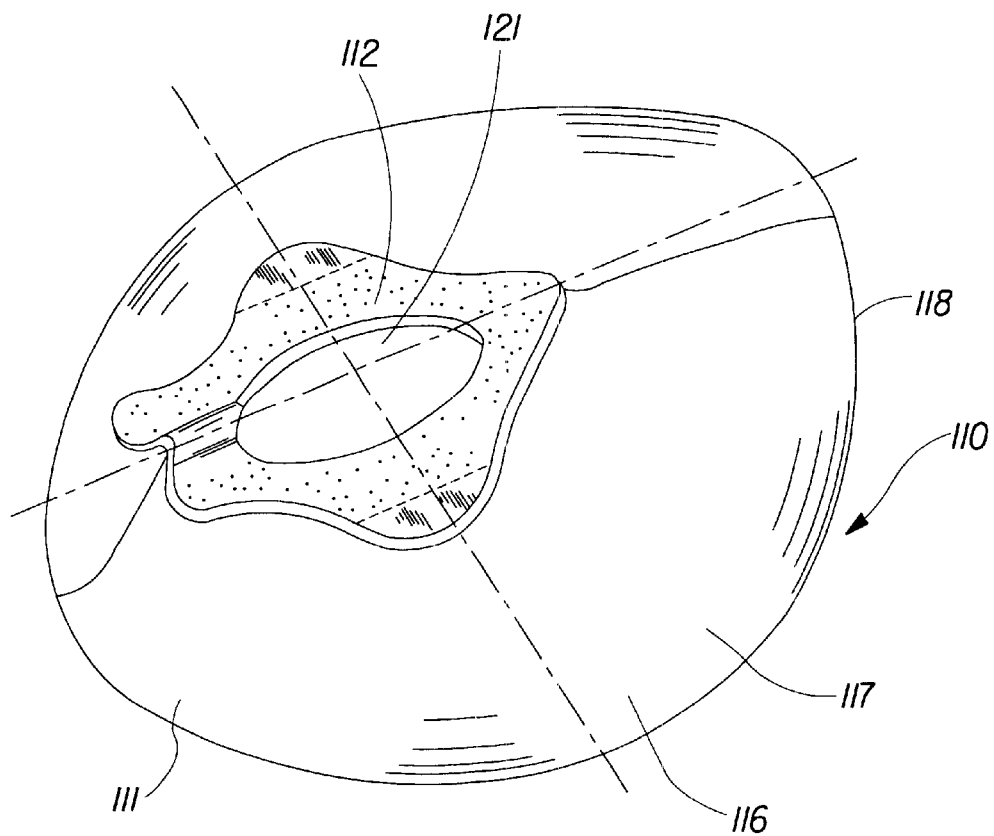
FIG. 5 is a perspective view of a waste bag embodiment of the present invention.
Figure 6:
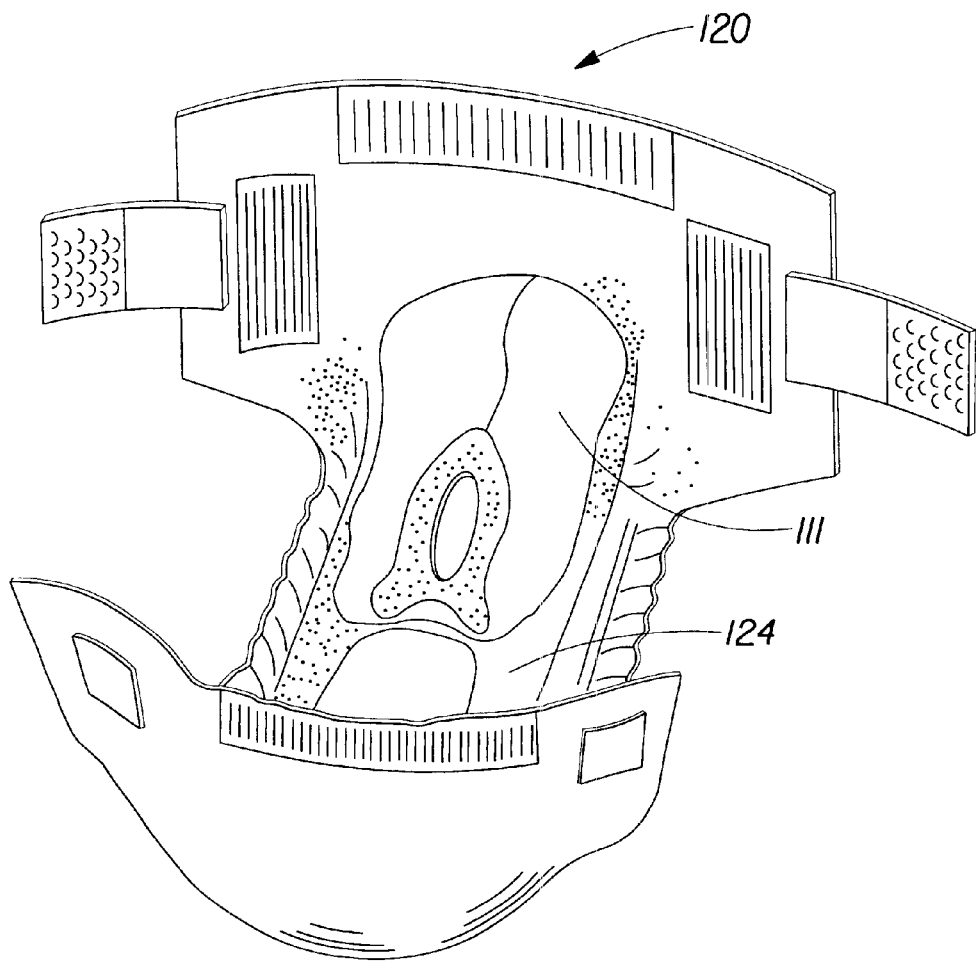
FIG. 6 is a perspective view of an absorbent article including a waste bag.

Embodiments of the present invention may also include a waste management device 110 such as is shown in FIG. 5. The waste management device 110 may include a waste bag 111 to collect feces, urine or both. The waste bag 111 may have an aperture 121 and a flange 112 surrounding the aperture for preferably adhesive attachment to the perianal area of a wearer. Further, the waste management device 110 has been found to be particularly useful and beneficial when used in conjunction with a garment, or diaper, preferably a disposable diaper. One example of a diaper 120 including a waste bag 111 is shown in FIG. 6. If associated with a diaper 120 or other garment, the waste bag 111 may be disposed on or joined to any surface of the article. The bag 111 may be joined to the article by any known means, including any of the joining or attaching means described herein and/or any other joining means such as adhesive, hook and loop fasteners, magnetics, belts, ties, straps, snaps, etc. In one embodiment, the waste bag 111 is joined to the topsheet 124 of the diaper 120.

The waste bag 111 is preferably a flexible receptacle for the containment of excreted fecal matter or urine. Thus, the waste bag 111 is preferably liquid impermeable, and yet it may be breathable. Further, the waste bag 111 is designed of sufficient strength to withstand typical wearing conditions, such as sitting.

The waste bag 111 may comprise one or multiple layers. In one embodiment, the waste bag 111 may comprise three layers, preferably one film and two non-woven layers. Suitable film materials for any of the film layers preferably comprise a thermoplastic material. The thermoplastic material can be selected from among all types of hot-melt adhesives, polyolefins especially polyethylene, polypropylene, amorphous polyolefins, and the like; material containing meltable components comprising fibres or polymeric binders including natural fibres such as cellulose—wood pulp, cotton, jute, hemp; synthetic fibres such as fibreglass, rayon, polyester, polyolefin, acrylic, polyamid, aramid, polytetrafluroethylene metal, polyimide; binders such as bicomponent high melt/low melt polymer, copolymer polyester, polyvinyl chloride, polyvinyl acetate/chloride copolymer, copolymer polyamide, materials comprising blends wherein some of the constituent materials are not meltable; air and vapour permeable materials including microporous films such as those described above with respect to the backsheet and monolithic breathable materials such as HYTREL™ available from DuPont and Pebax™ available from ELF Atochem, France.

The waste bag 111 may have any shape or size. Preferred shapes include flat circular type bags, cone shaped bags, truncated cone shaped bags and pyramidal or truncated pyramidal shaped bags and flat T shaped bags. Further, the waste bag 111 may be provided from a unitary piece of material or a number of separate pieces of material which may be identical or different and which may be sealed at their respective peripheries.

The waste bag 111 may also contain absorbent material. The absorbent material may comprise any absorbent material which is capable of absorbing and retaining liquids. The absorbent material may comprise a wide variety of liquid-absorbent materials commonly used in disposable diapers and other absorbent articles. Some examples are described herein with respect to the absorbent core.

The waste bag 111 is provided with an aperture 121 whereby fecal matter or urine is received from the body prior to storage within the bag cavity. The aperture 121 is preferably surrounded by a flange 112 and may be provided in any shape or size, such as circular, oblong, heart shaped and may be symmetrical or asymmetrical, preferably the aperture has an oblong configuration either in the longitudinal or in the transversal direction. The flange may comprise projections designed to fit the perineal, genital and/or coccygeal area of the wearer.

The flange 112 should be made of soft, flexible and malleable material to allow easy placement of the flange 112 to the perianal or uro-genital area. Typical materials include nonwoven materials, wovens, open celled thermoplastic foams, closed-cell thermoplastic foams, composites of open celled foams and stretch nonwoven, and films.

The waste bag 111 preferably further comprises a joining or attachment means to secure the device to the wearer. Such means may comprise any of the joining or attachment means described herein or any other suitable joining or attachment means known in the art, including straps, belts, hook and loop fasteners, pins, snaps and/or a body-compatible adhesive applied to the wearer facing portion of the waste bag 111 or the flange. Any skin-friendly water resistant pressure sensitive adhesive may be used to attach the device to the perianal or uro-genital area of the wearer, such as hydrocolloid adhesives and hydrogel adhesives. Particularly effective adhesives in providing the desired adhesive properties to secure the flange to the skin of the wearer at the sensitive perianal area, while allowing for relatively painless application and removal, are formed from crosslinking polymers with a plastisicer to form a 3-dimensional matrix.

The article of the present invention may also include one or more feces modifying agents ("FMAs", "viscous bodily waste modifying agents", "modifying agents" or "agents") in an effective concentration capable of modifying the chemical or physical properties of viscous bodily waste, such as feces and menses. As used herein, "feces modifying agent" (or FMA) refers to any chemical composition capable of increasing the hardness of a given fecal analog, or preferably actual feces, by at least about 100% or decreasing the hardness of a given fecal analog, or preferably actual feces, by at least about 25%, as measured by the Hardness Method, described below. However, depending on the particular article design and the type of feces, embodiments are contemplated which increase or decrease the effective viscosity of feces, increase or decrease the ease of dewatering the feces, decrease the stickiness of the feces, decrease the adhesion characteristics of the feces, or any combination of the above. Although the feces modifying agents of the present inventions may be capable of modifying the properties of solid feces, the FMAs are generally most effective in altering the properties of viscous fluid feces which generally have a viscosity of greater than about 10 cP and less than about $10^7$ cP at a shear rate of one 1/sec, (at about 35 degrees C.), and more particularly between about $10^2$ cP and $10^7$ cP at a one 1/sec shear rate, in a controlled stress rheometry test using parallel plates on a controlled stress rheometer. (For reference, water is at 1.0 cP at 20 degrees C. and Jif Creamy peanut butter (available from the Procter & Gamble Co., Cinti., Ohio) is approximately $4\times10^5$ cP at 25 degrees C. at this same shear rate). The method for determining viscosity, as used herein, is described in detail in the Test Methods section below.

Regardless of the specific effect of the chemical agent on feces, the agent must be available to the feces in order to perform its function. As used herein, in the context of FMAs, the term "available" indicates that the agent is positioned within the article or presented by the article or a component of the article during the course of normal wearing of the article so as to directly contact at least a portion of the feces deposited in the article or on the wearer's skin. If the agent is positioned within a structure (e.g., in an absorbent layer under a topsheet), the structure must be substantially penetrable by the feces. In such cases, the agent is "available" if the structure has an Acceptance Under Pressure greater than about 0.50 g/cm2/J, and preferably greater than about 1.0 g/cm2/J, as measured by the Acceptance measurement described in the Methods section below. If the agent is encapsulated, it should be released by the article at or about the time when the feces insults the article. For example, the FMA may be retained by a water-soluble film which, upon contact with urine or fecal water, dissolves and releases the FMA to contact the feces.

An "effective concentration" of an FMA, as used herein, refers to the relative amount of the agent required to have a measurable effect on the Hardness (as measured by the Hardness Method described below) of at least a portion of the feces in the article or on the skin of the wearer. Data illustrating an "effective concentration" is provided below. Preferably, a concentration of an FMA of at least about 0.01 weight percent of the feces to be treated is desirable, and more typically between about 0.1 and about 50 weight percent of the FMA is available to the feces. For example, to treat an entire 25 gram feces loading in a diaper (i.e., a "bulk" treatment) at a 5 weight percent level, 1.25 grams of the FMA must be available to the fecal mass (assuming the specific gravity of the feces is 1.0). Thus, the FMA is preferably present in the article in concentrations ranging from about 0.001% to about 50% by weight of the article. Typically, however, the concentration is between about 0.01 and about 20 weight percent of the article.

The FMA is preferably capable of reducing the Hardness of a fecal analog, and preferably, actual feces, by about 25% or increasing the Hardness by about 100% at a concentration of no more than about 20 weight percent of the feces to be treated at room temperature (20–25° C.). More preferably, the FMA is capable of reducing the Hardness of a fecal analog or actual feces by about 25%, or increasing the Hardness by about 100% at a concentration of no more than about 10 weight percent of the feces to be treated. Even more preferably, the FMA is capable of reducing the Hardness of a fecal analog or actual feces by about 25%, or increasing the Hardness by about 100% at a concentration of no more than about 5 weight percent of the feces to be treated. In other preferred embodiments, the FMA is capable of reducing the Hardness of a fecal analog or actual feces by 25%, or increasing the Hardness by about 100% at a concentration of no more than about 1 weight percent of the feces to be treated. In yet other preferred embodiments, the FMA is capable of reducing the Hardness of a fecal analog or actual feces by about 25%, or increasing the Hardness by about 100% at a concentration of no more than about 0.5 weight percent of the feces to be treated. Typically, the FMA is capable of reducing the Hardness of a fecal analog or actual feces by about 25%, or increasing the Hardness by about 100% at a concentration of between about 0.1 and about 10 weight percent of the feces to be treated.

Preferably, the defined reduction or increase in Hardness is effected within the range of between about 30 minutes, more preferably within about 15 minutes, even more preferably within about 5 minutes, even more preferably within about 3 minutes, and most preferably in about 1 minute after contact with the feces. Typically, the desired Hardness change is effected within the range of about 1 minute to about 10 minutes. In more preferred embodiments, the defined reduction or increase in Hardness is effected within about 3 minutes at an FMA concentration of no more than about 5% by weight of the feces to be treated or within 3 minutes at an FMA concentration of about 1.5% by weight of the feces to be treated. In other preferred embodiments, the FMA is capable of increasing the Hardness of a fecal analog, or actual feces, by about 200% within about 3 minutes at a concentration of no more than about 5%. In yet other preferred embodiments, the FMA is capable of increasing the Hardness of a fecal analog, or actual feces, by about 400% within about 3 minutes at a concentration of no more than about 5%.

In other preferred embodiments, the FMA is capable of reducing the Hardness of a fecal analog, or actual feces, by about 50% within about 3 minutes at a concentration of no more than about 5%.

The reference Hardness values of two synthetic fecal analog materials are presented in Table I. (Hardness has been found to be closely related to the complex modulus of feces.) Analog A represents the water content, Hardness, and adhesion properties of typical "runny" feces, while Analog B represents typical "pasty" feces. Two consistencies of feces are simulated so as to better illustrate the activity of the FMAs. The methods of preparing Analogs A and B are described in the Test Methods section below.

TABLE I

| Fecal Analog | Fecal Analog Hardness (g) |
| --- | --- |
| A | 8.6 |
| B | 620 |

Fecal analogs A and B provide a repeatable means to evaluate FMA performance. However, actual feces is a very complex material. For certain chemical treatments, the FMA effect may be greater for actual feces than for either of the analogs described above. For one of the agents evaluated, Hardness data is presented in terms of hardness change for feces analogs and actual feces, in order to demonstrate the similarity in relative responses to the treatment. The actual feces used in these experiments consisted of both a composite "runny" feces sample and a composite "pasty" feces sample. The composite runny feces sample was pooled using several bowel movements (uncontaminated by urine) produced by two U.S. breast-fed, four month old, male infants. The composite "pasty" sample was pooled using several bowel movements (uncontaminated by urine) produced by two U.S. infants—a four month old, formula-fed male and a 12 month old male eating a "transition" diet between breast milk and table food. Feces pooling was accomplished via a Seward Stomacher 400 Lab System by Seward Medical, Ltd. of London, UK. For reference, the Hardness of the untreated (i.e., as collected) pooled runny feces sample was 28 grams, and the Hardness of the untreated pooled pasty feces sample was 297 grams.

The effect of mixing several comparative examples with fecal analogs are illustrated in Table II below. All comparative materials were mixed with the fecal analog as described below in the Sample Preparation Method. As is evident in the data above, the desired changes in Hardness were not achieved by the comparative materials.

TABLE II

| Fecal Analog | Comparative Additive | Concentration (wt. %) | Treated Fecal Analog Hardness (g) |
|---|---|---|---|
| A | Corn Starch (Dietary Fiber Control, Sigma Chemical Co., St. Louis, MO, S-2388) | 1.0 5.0 | 12.6 8.6 |
| A | Pure Corn Starch Baby Powder (Johnson & Johnson, Co., Skillman, NJ) | 1.0 5.0 | 14.4 7.1 |
| A | Baby Powder (talc) (Johnson & Johnson, Co.) | 1.15 | 10.2 |
| B | Corn Starch (Dietary Fiber Control, Sigma Chemical Co., St. Louis, MO, S-2388) | 1.1 4.9 | 643 533 |
| B | Baby Powder (talc) (Johnson & Johnson, Co.) | 1.0 5.0 | 854 679 |

The Feces Modifying Agent of the present invention may include one or more "water liberating" agents capable of separating the liquid portion of the feces (i.e. water) from the solid structure of the feces and/or reducing the degree of "binding" of the feces water to the solid feces components. Without wishing to be bound by theory, it is believed that feces comprises water in several states. For example, the feces includes free water, bound water (bound water may be held in a "colloidal" structure via an electrical double layer on the surface of the particles, organized in a polymeric "gel" structure, or associated with other charged elements in the fecal matrix), and entrapped water (e.g., inside bacteria). It is also believed that the solid and polymeric components of the feces act to organize bound water into higher energy states (i.e., more energy is required to separate the water from the matrix) as compared to free water or "unbound" water. (The solid components of feces (soluble and insoluble) generally include one or more of the following; undigested food material (e.g., fiber), bacteria, long chain polysaccharides, fats, soaps, protein globules, and the like.) The water content of viscous bodily wastes such as fecal material is relatively high, generally greater than 50%, and often between about 60% and about 95% by weight.

However, conventional absorbent articles are incapable of separating much of the water from the fecal matrix. (As used herein, the term "fecal matrix" refers to the feces as a whole, including any solid or soluble components such as bio polymers.) Thus, very little of the feces (generally only a portion of the free water) is actually absorbed such that it can be adequately contained.

In order to improve the efficacy of the absorbent structure with regard to feces, the FMAs of the present invention may include "water liberating" agents which act to separate the bound and/or entrapped water from the fecal matrix. "Liberated water" in feces or analogs may remain within the feces mass resulting in reduced feces viscosity, or completely separate from feces forming two distinct phases, water and the remaining feces. If the water is completely separated, the remaining feces becomes significantly harder. In the absence of absorbent materials in contact with the feces, liberation of water from the fecal matrix decreases the viscosity of the overall fecal mass by permitting the liquid portion of the fecal matter to flow more freely. If, however, the liberated water is completely separated from the fecal mass, the viscosity or hardness of the remaining feces will be increased. Further, the removal of water helps to agglomerate the fecal solids into more discrete solid particles which are generally more strongly associated with each other than when held in the matrix (it is believed that a reduction in inter-particle repulsive forces causes the particles to aggregate and release water held between them). The feces' decrease in viscosity promotes its penetration into the absorbent structure. Greater penetration of the absorbent structure, in turn, increases the likelihood that the absorbent article will be able to store and/or immobilize the waste away from the wearer's skin. Accordingly, the absorbent article's overall performance may be significantly improved.

While the liberation of water caused by the destabilization of the colloidal or gel nature of the feces preferably decreases the viscosity of the feces and increases the ability of the feces to flow into the absorbent structure, it may also enhance the ability of any absorbent materials in contact with the treated feces to dewater and immobilize the feces. However, in some embodiments it may be undesirable to have immobilization occur on the surface of the absorbent structure because the solid fraction of the feces may still be accessible to the user. Thus, it maybe preferred to limit the contact of viscous bodily waste with absorbent media until the feces has penetrated the structure to the desired depth or location for immobilization away from the user. In such embodiments, the feces viscosity is preferably decreased while on the surface of, or prior to contact with the absorbent structure, and dewatered and/or immobilized once it has sufficiently penetrated the structure.

Feces Modifying Agents which act to decrease the viscosity of feces as described above include, but are not limited to the following: organic and inorganic flocculants, and the like. Inorganic flocculants include but are not limited to divalent and trivalent metal salts, including but not limited to salts of iron, aluminum, calcium, and sodium and mixtures thereof It is believed that such salts form hydrolysis products which associate with the charged surfaces of the particulate matter in the feces colloidal structure, resulting in flocculation (i.e., flocculation via any of the mechanisms described above). Some examples include ferrous chloride, ferric chloride, aluminum sulfate, aluminum chloride hydroxide, sodium aluminate, calcium sulfate, poly-aluminum-silicate-sulfate (available from Handy Chemical, Quebec under the trade name PASS), ferrous sulfate, calcium carbonate, and the like.

Organic flocculants include but are not limited to natural substances like albumin, xanthan gum, and guar gum. Synthetic flocculants are generally non-crosslinked, water-soluble molecules or polymers and may include acrylic and acrylamide polymers and their derivatives (in very low concentrations (a few hundredths of a weight percent)), polyvinyl pyrollidone, poly methacrylates, polyamines, polyethylene oxide, and allylamine polymers. Preferably, these are cationic polymeric species. (Although applicants do not wish to be bound by theory, it is believed that these agents function by associating with the negatively charged regions of the feces particulate fraction and reducing the net inter-particle repulsive charge.) Some of the synthetic flocculants may act to increase the viscosity of aqueous solutions if used in high concentrations and will be discussed below as feces thickening agents. It is also important to note that if some of the organic flocculants are used in too high a concentration their effect may be reversed. Thus, the water may be held more tightly by the feces due to the tendency of these agents to form gels if used in excess of the amount necessary to associate with the charged particulates.

Without wishing to be bound by theory, it is believed that flocculants destabilize colloids by enhancing aggregation of the constituent particles in the matrix via any of a number of mechanisms, including charge neutralization, bridging, and electrostatic patching. Flocculation of colloidal systems via charge neutralization occurs when the agent adsorbs to the surface of the constituent particles and reduces the electrical double-layer potential. The agent acts in theory, to reduce the stabilizing repulsive surface charges at the surface of the solid particles in the matrix by accumulating at the charged interfaces of the particles, allowing the particles to aggregate. Thus, the water that was held "bound" in the matrix (i.e., held between the particles) is freed as the structure collapses. It is believed that "bridging" may occur when a long-chain polyelectrolyte adsorbs onto particles in the colloidal matrix and extends into the bulk of the matrix, where it can span the distance of closest approach of other particles in the matrix. This results in the aggregation of particles and the freeing of bound water. "Electrostatic patching" may occur where, as the flocculating polymer is completely adsorbed onto the particle, geometric limitations prevent complete charge neutralization. This may result in the formation of positive "patches" or areas on the particles that attach to negative patches on other particles upon collision. This also results in aggregation of the particles due to the net reduction in electrical repulsion between the particles.

Some crosslinked derivatives of the synthetic organic flocculants (e.g., polyacrylates), or derivatives thereof, are known in the art as superabsorbent polymers, and function to form water-insoluble gels upon contact with very low viscosity aqueous wastes such as urine and menses. However, because these crosslinked species cannot readily dissociate (i.e., dissolve) and adsorb to the particulate species within the feces matrix, they do not function as flocculants.

Viscosity reduction performance of several representative water-liberating agents is illustrated in the data in Table III. The mixing of the agent and the fecal analog or feces is described below in the Sample Preparation Method).

TABLE III

| Fecal Analog | Flocculant | Concentration (wt. %) | Treated Fecal Analog Hardness (g) | % Change in Hardness |
|---|---|---|---|---|
| A | calcium hydroxide (ACS Reagent, Sigma Chemical Co., St. Louis, MO C-5551) | 1.1 | 5.7 | (34)* |
| A | calcium sulfate hemihydrate (#30, 766-1 Aldrich Chemical Co., Milwaukee, WI) | 1.0 | 4.9 | (43) |
| B | polyvinyl pyrollidone (PVP) (Avg. MW = 40,000, k-value: 29–32, Sigma PVP-40) | 1.0 | 425 | (31) |
| B | sodium polymethacrylate (30 wt % solution in water, Avg. MW = 6000, Avg. Mn = 4000, Aldrich #43, 449-3) | 2.4 | 446 | (28) |
| B | sodium polymethacrylate | 4.7 | 411 | (34) |

*( ) indicates decrease in the value.

Feces Modifying Agents which act to decrease the viscosity of feces as described above may also include reducing agents. For example, agents that reduce disulfide bonds (—S—S-bonds) as found in colonic mucous colomin mucous generally comprises (macromolecular glycoproteins linked by disulfide bonds) can effect a significant viscosity reduction in feces having high mucous content. While not wishing to be bound by theory, it is believed that reduction of the mucin disulfide bonds (which function as crosslinks between mucin polymer chains) significantly reduces the average molecular weight of the glycoprotein structure in feces such as runny feces to a level well below the "gel point" of the mucin (i.e., long-distance structure becomes impossible due to the relatively small size of the glycoproteins). Exemplary reducing agents include sulfites such as sodium hydrogensulphite, sodium sulfite and sodium dithionite, thiols and thiol alcohols (e.g., 2-mercaptoethanol, dithiothreitol, and dithioerythritol), mercaptoacetic acid, sodium thioglycolate, thiolactic acid, thioglycoamide, glycerol monothioglycolate, borohydrides (e.g., sodium borohydride), ternary amines, thiocyanates such as sodium thiocyanate, thiosulfates such as sodium thiosulfate, cyanides such as sodium cyanide, thiophosphates such as sodium thiophosphate, arsenites such as sodium arsenite, phosphines such as triphenyl phosphine, phenols such as thiophenol and p-nitrophenol, betaines, and others including, but not limited to, lithium aluminumhydride, aluminum chloride, guanidine hydrochloride, stannous chloride, hydroxylamine, and $LiHB(C_2H_5)_3$.

Viscosity reduction performance of a representative reducing agent (mixed with a fecal analog and actual feces as described in the Sample Preparation Method in the Test Methods section below) is illustrated in the data in Table IV.

TABLE IV

| Feces/Fecal Analog | Reducing Agent | Concentration (wt. %) | Treated Feces/Fecal Analog Hardness (g) | % Change in Hardness |
|---|---|---|---|---|
| Composite Runny Feces Sample | sodium hydrogensulfite (Aldrich. #24,397-3) | 5.0 | 10.1 | (50)* |
| B | sodium hydrogensulfite (see above) | 5.0 | 311 | (64) |

*( ) indicates decrease in the value.

In other particularly preferred embodiments of the present invention, modifying agents which generally increase the structure of the feces by increasing the degree of water binding are employed to increase the viscosity and reduce the mobility of the feces. This may be accomplished via the use of thickening agents in the appropriate concentrations. Thickening agents may be natural or synthetic and are generally water-soluble, (typically non-crosslinked) polymers, such as CMC (carboxymethyl cellulose), hydroxypropyl methylcellulose, hydroxyethyl cellulose, polyacrylic acid and its derivatives, carageenan, polyacrylamide and its derivatives, (polyethylene)imines, gums (such as xanthan, guar, karaya, agar, locust bean gum, pectin, and gum ghatti, or mixtures thereof) and other similar materials. Cationic polymers are preferred due to the anionic surfaces of fecal bacteria and biopolymers. Thickening agents increase the viscosity of the feces by dissolving in the free water in the feces and osmotically "binding" water, thereby increasing the solid "structure" of the feces. Generally, large, insoluble polyelectrolytic polymeric particles such as conventional superabsorbents are not able to dissolve in the feces free water and create a matrix within the feces at the molecular level. Some FMAs may perform differently on different types of feces (e.g., a FMA that acts as a flocculant on one type of feces, may act as a thickening agent on another type due to variance in the structural character of the specific type of feces). One example of this is calcium hydroxide which functions as a flocculant for a runny fecal analog, but as a thickener for a pasty fecal analog in the same concentrations.

Table V shows the effects of concentration of various FMAs acting as thickening agents on the fecal analogs and/or feces. The mixing of the agent and the fecal analog or feces is described below in the Sample Preparation Method.

TABLE V

| Feces/Fecal Analog | Thickener | Concentration (wt. %) | Treated Feces/Fecal Analog Hardness (g) |
|---|---|---|---|
| A | Gum Guar (Sigma G-4129) | 1.1<br>5.0 | 35<br>110 |
| A | poly(acrylamide co-acrylic acid) (Avg. mw = ca. 5 × 10$^6$, Aldrich #18,127-7) | 1.2<br>4.9 | 9.6<br>101 |
| A | poly acrylamide (ground into powder, Sigma P-2433) | 1.0<br>5.0 | 130<br>536 |
| B | carboxymethyl cellulose (CMC) | 2.5<br>5.0<br>10.0 | 55<br>368<br>935 |

TABLE V-continued

| Feces/Fecal Analog | Thickener | Concentration (wt. %) | Treated Feces/Fecal Analog Hardness (g) |
|---|---|---|---|
| B | Gum Xanthan (practical grade, Sigma G-1253) | 2.5<br>10.0 | 56<br>362 |
| B | carageenan (Type I, commercial grade, Sigma C-1013) | 5.0 | 1641 |
| composite runny feces sample | carageenan (see above) | 5.0 | 150 |
| B | hydroxypropyl methylcellulose (Sigma H-7509) | 5.0 | 1775 |
| composite runny feces sample | hydroxypropyl methylcellulose (see above) | 5.0 | 111 |
| composite pasty feces sample | hydroxypropyl methylcellulose (see above) | 5.0 | 1060 |

In still other preferred embodiments, the modifying agent comprises an ionic complexing agent. Ionic complexing agents may include any single component which complexes with itself or water or other chemical entities in the feces to form regions of increased structure and rigidity within the feces. The resultant complex acts to stabilize or bind water more tightly in the feces. Exemplary ionic complexing agents include ZnO, MgO, MnO, CaO, calcium hydroxide, $Al_2O_3$, aluminum salts, zinc salts such as zinc acetate and zinc glucanate, gelatin, quaternary ammonium salts, ethanolamines, alginic acid, cetyl trimethyl ammonium bromide and the like). Alternatively, the ionic complexing agent may comprise a two (or more) component system, wherein the complex (i.e., longer-range structure) is created by the interaction of the two added components (e.g., aluminum, calcium, or zinc salts plus alginic acid and/or salts thereof). The ionic complexing agents may form crystal hydrates when complexing with water. In general, calcium-containing compounds or systems (e.g., CaO, calcium hydroxide, and calcium alginate, etc.) are some of the most effective feces modifying agents.

Table VI shows the effect of various ionic complexing agents on fecal analog or feces Hardness. (Mixing of the fecal analog and/or feces was performed as specified in the Sample Preparation Method below.)

TABLE VI

| Fecal Analog/Feces | Ionic Complexing Agent/System | Concentration (wt. %) | Treated Fecal Analog/Feces Hardness (g) |
|---|---|---|---|
| A | calcium oxide (Sigma C-2178) | 1.0<br>5.0 | 26<br>385 |
| A | alginic acid/zinc chloride (50%/50% by wt.) (alginic acid - sodium salt, from kelp, "high viscosity"-Sigma A-7128; zinc chloride-Sigma Z-4875) | 5.0 (total mixture) | 114 |
| B | calcium hydroxide (ACS reagent, Sigma C-5551) | 1.0<br>5.0 | 1206<br>1223 |
| B | zinc oxide (ACS reagent, Sigma Z-1753) | 5.1 | 1192 |
| B | sodium chloride (ACS Reagent, Sigma S-9888) | 5.2 | 1275 |

TABLE VI-continued

| Fecal Analog/Feces | Ionic Complexing Agent/System | Concentration (wt. %) | Treated Fecal Analog/Feces Hardness (g) |
|---|---|---|---|
| B | calcium chloride (anhydrous, Sigma C-4901) | 4.9 | 1405 |
| A | alginic acid, ammonium-calcium salt (Sigma A-7253) | 5.0 | 513 |
| B | alginic acid, ammonium-calcium salt (Sigma A-7253) | 5.0 | 2070 |
| Composite runny feces | alginic acid, ammonium-calcium salt (Sigma A-7253) | 5.0 | 52 |
| Composite pasty feces | alginic acid, ammonium-calcium salt (Sigma A-7253) | 5.0 | 908 |

In still other preferred embodiments, the FMA includes a crosslinker that can react with functional groups on the components of the feces or with itself to form long distance structure in the fecal matrix. The crosslinking effect uses the fecal components as "monomers" that are linked together by a multifunctional (e.g., difunctional) modifying agent to form a longer-range network structure. Such modifying agents may target amine groups (e.g., dialdehydes, dialdehyde starches), hydroxl groups (e.g., epichlorohydrin), and/or carboxyl groups (e.g., diamines). Other exemplary FMA crosslinking agents are Kymene 557-H, 557-LX, and 2064 (available from Hercules, Inc. of Wilmington, Del.) Table VII shows the effects of an exemplary crosslinking agents on fecal analog Hardness after 15 minutes (t=15 minutes after beginning the stirring process, as described in the Sample Preparation Method below).

TABLE VII

| Analog | Crosslinking Agent | Concentration (%) | Fecal Analog Hardness |
|---|---|---|---|
| B | Kymene 2064 (Hercules, Inc., Wilmington, DE) | 5.0 | 1405 |

While in certain embodiments it is desirable to treat the entire mass of feces within the article (i.e., "bulk" treatment), in some preferred embodiments only a portion of the feces is treated with the FMA. In these embodiments the FMA may penetrate only a relatively small distance into the feces, thereby forming a modified external layer that is relatively stiff and non-sticky. This may be preferable from an FMA utilization standpoint or to eliminate the need for mixing of the FMA into the fecal mass. The modified external layer is a region or layer of feces at or near the surface of the feces mass with different physical properties than the remainder of the feces mass. Preferably, the modified layer is harder (i.e., has a higher yield stress), less sticky, and/or has a higher resistance to diffusion of volatile molecules contained in the feces than does the remaining feces, resulting in decreased spreading/mobility of the feces mass and/or decreased adhesion of the feces mass to the wearer's skin and/or reduced fecal odor. Preferably, the modified external layer region is between about 1 and about 1000 microns in thickness and may cover all or any portion of the fecal mass. For example, it may be suitable to treat only the feces at the skin/feces interface (e.g., to reduce adhesion and/or promote cleaning or reduce spreading across the wearer's skin or to promote absorption or to reduce spreading within the article). Thus, to treat a 1 millimeter thick layer of a fecal mass over a 30 square cm area of the skin or article topsheet at a 10 weight percent level, 0.30 grams of the FMA must be available to the feces in the region of contact with the feces (assuming the specific gravity of the feces is 1.0).

In various embodiments, the FMA may be organic or inorganic, a low molecular weight molecule or polymeric in nature, and/or may be a liquid, solid (e.g., powder, fiber, film, web), or a semi-solid, or combinations thereof. The FMA may be presented in a water/oil or oil/water emulsion, a suspension, or mixture. The FMA may be disposed in the article as an individual discrete element (e.g., as a fibrous batt or layer within or attached to the article) or may be held in or on a carrier vehicle, such as a lotion or skin care composition (described below), a web, or may be releasably encapsulated in a packet, cell, or envelope structure.

In embodiments wherein the FMA is delivered via a skin care composition, it may be soluble in the skin care composition or may be held in suspension or as a simple mixture. Larger FMA particles (e.g., preferably greater than about 250 microns in largest dimension) may be at least partially embedded in or held adhesively by the skin care composition. Some exemplary materials useful in the skin care compositions which may be used in embodiments of the present invention include Category I actives as defined by the U.S. Federal Food and Drug Administration's (FDA) Tentative Final Monograph on Skin Protectant Drug Products for Over-the-Counter Human Use, which presently include: alantoin, aluminum hydroxide gel, calamine, cocoa butter, dimethicone, cod liver oil (in combination), glycerine, kaolin, petrolatum, lanolin, mineral oil, shark liver oil, white petrolatum, talc, topical starch, zinc acetate, zinc carbonate, zinc oxide, and the like. Other potentially useful materials are Category III actives as defined by the U.S. Federal Food and Drug Administration's Tentative Final Monograph on Skin Protectant Drug Products for Over-the-Counter Human Use tentative final monograph on skin protectant drug products for over-the-counter human use, which presently include: live yeast cell derivatives, aldioxa, aluminum acetate, microporous cellulose, cholecalciferol, colloidal oatmeal, cysteine hydrochloride, dexpanthenol, Peruvian balsam oil, protein hydrolysates, racemethionine, sodium bicarbonate, Vitamin A, and the like. Many of the FDA monographed skin care ingredients are currently utilized in commercially available skin care products, such as A and D® Ointment, VASELINE® Petroleum Jelly, DESITIN® Diaper Rash Ointment and Daily Care Ointment, GOLD BOND® Medicated Baby Powder, AQUAPHOR® Healing Ointment, BABY MAGIC® Baby Lotion, JOHNSON'S ULTRA SENSITIVE® Baby Cream, Johnson's baby lotion, lip balms, etc. Other suitable skin care compositions are described in detail in U.S. Pat. Nos. 5,643,588, 5,607,760, 5,609,587, and 5,635,191. The disclosures of each of these patents is incorporated herein by reference.

The skin care compositions useful in the present invention preferably have a melting profile such that they are relatively immobile and localized on the wearer-contacting surface of the article at room temperature, are readily transferable to the wearer at body temperature, and yet are not completely liquid under extreme storage conditions. Preferably, the compositions are easily transferable to the skin by way of normal contact, wearer motion, and/or body heat.

In preferred embodiments, the skin care compositions useful herein are solid, or more often semi-solid, at 20° C., i.e. at ambient temperatures. By "semisolid" is meant that the composition has a rheology typical of pseudoplastic or plastic liquids. When no shear is applied, the compositions can have the appearance of a semi-solid but can be made to flow as the shear rate is increased. This is due to the fact that, while the compositions may contain primarily solid components, they may also include some minor liquid components. Preferably, the compositions of the present invention have a zero shear viscosity between about $1.0 \times 10^6$ centipoise and about $1.0 \times 10^8$ centipose. More preferably, the zero shear viscosity is between about $5.0 \times 10^6$ centipoise and about $5.0 \times 10^7$ centipoise. As used herein the term "zero shear viscosity" refers to a viscosity measured at very low shear rates (e.g., 1/sec) using plate and cone viscometer (a suitable instrument is available from TA Instruments of New Castle, Del. as model number CSL 100). One of skill in the art would recognize that using means other than high melting point components can be used to provide comparable viscosities. For example, the lotion could be provided with a structure which has a high zero shear viscosity but, on the application of shear, such structure collapses with a resulting viscosity reduction (Compositions of this type are said to have a yield value.) Such structure can be provided by certain clay materials, such as bentonite clays or montmorillonite clays, and by fumed silica. Particularly preferred are the fumed silicas as are available from the Cabot Corp., Cab-O-Sil Div. Of Tuscola, Ill. as CAB-O-SIL. A skilled person would also recognize that the zero shear viscosity of such compositions may be measured by extrapolating a plot of viscosity vs. shear rate to a shear rate of zero. Such viscosity measurements should be conducted at a temperature of about 20° C.

The skin care composition carrier vehicle may include a useful active ingredient such as one or more skin protectants or emollients. As used herein, the term "emollient" refers to a material that protects against wetness or irritation, softens, soothes, supples, coats, lubricates, moisturizes, protects and/ or cleanses the skin. (It will be recognized that several of the monographed actives listed above are "emollients", as that term is used herein.) In a preferred embodiment, emollients will have either a plastic or liquid consistency at ambient temperatures, i.e., about 20° C. Such a consistency allows the composition to impart a soft, lubricious, lotion-like feel.

Representative emollients useful in the present invention include, but are not limited to, emollients that are petroleum-based; sucrose ester fatty acids; polyethylene glycol and derivatives thereof; humectants; fatty acid ester type; alkyl ethoxylate type; fatty acid ester ethoxylates; fatty alcohol type; polysiloxane type; propylene glycol and derivatives thereof; glycerine and derivatives thereof, including glyceride, acetoglycerides, and ethoxylated glycerides of $C_{12}$—$C_{28}$ fatty acids; triethylene glycol and derivatives thereof, spermaceti or other waxes; fatty acids; fatty alcohol ethers, particularly those having from 12 to 28 carbon atoms in their fatty chain, such as stearic acid; propoxylated fatty alcohols; other fatty esters of polyhydroxy alcohols; lanolin and its derivatives; kaolin and its derivatives; any of the monographed skin care agents listed above; or mixtures of these emollients.

Another preferred component of the skin care composition carrier vehicles useful in the present invention is an agent capable of immobilizing the composition (including the preferred emollient and/or other skin conditioning, therapeutic or protective agents and/or the FMA(s) present in the composition) in the desired location in or on the treated article. The immobilizing agent may counteract the tendency of an emollient to migrate or flow by keeping the emollient primarily localized on the surface or in the region of the article to which the composition is applied. This is believed to be due, in part, to the fact that the immobilizing agent raises the melting point and/or viscosity of the composition above that of the emollient. Since the immobilizing agent is preferably miscible with the emollient (or solubilized in the emollient with the aid of an appropriate emulsifier or dispersed therein), it entraps the emollient on the surface of the article's wearer contacting surface or in the region to which it is applied.

It is also advantageous to "lock" the immobilizing agent on the wearer contacting surface or the region of the article to which it is applied. This can be accomplished by using immobilizing agents which quickly set up (i.e., solidify) upon application to the article. In addition, outside cooling of the treated article via blowers, fans, cold rolls, etc. can speed up crystallization of the immobilizing agent.

In addition to being miscible with (or solubilized in) the emollient, the immobilizing agent preferably hag a melting profile that provides a composition that is solid or semisolid at ambient temperature. In this regard, preferred immobilizing agents have a melting point of at least about 35° C. This prevents the immobilizing agent from having a tendency to migrate or flow. Preferred immobilizing agents will have melting points of at least about 40° C., and more typically in the range of from about 50° to about 150° C.

Immobilizing agents suitable for use in the present invention can be selected from any of a number of agents, so long as the preferred properties of the skin care composition provide the skin benefits described herein. Preferred immobilizing agents generally comprise a member selected from the group consisting of $C_{14}$–$C_{22}$ fatty alcohols, $C_{12}$–$C_{22}$ fatty acids, and $C_{12}$–$C_{22}$ fatty alcohol ethoxylates having an average degree of ethoxylation ranging from 2 to about 30, and mixtures thereof Preferred immobilizing agents include $C_{16}$–$C_{18}$ fatty alcohols, preferably crystalline high melting materials selected from the group consisting of cetyl alcohol, stearyl alcohol, behenyl alcohol, and mixtures thereof (The linear structure of these materials can speed up solidification on the treated absorbent article.) Other preferred immobilizing agents include $C_{16}$–$C_{18}$ fatty acids, preferably selected from the group consisting of palmitic acid, stearic acid, and mixtures thereof. Still other preferred immobilizing agents include $C_{16}$–$C_{18}$ fatty alcohol ethoxylates having an average degree of ethoxylation ranging from about 5 to about 20. Preferably, the fatty alcohols, fatty acids and fatty alcohols are linear. Importantly, these preferred immobilizing agents such as the $C_{16}$–$C_{18}$ fatty alcohols increase the rate of crystallization of the composition causing the composition to crystallize rapidly onto the surface of the substrate. Yet other types of ingredients suitable for use as immobilizing agents, either alone, or in combination with the above-mentioned immobilizing agents, include waxes such as carnauba, ozokerite, beeswax, candelilla, paraffin, ceresin, esparto, ouricuri, rezowax, isoparaffin, and other known mined and mineral waxes.

The Feces Modifying Agent may be delivered to the feces directly via transfer of the FMA to the feces or it may initially transfer to the wearer's skin or other element of the article prior to transfer to the feces. The carrier vehicle may be integral with the disposable article or may constitute, or be component of, a separate article to be applied to the wearer (preferably at least over the perianal region) prior to, or in place of, a diaper, training pant, underwear, or other article.

The means for joining the FMA to a carrier vehicle may include any means known in the art, such as adhesives (particularly water soluble adhesives), hydrogen bonding, releasable encapsulation, spraying, coating, and the like.

Hydrogen bonding of the FMA to a substrate may be effected by slightly wetting either the FMA or at least a portion of the substrate with water. Upon drying, the FMA is releasably affixed to the substrate (i.e., subsequent contact with liquid water will break the bond). This effect is enhanced for those FMAs which "gel" and become sticky when wet (e.g., CMC, hydroxy propyl cellulose, alginic acid and derivatives, etc.). Wetting may be accomplished by subjecting either the FMA, substrate, or both to a high humidity environment (e.g., 80% RH or greater) prior to or at the time of contact. Alternatively, water may be sprayed, misted, or atomized over at least a portion of either the agent or substrates prior to or at the time of their contact. In such cases, the structure is preferably dried prior to incorporation into an article.

The FMA may contact the feces at or near the surface of the article (e.g., at the topsheet/feces interface), within the article (as in a waste management element 120 as described below), or at the body-side surface of the fecal mass (i.e., having first been transferred to the skin or other surface above the plane of the article). Typically, the FMA will contact the feces in the region of the article associated with the wearer's anus (e.g., crotch region in a diaper context). The feces may alternatively contact the FMA as it passes through an orifice, flange, valve, or the like, at or near the anus of the wearer. In such cases, the FMA may be expressed or drawn from the orifice or valve (e.g., from reservoirs) by the pressure of the passage of the feces as it extrudes from the body. The orifice may comprise a slit, slot, or perforation in a sheet, envelope, packet or other structure containing the FMA or composition comprising a FMA disposed in proximity to the exit point of the feces from the body. The orifice may be initially sealed by soluble film that is dissolved by contact with the feces, releasing the agent or composition. Alternatively, the orifice may be opened as the structure is deformed by passage or pressure of the feces. The feces pressure, in addition to body pressure and movement may aid in the expression of FMA through the orifice to the feces.

In other preferred embodiments, the FMA may be associated with a gasket such as a leg cuff, waist barrier, waistband, waste pocket or with a feces spacing element. In embodiments wherein the FMA is associated with a gasketing element such as a leg cuff, waist barrier, or waist pocket, it is preferred that the FMA be associated with the portion of the gasket disposed closest to the exit point of the waste from the wearer (e.g., the anus for feces). In certain preferred embodiments, the FMA is releasably attached to the surface of the gasket material so as to promote treatment of the feces contacting the gasket. The FMA may be releasably attached to the gasket surface via any of the means described above or any other means known in the art. In other embodiments, the FMA is releasably encapsulated at or near at least a portion of the gasket surface. In embodiments including feces spacing elements, any portion of the spacing element may comprise one or more FMAs. The spacing element may be releasably coated with the agent as described above or may comprise cells, packets, or pouches of the agent covered, at least in part, with a water or feces-soluble film (as described above).

The FMA may be delivered passively (e.g., the feces flows and contacts it during normal wearing conditions), actively (e.g., an element in the article responds to a signal and delivers/releases the FMA to the feces), or via a secondary carrier (e.g., a powder or other skin care composition initially transferred to the wearer's skin). Delivery of the FMA to the feces may occur as a result of feces extrusion pressure, weight, temperature, enzyme activity, water content, and/or pH; urine presence (e.g., urine triggering release of the agent in response to or in anticipation of a defecation); body motions, pressure, or heat; or any other trigger or event during the wear cycle of the article.

The FMA may be initially stored within or on the article or any portion thereof and subsequently released by any of the triggering events described herein. In certain preferred embodiments, the FMA is releasably encapsulated under a film, in cells, packets, envelopes and the like so as to prevent migration and/or loss of the agent prior to the article being insulted by feces and/or to aid in positioning the FMA for contact with the feces during use. The film covering, cells, packets, or other "containers" for the agent may comprise a water-soluble film over at least the feces-contacting surface area of the container. The water from urine, feces, or other feces dissolves the film releasing the agent (i.e., triggering release) to contact and treat the feces. An example of a water soluble film useful in the present invention is a polyvinyl alcohol film available as MONOSOL M7031 from Chris Craft Industrial products of South Holland, Ill. or HL1636 from the H. B. Fuller Co. of St. Paul, Minn. Alternatively, the film may be soluble only in the presence of certain fecal enzymes (like trypsin) or in certain pH ranges.

The release of the agent may be rapid (such as with an explosive gas release created by contacting urine or fecal water with a gas-evolving composition) to embed or coat the feces with the agent. The gas evolving composition may comprise particles, globules, etc. of one or more substances which evolve gas when mixed with or together in water (e.g., sodium bicarbonate or sodium bicarbonate and citric acid). The particles may be embedded in a water soluble matrix (e.g., PVA). The FMA may be disposed on or attached to the waste contacting surface of the film or may be embedded in the water soluble film between the gas-evolving composition and the feces contacting surface. Thus, for example, when water present in the feces dissolves the water-soluble film, the gas-evolving composition is activated (i.e., the component(s) mix with the water) and gas is evolved rapidly, forcing mixing of the FMA and the feces. The particles may comprise combinations such as citric acid and sodium bicarbonate which, when mixed with water, rapidly releases carbon dioxide gas. Alternatively, the gas-evolving composition may comprise water soluble capsules containing compressed gas and the FMA. Water from the feces which contacts the capsules can act to dissolve the film and release the gas explosively, again forcing mixing/ embedding of the agent in the feces. Other compositions and gas-evolving or releasing systems are contemplated and are included in the scope of this invention, In certain preferred embodiments of the article of the present invention, the feces modification agent may be delivered to the feces or other waste, a carrier structure, or the wearer's skin or is mixed with at least a portion of the feces or other waste via a responsive system. A "responsive system" as used herein generally comprises at least one sensor 60 and at least one actuator 70 comprising stored energy. In this context, the actuator 70 effects delivery or transport of the feces modifying agent to the waste, carrier structure, or skin or mixing of the feces modifying agent with the waste upon the detection of a target input signal by the sensor 60. Alternatively, the responsive system may function to move a carrier structure (such as a web, brush structure, or other carrier structure described herein) or other element comprising a feces modifying agent into contact or proximity with the waste or the wearer's skin to facilitate the ultimate contact of the feces modifying agent with the bodily waste (e.g., feces). For example, the responsive system may force a brush structure comprising a feces modifying agent (for example, hydrogen bonded to the brush elements) to penetrate a fecal mass, promoting mixing of the feces modifying element with the feces.

Figure 4:
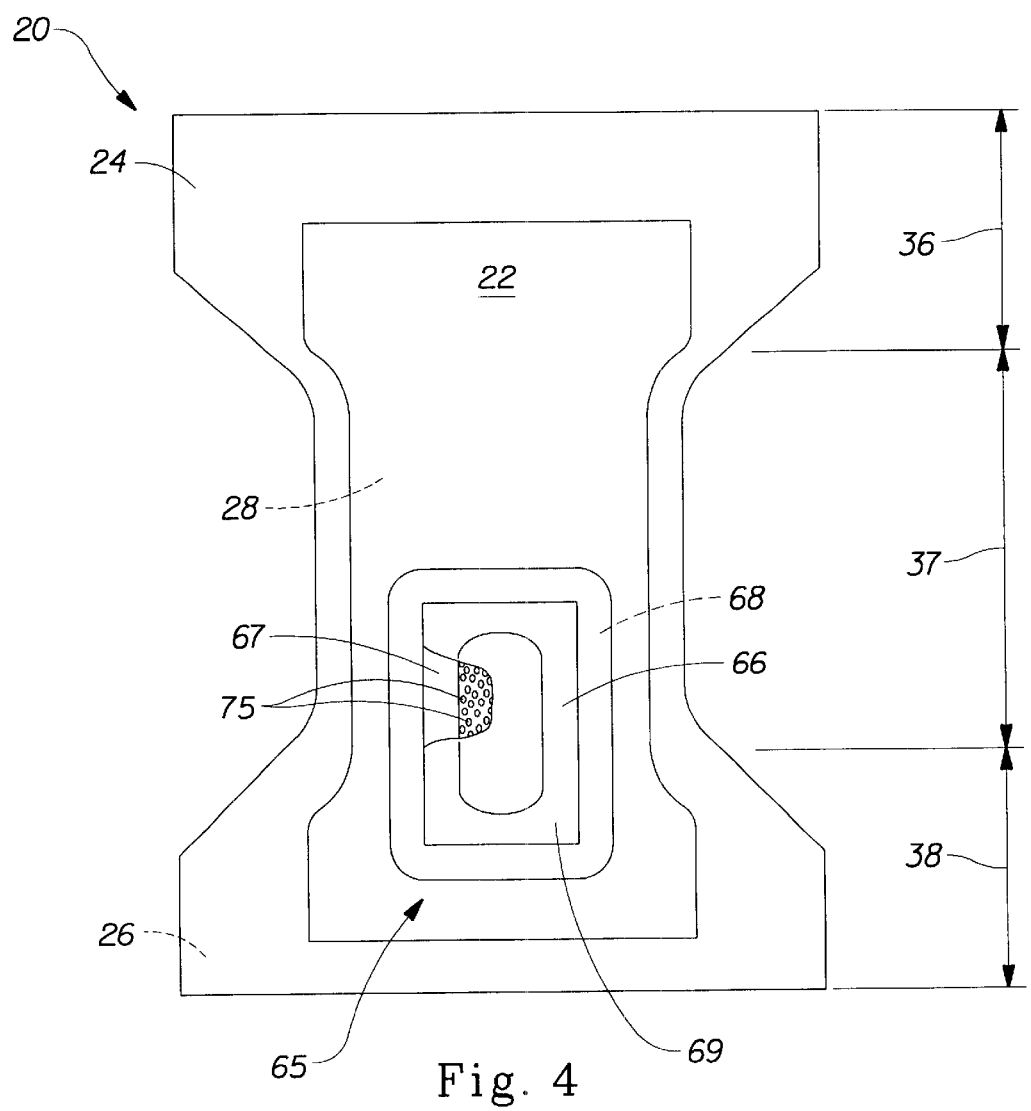
FIG. 4 is a plan view of an absorbent article embodiment of the present invention having portions cut away to reveal the underlying structure, the body-facing surface of the diaper facing the viewer.

One preferred embodiment comprises a shaped, compressed, macro-porous foam 68 held in compression under a water-soluble polyvinyl alcohol film as shown in FIG. 4. The foam 68 additionally comprises an FMA 75. Contact with fecal water results in dissolution of at least a portion of the PVA film resulting in a release of the stored mechanical energy in the foam 68 and mechanical transport of the FMA toward or into the fecal mass. In certain embodiments, mixing may occur via a mechanism incorporated in the article as described herein (e.g., responsive system), mechanical action from the wearer's weight and/or motion, and/or the flow of feces during or subsequent to the act of defecation (especially low viscosity feces) to facilitate treatment of a greater proportion of the fecal mass. Other responsive systems are described in detail in co-pending U.S. patent application Ser. No. 09/106,424 entitled "Disposable Article Having A Discontinuous Responsive System" (P&G Case 7197) filed in the names of Roe et al. on Jun. 29, 1998; which is hereby incorporated by reference herein.

As used in this application, the term "sensor" refers to a device that is capable of detecting an event or a parameter that is associated with an event. A parameter associated with an event is any measurable signal that correlates with the occurrence of an event within the frame of reference of the system (i.e., a signal caused by the waste, the wearer, or a component thereof). Sensors include anything that responds to one or more specific inputs. Examples of inputs that may be detected by the sensor of the present invention include, but are not limited to, attitude, pressure, motion, moisture, enzymes, bacteria, pH, conductivity, resistance, capacitance, inductance, or other chemical, biochemical, biological, mechanical or electrical properties and/or components of bodily wastes. The sensors preferably detect "non-environmental" inputs such as a non-thermal or a non-relative humidity input in order to minimize the number of false responses by minimizing the possibility of an environmental condition triggering the sensor instead of the sensor detecting an input caused by the waste, the wearer, or a component thereof. In one embodiment, the sensor may detect temperatures that are not close to the body temperature of the wearer. This allows the use of a temperature sensor, but still minimizes the possibility of the body temperature of the wearer triggering the sensor instead of the desired input. An electrical or biological sensor may, for example, detect an elimination of bodily waste event such as a defecation, urination or discharge of menses by sensing a component of the waste. A sensor may detect one or more events or one or more parameters associated with an event and provide an input to an actuator or a controller. Further, a sensor of the present invention may also be reversible or irreversible. A dissolving film or capsule is an example of an irreversible sensor, while an electrical sensor that detects electrical activity in muscles of the wearer may receive multiple sequential input signals (i.e., is reversible).

As discussed above, sensors 60 of the present invention may include anything that responds to a specific input. For example, the sensor 60 of the present invention may be chemical, mechanical, electrical, etc. A chemical sensor may respond to chemical and/or biochemical inputs such as enzymes typically present in bodily wastes, pH, water, biological inputs such as bacteria, blood or any one or more other components of bodily wastes such as feces, urine, or menses, etc. A chemical sensor may use a chemical reaction as a detection means or may involve a dissolution of a material soluble in an input material of interest. Examples of chemical or biological sensors include dissolving or rupturable films, capsules, cells, seals, etc. that dissolve or rupture in response to a specific chemical, biochemical or biological input or to a specific class of chemical, biochemical or biological inputs. A mechanical sensor may also respond to motion, attitude, pressure, etc. An example of a mechanical sensor is a bellows-type in which when a baby sits on the sensor the weight pushes down on the bellows to inflate a portion of the sensor. A mechanical sensor may also include a sensor or a portion of the sensor that is broken or separated under a pre-defined applied pressure. An electrical sensor may also be used to respond to moisture, urine, feces, menses, pressure, resistance, capacitance, inductance, etc. An electrical sensor may, for example, include a sensor in which a conductive input such as urine or feces completes an electrical circuit; a sensor in which an input such as pressure or tension closes an electrical contact to complete a circuit; a piezoelectric sensor that generates a signal via pressure induced by the wearer or a part of the wearer (e.g., from motion or muscle tone), a sensor in which the resistance, capacitance or inductance varies in the presence of the input to which the sensor responds; or a sensor that receives electrical signals from the body (e.g., from the subcutaneous muscles) of the wearer through a contact such as a skin contact sensor. A thermal sensor may also be used to detect changes in temperature. Optionally, the sensor may be a biosensor as known in the art (e.g., an enzyme sensor, organella sensor, tissue sensor, microorganism sensor, or electrochemical sensor). The sensor may be adapted to detect proteins, sugars, bile components, etc. such as described in U.S. Pat. No. 4,636,474 entitled "Toilet Apparatus," issued to Kenji Ogura et al. on Jan. 13, 1987. Biosensors may comprise bio-recognition systems, typically enzymes or binding proteins such as antibodies immobilized onto the surface of physico-chemical transducers. The biosensors may detect components of bodily wastes, such as ammonia and phenol (e.g., via biosensors comprising enzyme electrodes). A specific strain of bacteria may be detected via biosensors employing antibodies raised against that bacterial strain. Exemplary enzyme electrodes that may be used to detect phenols (e.g. in urine or feces) include tyrosinase based electrodes or polyphenol oxidase enzyme electrodes described in U.S. Pat. No. 5,676,820 entitled "Remote Electrochemical Sensor," issued to Joseph Wang et al. on Oct. 14, 1997 and U.S. Pat. No. 5,091,299 entitled "An Enzyme Electrode For Use In Organic Solvents," issued to Anthony P. F. Turner et al. on Feb. 25, 1992, respectively.

Optionally, the sensor 60 may be a "proactive sensor" that is capable of detecting changes or signals in or on the body of the wearer, in the article, or in the waste that directly relate or, at a minimum, correlate to the occurrence of an impending event such as a defecation, urination or other discharge of bodily waste. A proactive sensor, for example, may detect an impending event such as a defecation, urination or discharge or a parameter that correlates to such an event. The impending event may be related to the bodily waste, the wearer, the article, or a component or components thereof. A parameter that correlates to an event is any measurable input signal that correlates with the occurrence of the event within the frame of reference of the system (i.e., a signal caused by the waste or the wearer). The proactive sensor may, for example, predict the occurrence of a defecation, urination or discharge of bodily waste or may detect signals that may precede skin rash or irritation.

Proactive sensors in an article may measure many different inputs in order to predict an event. For example, the proactive sensor may monitor the external anal sphincter muscle for a relaxation in the anal sphincter that precedes the release of feces and/or urine, a separation of the buttocks, a pressure change in the abdomen, a gas concentration in the article, or any other indication that may be used to predict or anticipate the occurrence of an event such as a defecation, a urination or a discharge of bodily wastes. Alternatively, a proactive sensor of the present invention may detect signals that precede skin irritation. For example, the sensor may detect residual fecal contamination of the wearer's skin (e.g., fecal enzyme residue left after cleaning up a soiled diaper) that may, over time, lead to irritated skin. Detection of a high pH, an increased skin hydration resulting in a measurable increase in conductance or decrease in impedance of skin, etc. may also be used to predict potential skin irritation. Further embodiments of a proactive sensor are described in copending U.S. application Ser. No. 09/107,561 entitled "Disposable Article Having A Proactive Sensor" (P&G Case No. 7196) filed on Jun. 29, 1998, which is herein incorporated by reference.

The sensor 60 may be disposed in and/or operatively connected to any portion of a disposable article that will be exposed to the input that the sensor is designed to detect. For the purposes of the present invention, the term "operatively connected" refers to a means of communication such that the sensor 60 may signal some portion of the article 20 when the sensor 60 detects an input. The sensor 60 may be separate from and operatively connected to another portion of the sensor 60, another sensor 60, an actuator 70, a controller 80 or some other portion or component of the article 20. "Operatively connected" may, for example, include a means of communication such as an electrical connection via a conductive wire or member, via a transmitted signal such as radio frequency, infrared or another transmitted frequency communication. Alternatively, the sensor 60 may be operatively connected via a mechanical connection such as a pneumatic or a hydraulic connection.

In article 20, for example, the sensor 60 may be located in the front waist region 36, the rear waist region 38 or the crotch region 37 of article 20, and may be integral with, disposed adjacent to, joined to, or comprise a portion of the chassis 22, the topsheet 24, the backsheet 26, the absorbent core 28, side panels 30, leg cuffs 32, a waist feature 34, a fastening system 40, the longitudinal 50 or end 52 edges, etc. The sensor 60 may be integral with the article 20, or may be installed by the caretaker or the wearer. The sensor 60 may be completely contained within the article such as article 20 or may have a receiving portion located in the article such that it will come into contact with the desired input and another portion such as a transmitting portion located either in the article or outside the article. The sensor 60 may be external to the article 20 yet operatively connected to some portion of the article 20 such that the sensor 60 may detect an input external to the article 20 and provide a signal to a controller 80 and/or an actuator 70. In some embodiments, the sensor may be separate from the article, e.g., separately applied to some portion of the wearer, and/or may have one or more component separate from the article.

The sensor 60 may further comprise a sensing "system" including two or more sensors, each of which may detect the same or different signals from the same or different sources. The sensing system may include components that are located inside, external to and/or separate from the article. For example, the sensing system may include a sensor inside the article that detects electrical signals in the external anal sphincter of the wearer and a sensor external to the article that detects motion, tension or muscle activity in the abdomen of the wearer. The sensing system may also or alternatively include components other than the sensing elements inside, external to and/or separate from the article. The sensing system, for example, may include a transmitter that is external to the article and transmits a signal to another part of the sensing system that is joined to or disposed in the article 20.

The article 20 preferably also comprises at least one actuator 70. As used in this application, the term "actuator" refers to a device that comprises "potential" and a means of transforming that potential to perform or activate a "responsive function." The potential of the actuator 70 may comprise either stored or potential energy or stored material. The actuator 70 thus may perform or activate a responsive function by transforming potential energy to kinetic energy or by releasing or delivering a stored material. A "responsive function" is defined for the purposes of this application as a function performed upon the bodily waste, the wearer, the article, or a component thereof For the purposes of the present invention, a function is considered to be performed upon the input if the function is performed upon the element sensed, e.g., sensing feces and action upon the feces, or if the function is performed upon a composition of which the element sensed is an integral component, e.g., sensing a fecal enzyme or fecal moisture and action upon feces. A device that merely provides a signal indicating that an event has occurred, however, is not considered an "actuator" as defined for the purposes of this application. A component of bodily waste may include, for example, moisture, electrolytes, enzymes, volatile gases, bacteria, blood, etc. A component of the wearer may also include skin, genitalia, the anus, the anal sphincter muscle, etc. A component of the article may also include leg cuffs, waist cuffs or other waste barriers and/or containment components, side panels, ears, a chassis, an absorbent core, an acquisition component, a fastening system, the longitudinal or end edges, etc. Potential energy may be stored as mechanical, electrical, chemical or thermal energy. "Kinetic energy" as used in this application refers to the capacity to do work or to perform a responsive function, or combination of functions, as described above (e.g., expansion of a compressed device, rotation of a twisted device, a gel that moves as it changes phases, coating or treatment of skin or feces (for example, with a feces modifying agent), inhibition of an enzyme, adjustment of pH, etc., and combinations thereof).

Triggering the creation of a three dimensional structure to treat waste with a feces modifying agent or to capture waste, for example, involves responsive functions performed on a component of the article and, ultimately, on the waste. Treating waste (i.e., delivering a feces modifying agent thereto or mixing therewith), capturing waste, wiping the skin of the wearer or treating the skin with a skin care composition, for example, are responsive functions performed on the waste and/or the wearer. Adjusting the article's geometry (in one, two or three dimensions) or physical properties (e.g., bending modulus, geometry, etc.) are examples of responsive functions, which may be performed on the article. An actuator of a disposable article may, for example, release, deliver, and/or mix a feces modifying agent, deodorant, enzyme inhibitor, skin care composition or pH control agent; capture, wipe, cover, trap, immobilize, seal, pump, or store bodily waste; or trigger the release or creation of a structure or element designed to perform one or more of these functions or any other responsive function upon the waste, wearer, article, or a component thereof. Any mechanical action occurring as a result of the release of potential energy in the system may be used to deliver a feces modifying agent to the feces or other waste, a carrier structure, or the skin of the wearer or to mix the feces modifying agent with at least a portion of the feces or other waste.

An actuator 70 may be triggered by a threshold level of an input to release potential energy to perform a responsive function or may respond continuously to an input as described below. For example, a compressed foam has stored compressive mechanical potential energy and may provide mechanical kinetic energy when it is released. A twisted foam has stored torsional mechanical potential energy that may provide mechanical kinetic energy, i.e., rotation, when it is released. In addition, stored chemical, electrical or thermal energy may be used to release electrical, mechanical, chemical or thermal kinetic energy. An actuator of a disposable article, for example, may include one or more of the following: stored feces modifying agents, lotion, enzyme inhibitors, pH buffers, dyes, pressurized gag, a compressed foam, a twisted foam, a pump, a closed system liquid transport member, an electrically sensitive gel, a pH sensitive gel, a salt concentration gel, etc.

Potential energy may be stored in any manner sufficient to maintain/restrain it until it is required. Examples include batteries and/or capacitors, elastically, torsionally, compressively tensioned materials or structures, in the form of unreacted reagents, and materials capable of performing physical or chemical functions (e.g., absorbents, emollients, pH buffers, enzyme inhibitors, feces modification agents; compressed gases, etc.).

In alternative embodiments the sensor and/or actuator may comprise a closed system liquid transport member. A "closed system liquid transport member" or "transport member" comprises a liquid filled member having an inlet port and outlet port, which upon receipt of even a little amount of liquid at the inlet port practically immediately releases liquid at the outlet port. The liquid released from the outlet port may serve as an input signal to a sensor. For example, the liquid may be water, which is released when the transport member imbibes urine at an inlet port, which acts to dissolve a seal to release stored mechanical energy to create a feces void space. Alternatively, the transport member may itself trigger an actuator (e.g., mix with agents to perform a chemical reaction), or may perform at least a portion of the actuator function (e.g., the released water is imbibed by a super absorbent polymer arranged in a particular geometry, which swells and forms a feces void volume). Liquid transport through such transport members is based upon direct suction rather than on capillarity. The liquid is transported through a region into which no significant quantity of air (or other gas) may enter. The driving force for liquid flowing through such a member can be created by a liquid sink (e.g., a capillary or osmotic absorbent structure) or source in liquid connection with the member. Thus, a liquid transport member must have a relatively high liquid permeability There are preferably at least two regions within the transport member with different pore sizes, namely the one or more port region(s) having smaller pores and the inner region having a much larger pore size. The inner region of the transport member has a permeability that is relatively high compared to the permeability of a port region (a higher liquid permeability provides less flow resistance), which can be a part of an outer/wall region circumscribing the inner/ bulk region. Nonlimiting examples of high porosity materials suitable for use as the inner region material include fibrous structures comprising polyolefin, PET, cellulose, and cellulose-based fibers, and porous, open celled foam such as reticulated foams, cellulose sponges, polyurethane foams, and HIPE foams. In one embodiment, the voids of the inner region are essentially completely filled with an essentially incompressible fluid. The term "essentially completely" refers to the situation, where sufficient void volume of the inner region is filled with the liquid such that a continuous flow path between inlet and outlet ports can be established.

The port regions of the transport member comprise materials which are permeable for the transport liquid, but not for the ambient gas (like air) once they are wetted with the transport liquid. Often, such materials are described as membranes, which are defined as regions that are permeable for liquid, gas or a suspension of particles in a liquid or gas. The membrane may for example comprise a microporous region to provide liquid permeability through the capillaries. In an alternative embodiment, the membrane may comprise a monolithic region comprising a block-copolymer through which the liquid is transported via diffusion. Exemplary membranes for the port regions include celluloseacetate membranes, such as also disclosed in U.S. Pat. No. 5,108, 383 entitled "Membranes for Absorbent Articles" issued to White on Apr. 28, 1992, PET films as disclosed in EP-A-0451797, nitrocellulose membranes, cellulosenitrate membranes, PTFE membranes, polyamide membranes, and polyester. Other suitable materials are woven polymeric meshes, such as polyamide or polyethylene meshes as available from Verseidag in Geldern-Waldbeck, Germany, or SEFAR in Rüschlikon, Switzerland.

Figure 7A:
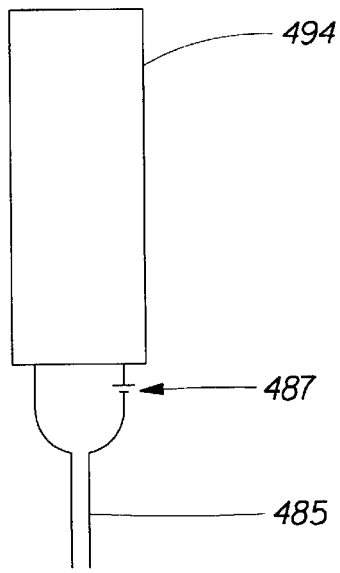
FIGS. 7A and 7B show an embodiment of a responsive system of the present invention including an electrically sensitive gel.
Figure 7B:
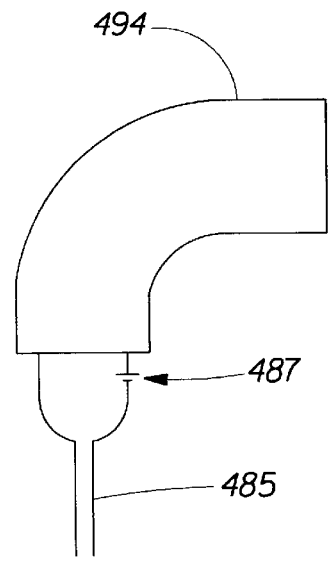
Figure 8A:
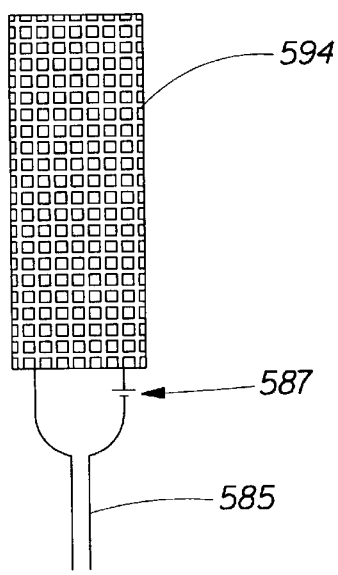
FIGS. 8A, 8B and 8C shown another embodiment of a responsive system of the present invention including an electrically sensitive gel.
Figure 8B:
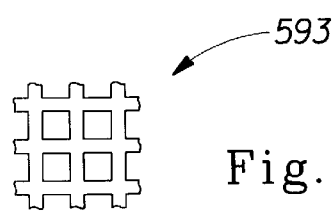
Figure 8C:
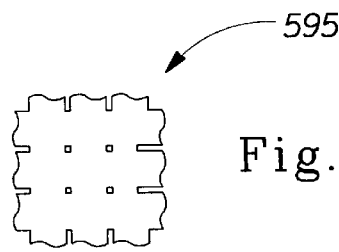

The actuator 70 may alternatively comprise an electrically sensitive gel. Electrically sensitive gels are polymeric gel networks that, when at least partially swollen with water, change volume and/or geometry under the application of an electric current or field. For example, certain partially ionized polyacrylamide gels will undergo anisotropic contraction of about 50% under weak electric fields (e.g., 0.5 volts/cm) when immersed in acetone and water. Alternative electrically sensitive gels may undergo electrically induced bending in the presence of water and a surfactant or may undergo an oscillating wave motion when subjected to an oscillating electric field. It is believed that local shrinkage may be induced in a portion of the gel, e.g., one side of a gel element, by concentrating positively charged surfactant molecules on the negatively charged gel polymer in an electric field. Changing the intensity and/or the polarity of the field induces a movement in the gel as one side decreases in length (e.g., a gel formed in a strip may curl). Electrically sensitive gels may comprise variable geometries such as rectangular, circular, reticulated grid, etc. patterns in order to provide a valve to release a material, allow a bodily waste to flow through, prevent a bodily waste from flowing through, encapsulate a bodily waste, etc. as they change volume and/or geometry. An electrically sensitive gel formed in a strip, for example, may be bent to transport feces when fecal moisture is detected. In FIGS. 7A and 7B, for example, a strip of electrically sensitive gel is shown in a circuit in which fecal moisture may bridge the contacts 485 and allow current to flow to the electrically sensitive gel either bending or straightening the strip. Alternatively, an electrically sensitive gel formed in a reticulated grid pattern, such as shown in FIGS. 8A, 8B and 8C, may be electrically induced to swell or shrink when urine is detected to form a valve that allows and/or prevents urine flow to another portion of the article 20. FIG. 8A, for example, shows a circuit including a reticulated grid pattern of an electrically sensitive gel. FIGS. 8B and 8C further show a microscopic view of the grid in a shrunk and in a swelled configuration, respectively. An exemplary material is a weakly cross-linked PAMPs gel (poly(acrylamido-2-methyl propane) sulphonic acid). This type of gel may perform various functions such as the creation of a void space for feces, wiping the skin, applying or delivering a chemical feces treatment agent, or functioning as a valve to release a material. Other exemplary electrically sensitive gels are described in U.S. Pat. No. 5,100,933 issued to Tanaka on Mar. 31, 1990 and WO 9202005. Alternatively, pH sensitive gels or salt concentration sensitive gels that change volume and/or geometry at specific pH or salt concentrations, respectively, may be used as an actuator of the present invention.

The actuator 70 may be disposed in and/or operatively connected to any portion of disposable article that will allow the actuator to perform a responsive function upon the bodily waste, the wearer, the article, or a component thereof In article 20, for example, the actuator 70 may be located in the front waist region 36, the rear waist region 38 or the crotch region 37 of article 20, and may be integral with, disposed adjacent to or joined to a component of the chassis 22, the topsheet 24, the backsheet 26, the absorbent core 28, side panels 30, leg cuffs 32, a waist feature 34, a fastening system 40, the longitudinal 50 or end 52 edges, etc. The actuator 70 may also be completely contained within the article such as article 20, may have a portion located in the article and a portion located outside the article 20, or may be completely external to the article 20. An actuator 70 or a portion of an actuator 70 may be operatively connected to one or more sensors 60, one or more controllers 80, another portion of the actuator 70 or another portion of the article 20. Further, the actuator 70 may be integral with the article 20, or may be installed by the caretaker or the wearer.

The article 20 may also include a controller 80. A "controller" is defined for the purposes of this application as a device that receives an input from a sensor and determines if one or more actions are to be taken. The controller may receive a signal from the sensor 60 and direct the actuator 70 to perform a responsive function upon the bodily waste, the wearer, the article or a component thereof Alternatively, the actuator 70 may receive the signal directly from the sensor 60 and perform a responsive function upon the wearer, the waste, the article or a component thereof A controller may include materials that undergo chemical or physical change, may be a chemical, mechanical or electrical device that processes information from a sensor, etc. For example, in an article having a compressed plastic foam material encapsulated and restrained under vacuum by a moisture soluble bag, the sensor 60 may comprise the moisture soluble bag. The physical and chemical characteristics of the film, i.e., the type of polymer, the thickness, etc., that determine how much of the input must be present before the film will dissolve act as the controller 80 and determine the threshold level of input that must be met before the controller 80 allows the actuator 70 to release stored energy to perform a responsive function. The actuator 70 is the combination of the compressed foam and the loss of vacuum, which allows release of the stored mechanical energy of the compressed foam. In this example, the controller 80 acts as a one-time switch. An electrical controller 80 that receives signals from the sensor 60 such as electrical activity of muscles of the wearer, however, may receive and monitor multiple electrical signals and may repeatedly trigger the actuator. The controller may be integral with the sensor component, integral with the actuator component, or a separate component of the system.

The controller 80 may be disposed in and/or operatively connected to any portion of a disposable article that will allow the controller 80 to receive a signal from the sensor 60 and to provide a signal to the actuator 70. In article 20, for example, the controller 80 may be located in the front waist region 36, the rear waist region 38 or the crotch region 37 of article 20, and may be integral with, disposed adjacent to or joined to the chassis 22, or a component of the topsheet 24, the backsheet 26, the absorbent core 28, side panels 30, leg cuffs 32, a waist feature 34, a fastening system 40, the longitudinal 50 or end 52 edges, etc. The controller 80 may be integral with the article 20, or may be installed by the caretaker or the wearer. The controller 80 may be completely contained within the article such as article 20, may have a portion located in the article and a portion located outside the article, or may be located completely outside the article 20. A controller 80 or a portion of a controller 80 may be operatively connected to one or more sensors 60, one or more actuators 70, another portion of the controller 80 or another portion of the article 20. The controller 80, for example, may receive a signal from the sensor 60 and provide a signal to the actuator 70, e.g., by a radio frequency (rf) transmission.

Although distinct structural elements may perform the sensor 60, actuator 70 and controller 80 functions, the sensor 60, actuator 70 and/or controller 80 functions of the present invention need not be performed by distinct structural elements. The sensor 60 and controller 80 functions, for example, may be performed by the same structural element such as a film that dissolves in contact with a component of a bodily waste. In this example, the film acts as a sensor and responds to the input component of bodily waste. The physical and chemical characteristics of the film, i.e., the type of polymer, the thickness, etc., that determine how much of the input must be present before the film will dissolve act as the controller and determine the threshold level of input that must be met before the controller allows the actuator to release stored energy to perform a responsive function.

The article 20 of the present invention preferably includes a discontinuous responsive system with or without a feedback control loop. However, the responsive system may alternatively include a continuous responsive system having a feedback control loop. For example, an absorbent article may comprise a responsive system that acts upon the bodily waste when the article is soiled by the wearer. A "responsive system" is defined for the purposes of this application as a system that includes a sensor 60 and an actuator 70 that acts upon the bodily waste, the wearer, the article, or a component thereof when the sensor 60 detects the appropriate triggering input. Upon sensing a given input parameter, the actuator 70 effects the release of stored energy or material to perform a responsive function, i.e., acting upon the bodily waste, the wearer, the article, or a component thereof The responsive system of the present invention may respond in either a "continuous" or a "discontinuous" manner. As used in this application, a "continuous responsive system" refers to a responsive system in which the output is quantitatively dependent upon the quantity of the input, i.e., continuously increasing quantities of the input are required to effect continuously increasing quantities of the output, or where the output of the responsive system comprises a passive release of a stored material. A super absorbent polymer placed in an absorbent core of an article, for example, provides a continuous response in which the output is quantitatively dependent upon the quantity of the input, i.e., as increasing quantities of liquid waste contact the super absorbent polymer, an increasing amount of the polymer contains that liquid until the capacity of the polymer is exhausted. A stoichiometric chemical reaction is another example of a system having a continuous response to increasing output. In the reaction A+excess B→C, for example, the amount of excess B converted to C is stoichiometrically and, therefore "continuously," related to the amount of A available in the system. A responsive system that passively releases a stored material, however, generally provides a continuous response regardless of how the material itself is released because the actual responsive function performed upon the bodily waste, the wearer, the article, or a component thereof is performed by the material, not by the release of the material Thus, whether the material is released continuously in response to a given input, or released discontinuously at a single time when a threshold of a given input is detected, the responsive function performed by the released material is performed such that continuously increasing quantities of the input are required to effect continuously increasing quantities of the output until the material released is exhausted.

Figure 9A:
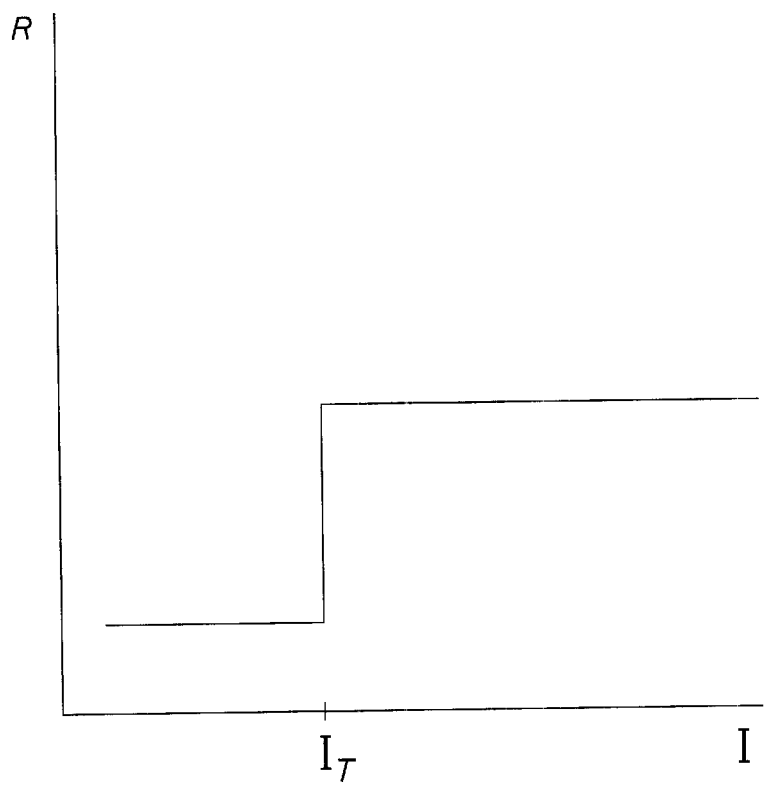
FIG. 9A shows an ideal output function of a discontinuous responsive system of the present invention having a single threshold level.

A "discontinuous responsive system," however, refers to a responsive system that has an output function that is essentially independent of the quantity of the input beyond a threshold level. For example, when one or more threshold levels of a given input are met, the responsive system may release all or a pre-designated portion of its stored energy to perform a specific responsive function. In an ideal embodiment of the present invention, the output function includes a "step" function as shown in FIG. 9A. In this embodiment, the rate of change in the output with increasing levels of input (d(output)/d(input)), i.e., the slope or first derivative f'(x) of the output function f(x), is preferably essentially zero when the amount of input is above or below the threshold level. At the threshold level, however, the d(output)/ d(input) rate of change preferably approaches infinity. Thus, in the ideal discontinuous response, the limit of the function $f(x-\epsilon)$ as $\epsilon \to 0$ is not equal to the limit of the function $f(x+\epsilon)$ as $\epsilon \to 0$, i.e., lim $f(x-\epsilon) \neq$ lim $f(x+\epsilon)$.

$$\epsilon \to 0 \quad \epsilon \to 0$$

Figure 10A:
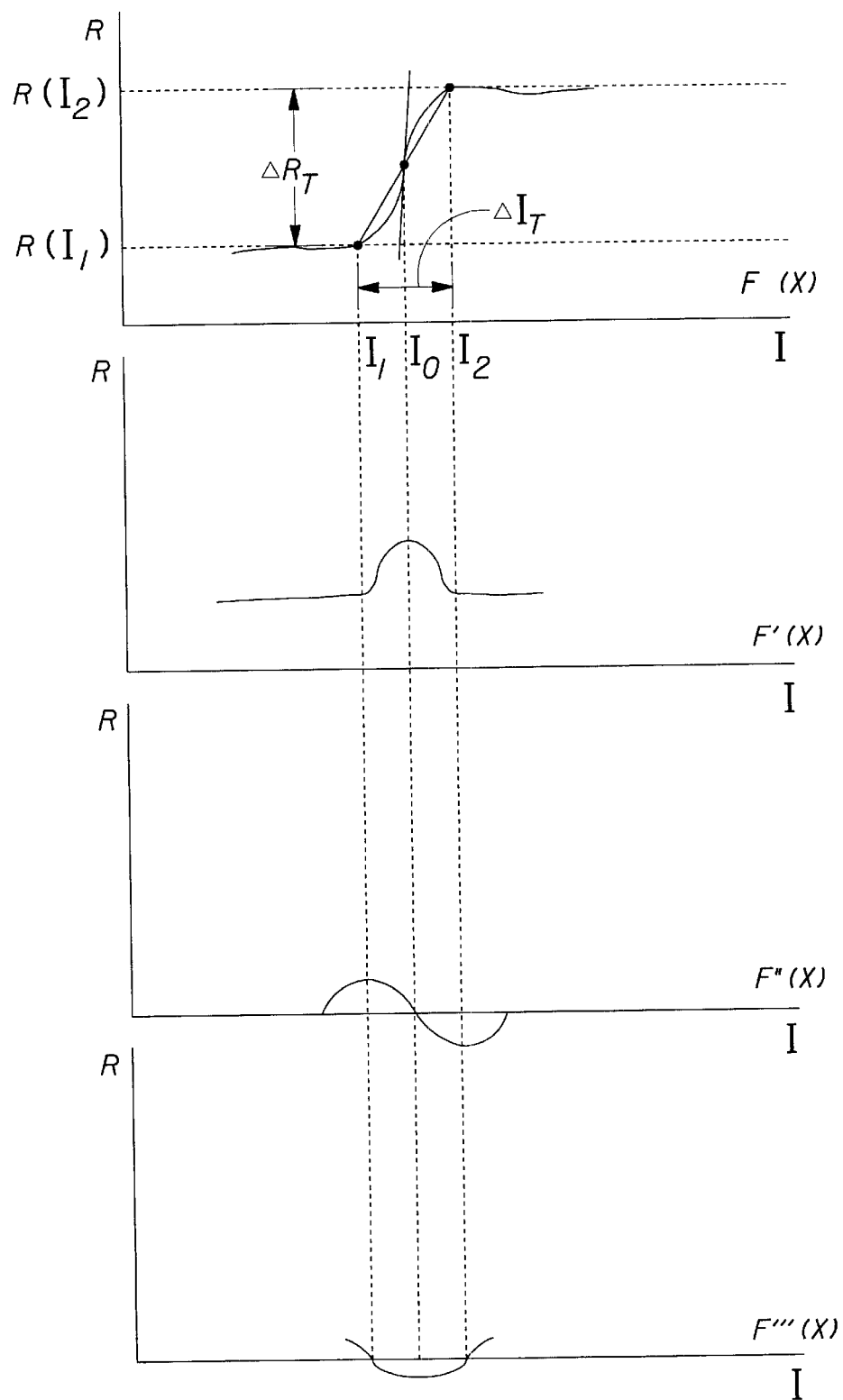
FIG. 10A shows an exemplary output function of a discontinuous responsive system of the present invention along with the first, second and third derivatives of the output function.

The present invention, however, recognizes that in the physical world an ideal instantaneous step change at the threshold level is not necessary and may not even be possible in many instances. In a preferred embodiment, it is only necessary that the output function have a virtual step change with very little change in the input at or around the threshold level of the input. Thus, the present invention contemplates a discontinuous responsive system of the present invention having an output function that responds in a sufficiently discontinuous manner in the transition region such that the output function has at least a minimum relative degree of steepness in the transition region. While not wishing to be limited to a particular method of describing or modeling a discontinuous system, in a preferred method of determining whether a given output function performs in a sufficiently discontinuous manner as defined for the purposes of the present invention, the slope of the output curve at the inflection point is compared with the relative slope of a line between the first and last points of the transition region. For example, FIG. 10A shows a graph of an exemplary output function, f(x) along with aligned graphs of the first, f'(x), and second, f'(x), and third, f'''(x), derivatives of the exemplary output function. The output function f(x) describes the effect of the input (x or I) on the output or response (R(I)). For purposes of the present invention, the transition region is defined as the region between the relative maxima, $R(I_1)$, and the minima, $R(I_2)$, of the second derivative, f'(x), of the output function, f(x). The relative maxima, $R(I_1)$, and the relative minima, $R(I_2)$, are points at which the third derivative, f'''(x), equals zero. The inflection point, $I_0$, is defined as the point in the transition region at which the second derivative, f'(x), equals zero, i.e., $$\left. \frac{d^2 R}{d I^2} \right|_{I=I_0} = 0.$$

The comparison of the slope of the output function at the inflection point to the slope of a line between the first and the last points of the transition region can be described by the equation:

$$\left. \frac{dR}{dI} \right|_{I=I_0} = k \frac{(\Delta R_T)}{(\Delta I_T)}.$$

In this equation dR/dI at the inflection point is the first derivative of the output function at that point. The term $\Delta I_T$ is the change in the input to the responsive system between the first, $I_1$, and last, $I_2$, points of the transition region, i.e., $I_2-I_1$, and the term $\Delta R_T$ is the change in the response of the output function between the first and last points of the transition region, i.e., $R(I_2)-R(I_2)$. The coefficient k is a proportional constant that describes the relative steepness of the slope of the output function at the inflection point, $I_0$, compared to the slope of a line between the first and last points of the transition region. In order that the responsive system have a discontinuous output function, the proportional constant k must be at least about 2.0, preferably at least about 3.0, more preferably at least about 5.0, even more preferably at least about 10.0, with at least about 100 being the most preferred.

Figure 10B:
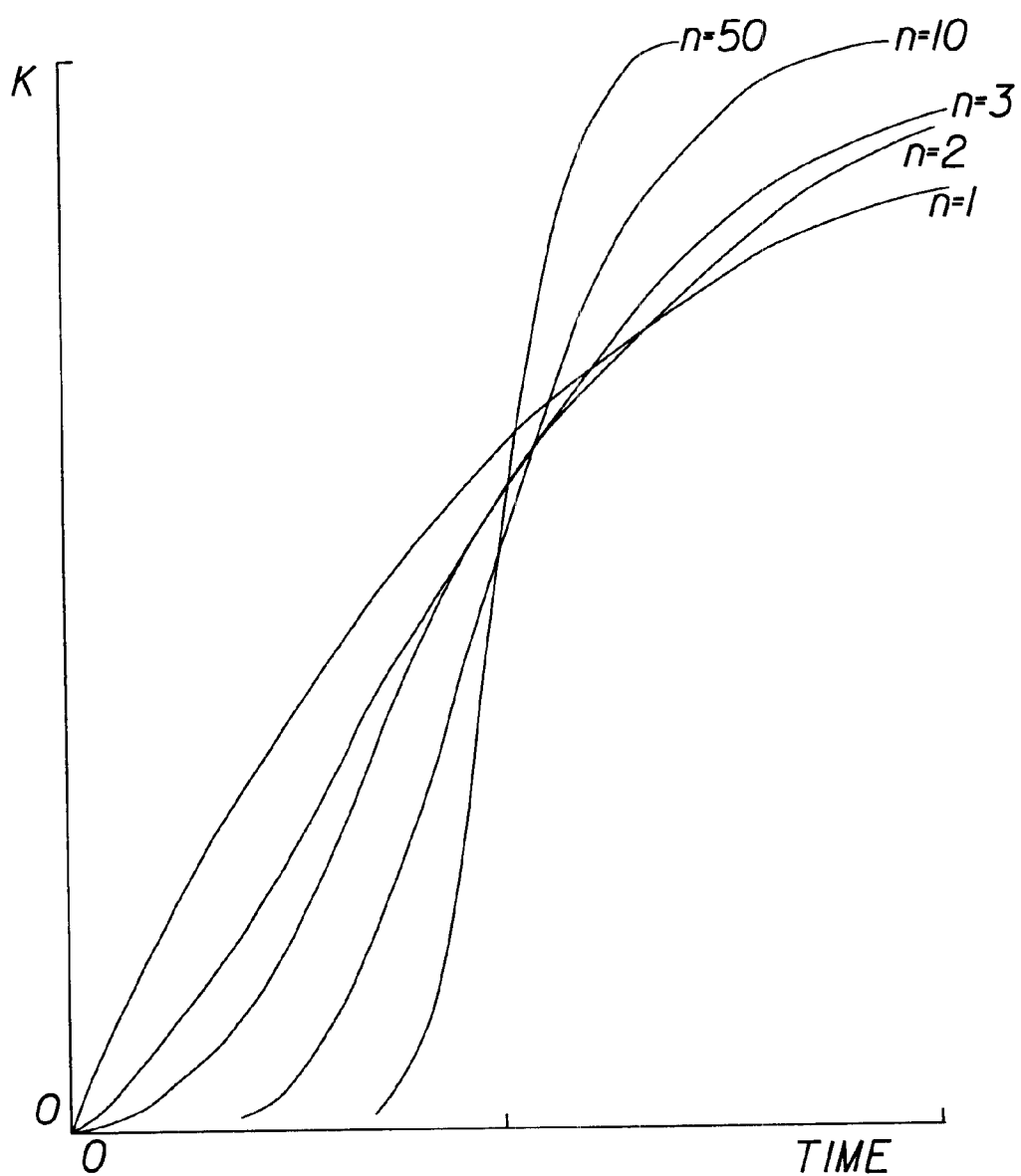
FIG. 10B shows a transfer function of a control system having a series of first order lags having an equal time constant.

In certain embodiments, the relative degree of steepness in the transition region of a discontinuous responsive system may also be modeled by a transfer function of a control system having a series of an integer number, n, first order lags with an equal time constant. The transfer function of the responsive system is defined for the purposes of the present invention as the ratio of the Laplace transforms of the output (responding variable) to the input (disturbing variable). See, e.g., Robert H. Perry & Don Green, *Perry's Chemical Engineers' Handbook,* Sixth Ed., Chap. 22 (McGraw Hill, Inc. 1984). As shown in FIG. 10B, the relative degree of steepness of an output function may be approximated by the formula: $KG(s)=K/(Ts+1)^n$ in which KG(s) is the transfer function, K is a proportional element, T is the time constant of the system, and n is the integer number of first order time lags. In this model, as the number n increases, the steepness of the output function in the transition region increases, and the model begins to approximate a discontinuous responsive system. Certain discontinuous responsive systems of the present invention preferably may be modeled by the above formula when n is greater than or equal to about 25, with n being greater than or equal to about 50 being more preferred, and n being greater than or equal to about 100 being the most preferred.

As shown in FIG. 9A, a responsive system of the present invention may include a single threshold level at which the responsive system may release all of its stored energy to perform a specific responsive function or may include multiple threshold levels at which the system may release a pre-designated portion of its stored energy to perform one or more specific responsive functions at each of the threshold levels. In an embodiment having a single threshold level, for example, the responsive system may release all of its stored energy to perform the entire responsive function when that threshold level is met. In such a single threshold embodiment, In this example, the discontinuous responsive system includes a system that has two states such as on or off When a threshold quantity of an input such as bodily waste is present in the absorbent article, the responsive system may perform a single responsive function upon the waste, the wearer, the article or a component thereof, such as enveloping the waste away from the skin of the user. Thus, the discontinuous responsive system may perform a one-time "switch-like" function that changes from one state to another in the presence of a threshold level of an input.

Figure 9B:
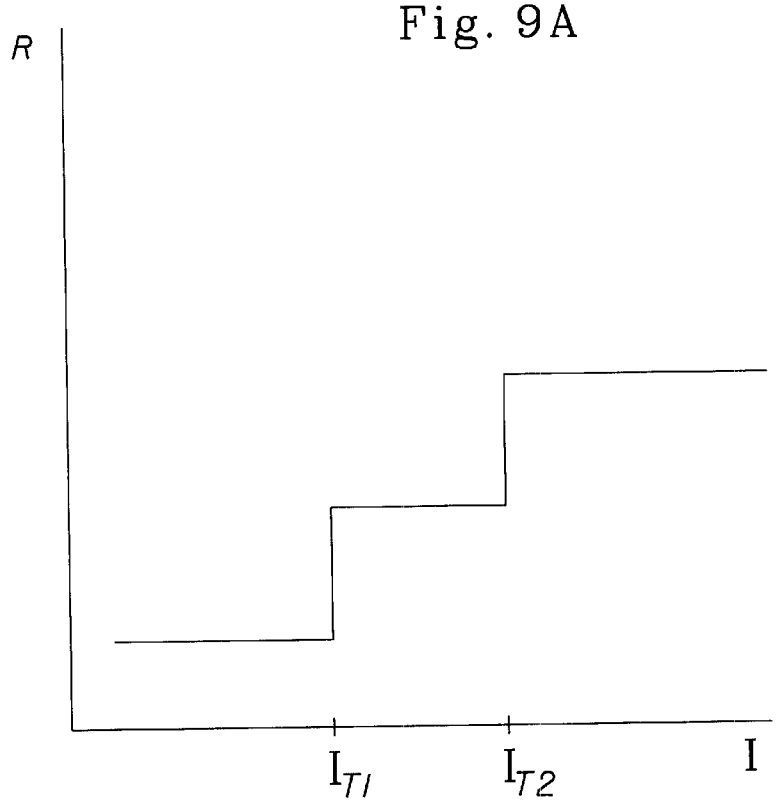
FIG. 9B shown an ideal output function of a discontinuous responsive system of the present invention having multiple threshold levels.

Alternatively, as shown in FIG. 9B, the responsive system may have multiple threshold levels at which when each threshold level is met the system may release a given "quanta" of energy or deliver a quantity of material to perform a specific responsive function. In this embodiment, when each threshold level is met, a portion of the entire responsive function may be performed and/or different independent responsive functions may be performed in response to different threshold levels being met. For example, a responsive system may monitor a fecal enzyme and when each threshold enzyme level is met may deliver an equal or unequal quantity of enzyme inhibitor(s), or may inflate or expand a storage component of the article or deliver a pH buffer at the first threshold level and perform another responsive function such as delivering a quantity of enzyme inhibitor(s) at the second threshold level. In each transition region, the responsive system responds essentially the same as the transition region in the single threshold embodiment described above.

The responsive system may also comprise a "closed loop" or an "open loop" system. A "closed loop" system, which is also referred to as a "feedback control loop" system, includes distinct sensor 60 and actuator 70 components and performs a responsive function upon the input. In some preferred embodiments, the system may also use a detection or a measurement of an element or a parameter of the output condition as at least one trigger of the responsive function that is performed upon the input. The output condition may be the state of the input condition after the actuator 70 has had the opportunity to perform a responsive function on the input condition. As described above, a feedback control loop system includes at least two distinct components: the sensor 60 and the actuator 70. The sensor 60 detects an event, or a parameter associated with that event. The actuator 70 receives a signal and performs a responsive function on the input condition detected by the sensor 60. The feedback control loop may further include a controller 80. In this case, the sensor 60 may provide a signal to the controller 80, and the controller 80 may direct the actuator 70 to perform a responsive function upon the input condition. The controller 80 may be a separate component of the responsive system or the controller function may be performed by the sensor 60 and/or the actuator 70.

An "open loop" system, however, is a system that responds to the input to perform a responsive function without using feedback, i.e., the output has no effect upon the sensed input entering the system. An open loop system may include a responsive system that has a single device that performs the functions of both the sensor 60 and the actuator 70 or may have distinct sensor 60 and actuator 70 components in which the actuator acts upon something other than the input. A super absorbent polymer placed in an absorbent core of a disposable absorbent article, for example, provides an open loop response because the polymer only includes a single device that performs the functions of the sensor 60 and actuator 70. Alternatively, an open loop responsive system may include a sensor 60 that detects bodily waste or a component of that bodily waste, and an actuator 70 that performs a responsive function in a continuous or a discontinuous manner on something other than the input detected by the sensor 60.

The present invention preferably includes a responsive system that provides a discontinuous response, whether open loop or closed loop. The present invention preferably also includes a responsive system that provides a continuous response and also include a feedback control loop (i.e., a closed loop system). Each of these types of responsive systems provide distinct advantages over the continuous open loop responsive systems known in the art.

Figure 13:
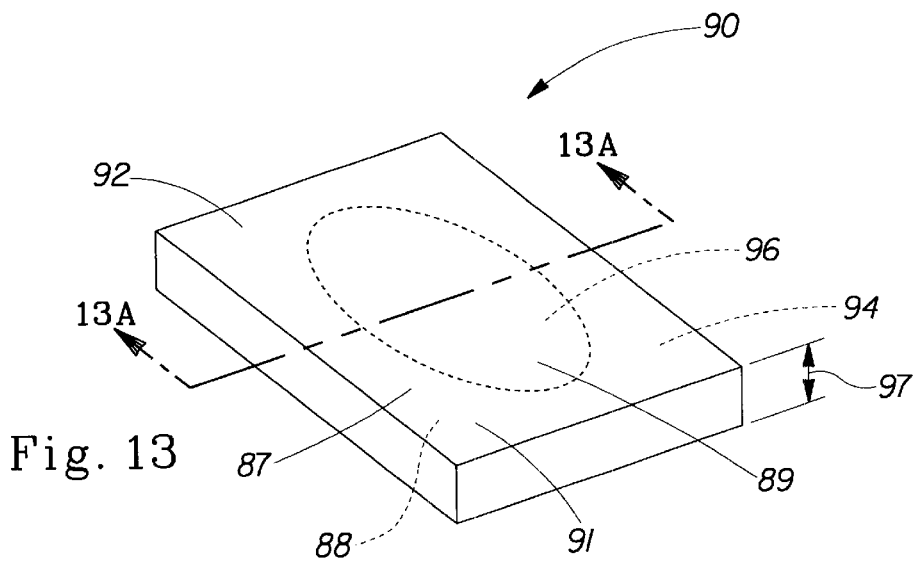
FIG. 13 shows a perspective view of a bodily waste isolation device of the present invention in a compressed state before activation.
Figure 14:
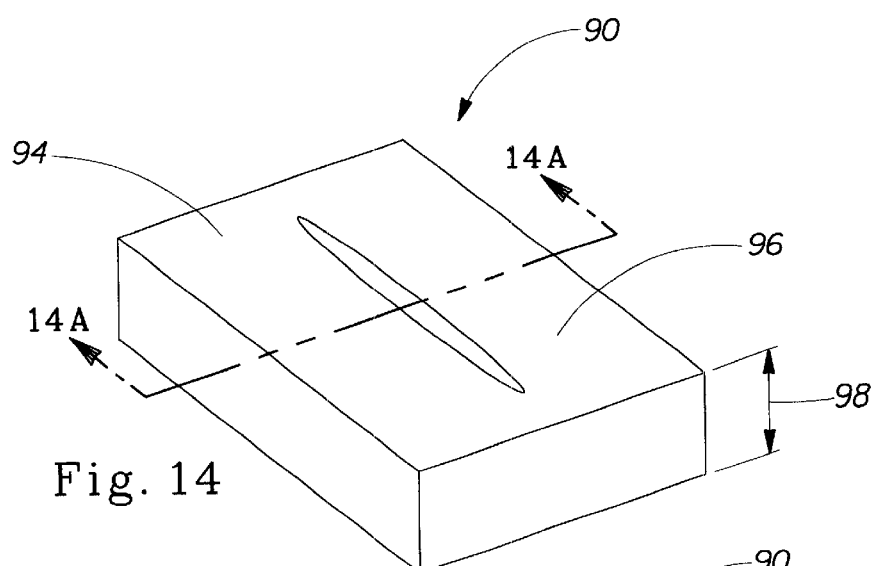
FIG. 14 shows a perspective view of one embodiment of FIG. 13 after activation.
Figure 14A:
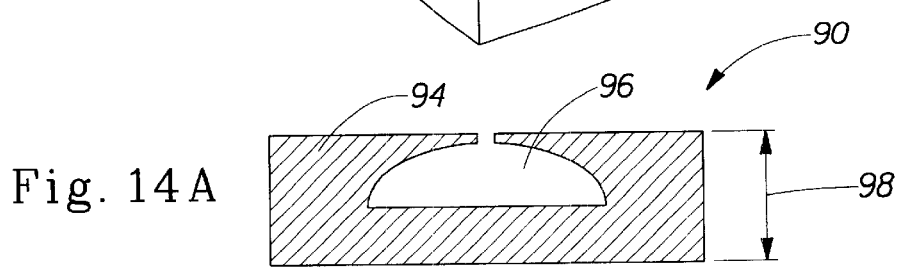
FIG. 14A shows a sectional view of FIG. 3 taken along line 3A—3A of FIG. 14.

In one embodiment of the present invention, as shown in FIGS. 13–14A, a feces modifying delivery device 90 comprises a compressed resilient material 94, additionally comprising one or more feces modifying agents, that is held in a compressed state by a pressure differentiation device 91. A pressure differentiation device, as used herein, is any device or structure that can maintain a resilient material in a compressed state (e.g., can store energy by providing a constraining pressure on the compressed resilient material 94). A "compressed state" is defined as the condition in which a material is maintained at a smaller volume than the material would have if unconstrained and under zero applied pressure. With respect to resilient materials, a compressed state may generally be achieved by applying a pressure to a surface of the material or via any other means known in the art. The pressure differentiation device may, for example, comprise a vacuum sealed bag or tensioned materials, such as elastic or inelastic bands or strands, strips, films, nonwoven, scrims, or foams, that constrain a resilient material. Preferably, the compression of the resilient material maintained by the pressure differentiation device 91 may be at least partially reduced (i.e., the compressed resilient material 94 may at least partially expand) via a trigger mechanism. A trigger mechanism is any element or device, such as a sensor, actuator, or combination thereof, that responds to an input to effect the equalization of pressure in the pressure differentiation device 91 and allow the compressed resilient material 94 to at least partially expand.

Figure 11A:
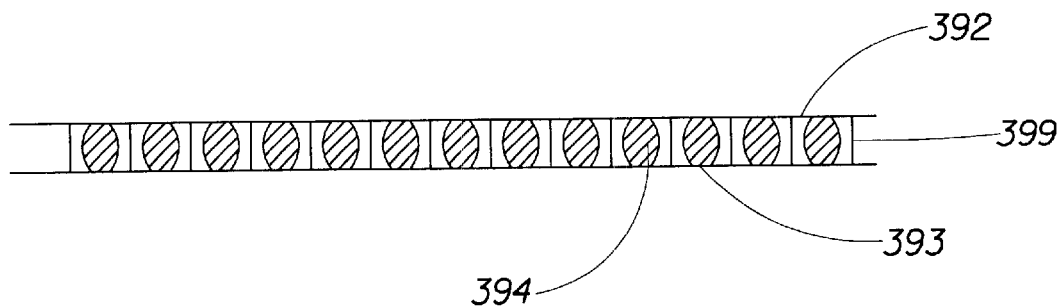
FIGS. 11A–11C show a sectional view of an embodiment of a responsive system including a mechanical pump of the present invention.
Figure 11B:
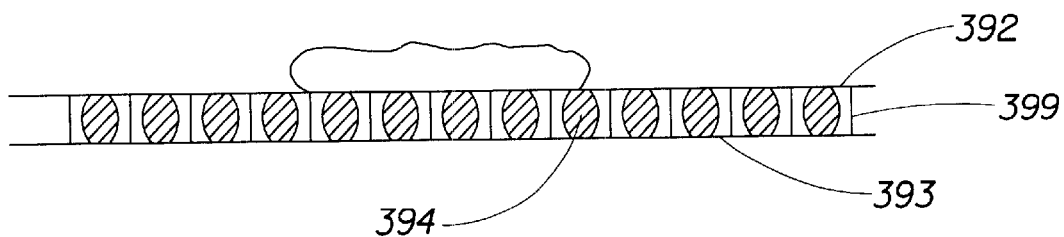
Figure 11C:
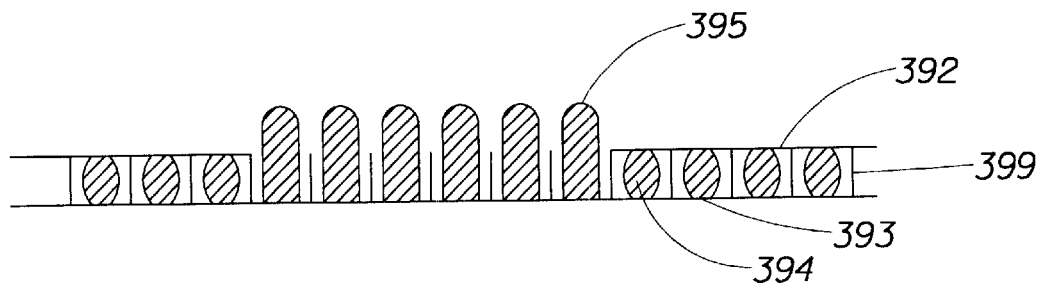
Figure 12:
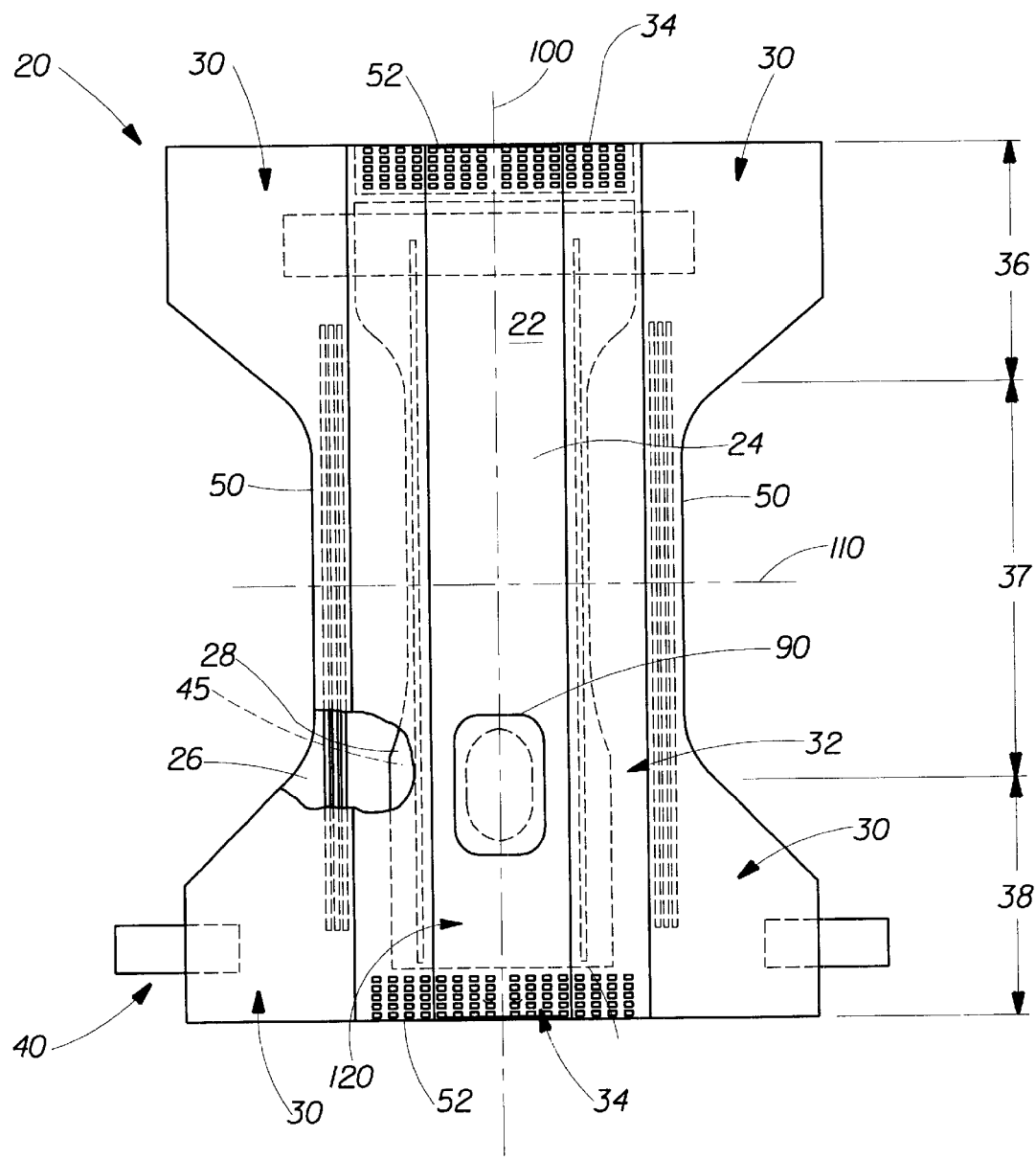
FIG. 12 is a plan view of the article made in accordance with the present invention in a flat-out state with portions of the structure being cut-away to more clearly show the construction of the article, wherein the article is a diaper.

The bodily waste isolation device 90 may be placed in the article 20 adjacent to the anus of the wearer so that when it is allowed to expand it may capture bodily wastes such as feces and store the waste away from the skin of the wearer. In this embodiment, if the soluble bag responds to fecal moisture and the bodily waste isolation device captures feces in response to the fecal moisture, the responsive system comprises a discontinuous closed loop responsive system because the system acts upon the sensed input in a discontinuous manner when a threshold level of the input is present. If the soluble bag responds to urine, however, the responsive system comprises a discontinuous open loop system because the responsive system acts upon something other than the input, i.e., the system captures feces instead of urine. Alternatively, the resilient material 94 may be an absorbent material that functions as a pump by drawing fluid into its body as it expands. As shown in FIGS. 11A through 11C, for example, a high porosity, large cell, resilient foam 394 as described above may be compressed and contained in a film, envelope, bag or capsule having at least a soluble portion 392 and an insoluble backing 393. FIG. 11A shows an example of a mechanical pump of the present invention. FIG. 11D shows feces on the structure, and FIG. 11C shows the structure after the feces is absorbed. Preferably, each cell comprising the compressed foam is individually held under vacuum. When a liquid such as urine, menses or fecal moisture contacts the soluble film, the film dissolves and allows the compressed foam in the cells contacted by the feces to expand and draw fluid into the foam as it expands. In one embodiment, the absorbent material may include multiple cells that are individually vacuum sealed via cell walls 399 in order to maintain a suction with overlying waste. In this embodiment, if the responsive system pumps the fluid that is detected by the soluble material, the responsive system comprises a discontinuous closed loop responsive system because the system acts upon the input detected by the sensor.

In the embodiment of the present invention shown in FIGS. 13, 13A, 14, and 14A, the pressure differentiation device 91 comprises a bag 92 which includes an exterior 87 and an inner chamber 88. At least a portion of the bag 92 is preferably water soluble and functions as a trigger mechanism 89. Preferably, the resilient material 94 is held within the inner chamber 88 of the pressure differentiation device 91 under vacuum compression. That is, at least a portion of the resilient material 94 is maintained in an at least partially compressed state by the pressure differentiation device 91. In preferred embodiments, the pressure in the inner chamber 88 is lower than the ambient pressure, thereby providing a means to maintain the resilient material 94 in at least a partially compressed state. In this embodiment, the ambient pressure is the atmospheric pressure. When a threshold level of an input is reached or sensed, the trigger mechanism 89 may effect an increase in the pressure in the inner chamber 88, allowing at least a portion of the compressed resilient material to expand to at least a portion of its uncompressed thickness. For example, when a threshold level of moisture (i.e., the input) dissolves a portion of the water soluble bag 92 or seal and allows the pressure difference between the inner chamber and the ambient pressure to equalize, the resilient material 94 expands.

The resilient material may be any suitable shape when compressed or expanded. For example, the resilient material may be a resilient synthetic polymer or plastic foam that has a shaped void that, when expanded, has a sufficient volume to capture feces. Alternatively, the resilient material 94 may comprise micro- or macroporous foams, loop structures, springs, resilient highloft nonwovens, coiled structures, or various shapes of resilient materials elastically deformed into a lower-volume, constrained geometry. Further, the resilient material 94 may comprise two or more resilient elements comprising the same or different materials. For example, the resilient material 94 may comprise both microporous and macroporous elements such as micro and macroporous foams. In any case, the individual resilient elements of the resilient material may be configured in any suitable manner, including at least partially overlapping, abutting or non-touching or completely separate from each other.

In the bodily waste isolation device 90 embodiment shown in FIGS. 13, 13A, 14, and 14A, the resilient material 94 may comprise any elastically deformable foam that has suitable compression and recovery properties so that it is capable of being compressed and held within the pressure differentiation device 91 (e.g., bag 92) and also capable of recovering a substantial proportion of its original height, preferably at least about 75%, after release of a constraining force. At least a portion of the bag 92 may comprise a soluble region or a soluble seal. The soluble seal may be integral with the bag 92 (e.g., a portion of the bag 92 material) or may be a separate element (e.g., a soluble material affixed over a hole or permeable region in the bag 92). The soluble region or seal may dissolve when contacted by water, urine, fecal enzymes, etc. The bag 92 preferably retains the resilient material 94 under vacuum compression until a portion of the soluble region of the bag 92 dissolves enough (i.e., a threshold level of water is detected) to discontinuously release the vacuum, and, thereby, the stored energy in the compressed resilient material 94. Once expanded, the foam is also preferably rigid enough to withstand the weight of a baby, for example, so that the foam will not compress significantly, preferably less than about 50%, and release the captured waste if the baby sits on the device. An EVA foam, for example, such as the ones available from Foamex Corporation of Eddystone, Pennsylvania identified as SIF/210PP1 or Aquazone 80A foam, or from Sentinel Products Corporation of Hyannis, MA identified as MC1900 EVA 2 lb/ft$^3$, or a HIPE foam as described in U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997 may be used as the feces capture compression material 94.

Figure 13A:
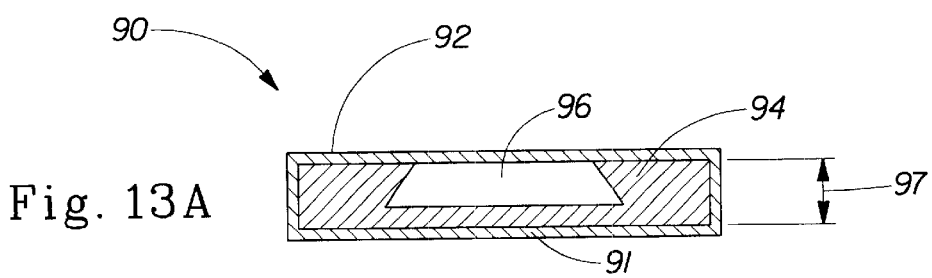
FIG. 13A shows a sectional view taken along line 2A—2A of FIG. 13.

As shown in FIGS. 13 and 13A, the compression material 94 may include an aperture 96 that is open when the resilient material 94 is compressed. When the resilient material 94 expands, the aperture 96 may be enclosed by the perimeter of the resilient material 94 as shown in FIGS. 14 and 14A. This allows the waste to be captured or encapsulated away from the skin of the wearer inside the aperture of the resilient material. Alternatively, the resilient material 94 may have an open aperture that acts as a spacer and provides a void space having a sufficient volume to store bodily waste deposited in the article 20. This allows the resilient material 94 to receive multiple bodily waste insults after the resilient material 94 has expanded.

As noted above, the resilient material 94 may comprise two or more individual resilient elements comprising the same or different materials. For example, the resilient material may comprise both microporous and macroporous resilient elements such as micro- and macroporous foams. The resilient material 94 may comprise a first resilient element which preferably comprises macroporous reticulated polyurethane foam (e. g., PG14848T20 having 20 pores per square inch from PCF Foam Corporation of Hamilton, Ohio) having an opening 96 for feces storage and an extension into the urine loading zone. The resilient material 94 may additionally comprise a second resilient element (e.g. a microporous foam such as those described in U.S. Pat. Nos. 5,260,345 and 5,625,222 cited above). Preferably, the second resilient element has an opening for feces generally coextensive with the opening 96 in the first resilient element and is disposed on the wearer-facing side of the first resilient element, except in the urine loading zone. (However, embodiments are contemplated wherein the first resilient element is disposed on the wearer facing side of the second resilient element.) The first resilient element may serve to promote air flux to at least a portion of the second resilient element once the soluble bag 92 or seal is dissolved. This preferably results in a rapid expansion of at least the second resilient element as the pressure inside equilibrates with the ambient pressure. Preferably, the larger pores in the first resilient element (e.g. macroporous foam) do not become obstructed by residual partially dissolved bag material, providing a clear air pathway for rapid pressure equalization in the rest of the bag and/or resilient material 94.

The various components of the resilient material may also differ from each other in any property, including compressive modulus, bending modulus, thickness, pore size distribution, chemical composition, porosity, and surface energy. In one nonlimiting example, the first and second resilient elements may compress in the range between about 50% and about 80% and about 5% and about 50%, respectively, under an applied pressure of about 1.0 psi. Preferably, at least one of the components in a multiple component system compresses no more than about 25% under an applied pressure of about 1.0 psi. However, regardless of the construction, the opening 96 in the resilient material preferably provides an available volume of at least about 20 cubic centimeters under an applied pressure of about 0.1 psi once the structure has been activated (e.g., via water dissolving an encapsulating film).

Figures 15, 15A:
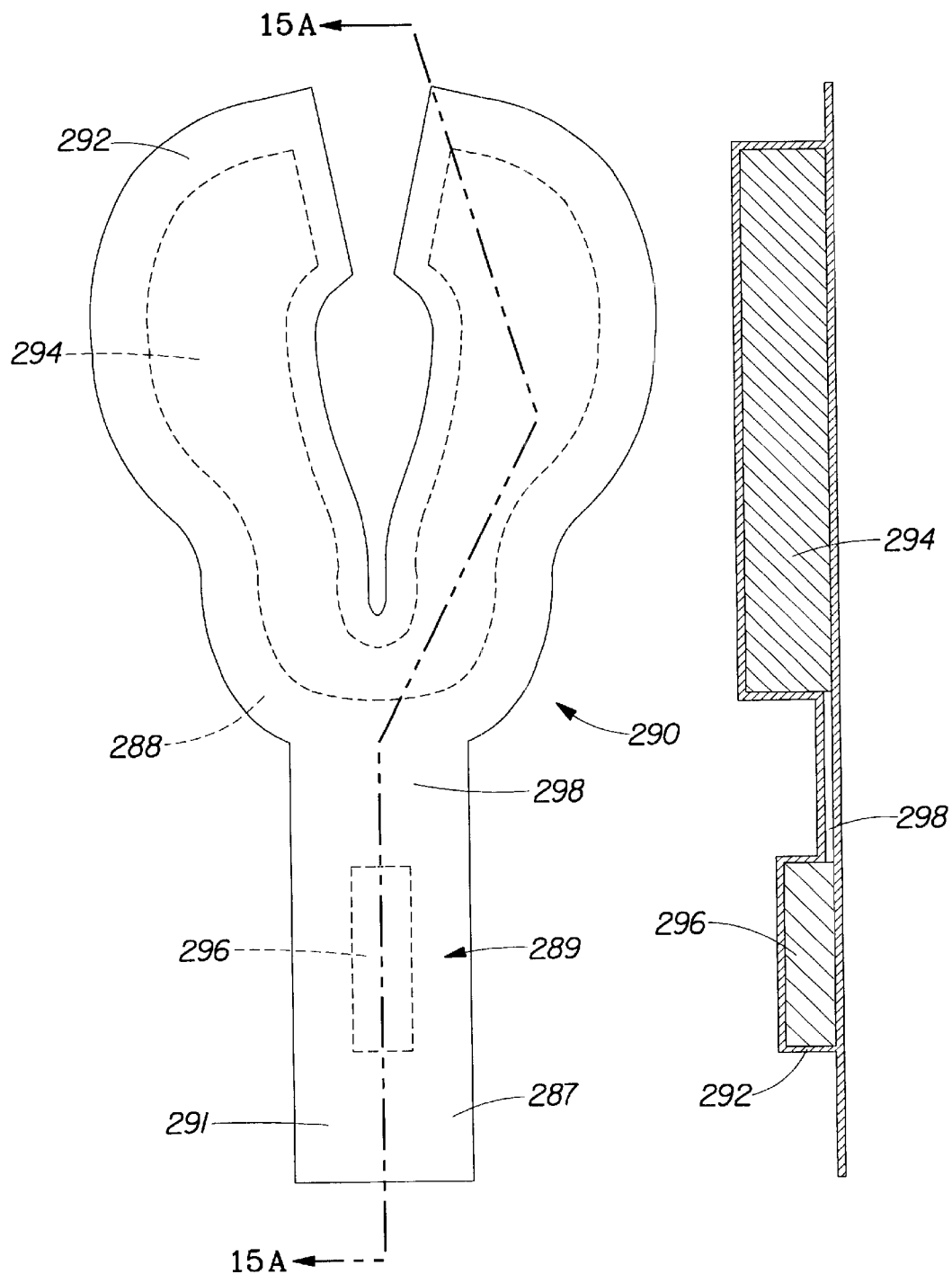
FIG. 15 is an enlarged, plan view of an exemplary bodily waste isolation device.
FIG. 15A is a cross-section of the device shown in FIG. 15 taken through section line 15A.

As shown in FIGS. 15 and 15A, the present invention may include a bodily waste isolation device 290 including two or more resilient elements 294 and 296 which are separate from each other and not directly touching or directly joined to each other but at least a portion of each which are both held under vacuum compression. The resilient elements 294 and 296 are preferably held under vacuum compression within a pressure differentiation device 291. The pressure differentiation device 291 preferably includes an exterior and an inner chamber 288. The exterior 287 of the pressure differentiation device 291 preferably keeps the inner chamber 288 at a pressure which is less than the ambient pressure of the atmosphere surrounding the article until a predetermined event takes place, such as urination or defecation. Further, the bodily waste isolation device 290 preferably includes a trigger mechanism 289 which is capable of releasing the pressure differential between the inner chamber 288 of the pressure differentiation device 291 and the ambient pressure or at least reducing the pressure differentiation. The trigger mechanism 289 may include any means known in the art capable of releasing or reducing the pressure differential, including but not limited to any of the sensors or actuators described herein or any component of an actuator or sensor. In embodiments wherein the bodily waste isolation device 290 is adapted to be triggered by urine, the trigger mechanism 289 is preferably disposed in an article such that it will be located where urination is likely to occur (i.e. a urine loading zone) or is operatively associated with a sensor or actuator located in the urine loading zone such that the trigger mechanism will be capable of releasing the vacuum when the wearer urinates or otherwise causes the trigger to activate.

In the embodiment shown in FIGS. 15–15A, the first resilient element 296 preferably comprises a material which provides a low resistance air flux pathway for pressure equilibration once the pressure differential device 291 (e.g. bag 292) is compromised and the vacuum is lost. In one preferred embodiment, the first resilient member includes a macroporous foam, however, other resilient materials such as the resilient materials described above may be suitable. Because the resilient elements 294 and 296 are operatively connected via an open passageway 298 in the pressure differentiation device 291 in the region between the elements, the air passing into the first resilient element 296 can flow toward the second resilient element 294, providing a means for filling the second resilient element 294 and any space around it with air. Accordingly, the second resilient member 294 is able to expand upon dissolution of at least a portion of the bag 292 near the first resilient element 296.

Figures 16, 16A:
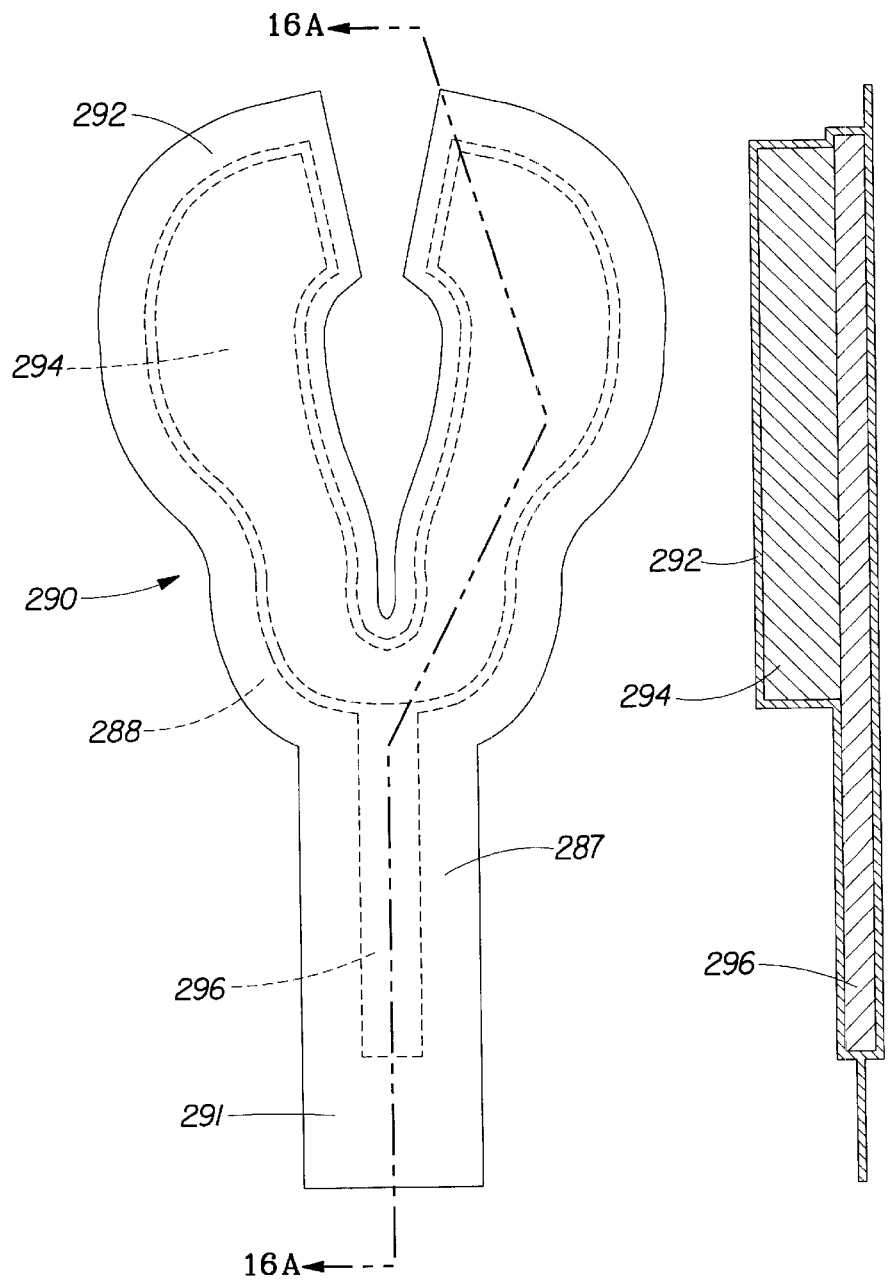
FIG. 16 is an enlarged, plan view of an exemplary bodily waste isolation device.
FIG. 16A is a cross-section of the device shown in FIG. 16 taken through section line 16A.

In another embodiment, as shown in FIGS. 16 and 16A, the article of the present invention may include a first resilient element 296 and a second resilient element 294 configured to be abutting one another or at least partially overlapping. The first and second resilient elements are preferably held under vacuum compression in the inner chamber 288 of a pressure differential device 291, as described above. At least a portion of the first resilient member 296 is preferably disposed outwardly from any overlapping portions of the first and second resilient elements. As above, the bodily waste isolation device 290 preferably includes a trigger mechanism 289 which is capable of releasing the pressure differential between the inner chamber 288 of the pressure differentiation device 291 and the ambient pressure or at least reducing the pressure differentiation. The trigger mechanism 289 is preferably disposed in an article such that it will be located where urination is likely to occur (i.e. a urine loading zone) or is operatively associated with a sensor or actuator located in the urine loading zone such that the trigger mechanism will be capable of releasing the vacuum when the wearer urinates or otherwise causes the trigger to activate. When the pressure differential is removed the resilient elements 294 and 296 are able to increase in volume. It has been found to be advantageous to have at least one of the first or second resilient elements to include a material which has openings that easily permit the passage of air and which do not become blocked, for example, by the material of a soluble bag 292 or seal which comprises the pressure differential device 291. In preferred embodiments, such resilient materials may include macroporous foams, however other materials including the resilient materials described above may be suitable.

Figure 17:
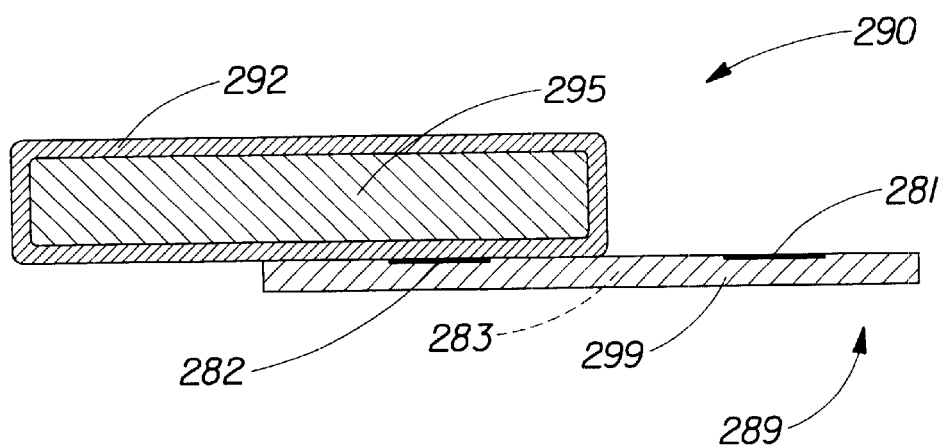
FIG. 17 is a cross-section view of an alternative embodiment of the waste isolation device of the present invention.

In yet another embodiment, as shown in FIG. 17, the article of the present invention may include a trigger 289 comprising a closed system liquid transport member 299, as described above, operatively connected to the bodily waste isolation device 290. The closed system liquid transport member 299 preferably includes an inlet port 281, an outlet port 282 and a liquid 283. The outlet port is preferably disposed adjacent at least a portion of pressure differential device 291, such as a soluble bag 292 or soluble seal. The inlet port 281 is preferably disposed in a different location from the outlet port 282. For example, the inlet port 292 is preferably disposed such that it is located near or at the urine or other discharge zone of the article into which the waste isolation device 290 is in incorporated. Accordingly, when the wearer urinates or otherwise discharges fluid, the fluid is accepted into the inlet port 281. As a result, the closed system liquid transport member 299 releases some liquid from the outlet port 282 which triggers the dissolution at least a portion of the soluble bag 292 or seal. Once dissolved, the pressure differential in the bag is reduced or eliminated and the resilient material 295 is able to expand.

In any of the embodiments of the present invention utilizing a soluble bag, the soluble bag may be soluble in the presence of one or more different types of input, such as water, urine, fecal enzymes, a pH level, etc., and may have physical and/or chemical characteristics (e.g., thickness) that may be designed to set a threshold level of that input required to dissolve the bag. The soluble bag may, for example, comprise a plastic film that is soluble to water such as PVA films supplied by Chris-Craft Industrial Products, Inc. of South Holland, Ill. as MONOSOL M703 1, M7030, M8630, M8534, or E6030 film, or H. B. Fuller Company of St. Paul, Minn. as HL 1636 or HL 1669-X. The film thickness, for example, may also be modified to provide a desired activation. The film used may, for example, also have a thickness in the range from about 0.0005 to about 0.0015 inches. An HL 1636 film having a thickness of about 0.001 inches, for example, will activate with a moisture content of about 0.049 grams per square inch.

In some embodiments of the present invention, the bodily waste isolation device may operate as a non-modulating, discontinuous responsive system. For example, if a soluble bag is used, the soluble portion of the bag acts as a sensor that responds to a specific input. The sensor may, for example, be responsive to water in urine or an enzyme in feces. When any soluble portion of the bag contacts a threshold level of urine, fecal moisture, or a fecal enzyme, the soluble portion of the bag dissolves and releases the compression material, which expands to capture, surround or envelop the feces deposited upon the article. The physical and chemical characteristics of the material used to form the bag define the threshold level of the input and act as a controller that determines when the compression material is to be released. When the bag dissolves, the release of vacuum and the expansion of the compression material function as an actuator to capture the bodily waste. Thus, the bodily waste isolation device acts as a one-time discontinuous switch that releases the stored mechanical energy of the compression material when a threshold level of a given input is detected. The useful energy of the responsive system includes: (stored energy)—(hysteresis loss). The compression material used preferably has a minimal hysteresis loss and a maximum recovery. More preferably, the compressive hysteresis loss is less than about 25% so that the recovery upon release is at least about 75%.

In another embodiment of the present invention, a foam such as described in the above example or another resilient material may be twisted creating torsional mechanical potential energy and held by a pressure differentiation device as described above, such as a soluble film envelope, bag or capsule as described above. The twisted resilient material may be held in the twisted position in the soluble film, envelope, bag or capsule under vacuum. In this embodiment, when a threshold level of moisture, pH, etc. is detected the film or capsule dissolves, discontinuously releasing the vacuum, and releasing the foam. The stored torsional mechanical potential energy causes the foam to unwind and may perform a responsive function such as treating or mixing the feces with a feces modifying agent, storing, capturing or entrapping bodily waste such as feces, urine or menses, wiping the skin of the wearer, applying a skin treatment agent to the skin of the wearer, etc.

In yet another embodiment, an electrical sensor may detect changes in the electrical activity of the wearer's external anal sphincter muscles to predict an imminent urination and/or defecation, i.e., a proactive sensor. Upon detection of a threshold signal change in electrical activity of the muscles, the sensor or the controller may, for example, trigger the opening of a valve to release water to dissolve a water soluble portion or seal of a bag that holds a compressed foam, additionally comprising a feces modifying agent, in vacuum compression as described above, in preparation to treat waste of the imminent urination and/or defecation. Alternatively, the switch may effect the release of a skin care composition comprising a feces modifying agent to treat the skin surface prior to feces contact of the skin. In this embodiment, the responsive system comprises a discontinuous system that responds to the electrical activity of the wearer's external anal sphincter muscle when that electrical activity reaches a threshold signal level. This responsive system also comprises an open loop system because the system is acting upon something other than the electrical activity input signal, i.e., it is acting on the feces or the article.

In still another embodiment, a sufficient quantity of water containing electrolytes (e.g., from urine or feces) may be detected by an electrical sensor when the electrolytic water completes a circuit, i.e., as a switch, causing current from a stored energy source such as a battery to initiate a chemical reaction such as a phase transition, etc. For example, a current may be applied to an electrically sensitive gel which causes it to change geometry and deliver a feces modifying agent to the feces. Again, this embodiment comprises a discontinuous responsive system that may be an open loop or a feedback control loop system depending upon whether the input sensed is being affected by the responsive system. If the sensor detects moisture in urine, for example, the responsive system creates a void space for receiving feces is an open loop system. If the sensor detects fecal moisture, however, the responsive system comprises a feedback control loop system because it acts upon the input being sensed. In this example, the feedback control loop system may further comprise a modulating system if the void space captures the fecal moisture along with the feces, the moisture evaporates or is drawn away from the sensor element, thereby opening the circuit, and the controller activates another void space when the sensor detects fecal moisture again.

Figure 3:
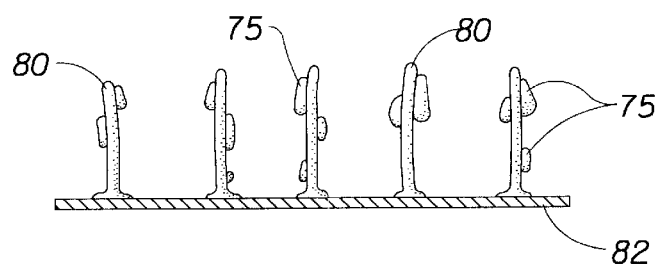
FIG. 3 is an enlarged cross sectional view of an embodiment of the present invention.

In alternative embodiments, the FMA may be disposed on or associated with three-dimensional structures joined to or separate from other elements of the absorbent article, For example, the absorbent article may include an element with protrusions, bumps, loops or the like which help make the FMA available to contact the feces. In one preferred embodiment, "hairs" or strands of a hot melt resin including the feces modifying agent may be printed on a substrate 82. (An example of a substrate including hairs comprising an FMA is shown in FIG. 3.) The agent may be incorporated into the resin such that it moves to the surface of the hairs and is available to the feces. Alternatively, the agent may be releasably bonded to the hairs via any of the techniques described above. Examples of suitable hairs and hooks are described in more detail in U.S. Pat. No. 5,058,247 issued to Thomas et al. on Oct. 22, 1991; U.S. Pat. No. 5,116,563 issued to Thomas et al. on May 26, 1992; U.S. Pat. No. 5,326,415 issued to Thomas et al. on Jul. 5, 1994; and U.S. Pat. No. 5,762,645 issued to Peck et al. on Jun. 9, 1998. Each of these patents is incorporated by reference herein.

Figure 2:
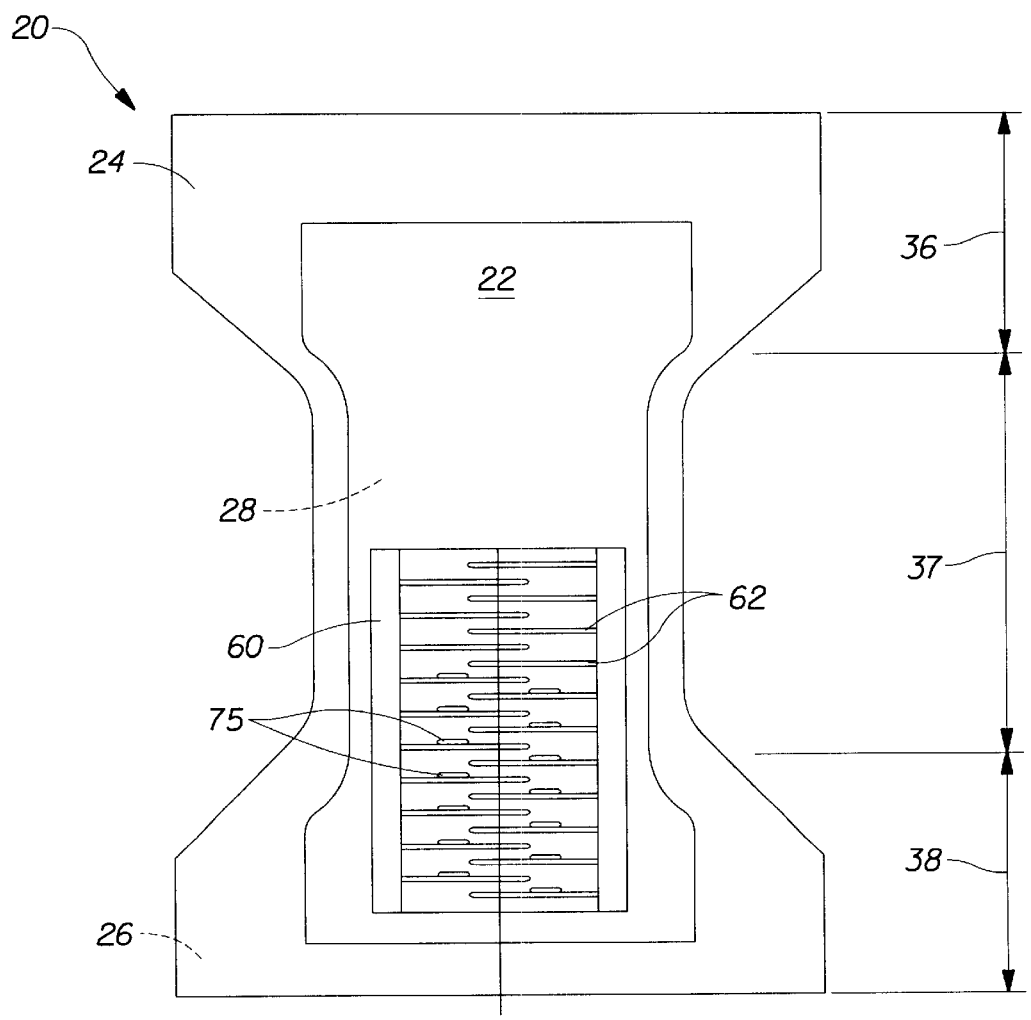
FIG. 2 is a plan view of an alternative embodiment of the present invention.

In yet another embodiment, the FMA may be delivered to the feces via a brush structure 60, one example of which is shown in FIG. 2. A brush structure may include a multiplicity of substantially aligned strands, fibers, twisted yarns, strings, or other filamentous materials affixed to a substrate. The substrate may be planar, curved, ribbon-like, or have compound curvature and may be porous or non-porous. The brush filaments 62 are preferably bendable under the forces exerted by the feces during excretion so as to allow feces to readily pass through or between the filaments 62. The brush filaments 62 may be permanently or releasably affixed to the substrate. The filaments 62 may be of plant or animal origin (e.g., cotton, etc.), cellulosic or synthetic and may have different or similar lengths. The FMA is releasably affixed to the laments 62 of the brush structure 60 such that as the feces is pushed past the brush filaments 62, the agent is released and mixed with the feces. The brush structure 60 may be integral with the article or may be separately applied to the wearer's perianal region and may optionally comprise adhesive or other joining means for adhering to the wearer or the article. The brush structure 60 may be mounted over a spacer (as described above) having a void under the filaments 62 so as to provide a space for the treated feces to occupy.

The FMAs may also be delivered via the use of "smart" gels that undergo a phase transition or a geometric or volume change in response to certain changes in pH, water content and/or some other trigger. Shape memory materials (i.e., metal alloys or plastics that return to a pre-set geometry or shape when the temperature reaches a pre-determined threshold) may also be employed to move the agent into position to contact or mix with feces, given the appropriate temperature change. Additionally, swellable materials, such as superabsorbent polymers or foams, may be used to promote feces contact with the FMA. As a structure containing such swellable materials imbibes water, whether from feces or urine, it may transport a FMA associated with the body-facing surface of the structure toward a fecal mass and/or promote mixing with the feces. Foam-forming materials may also transport the FMA and promote contact with feces in the article. In this case, the foam forming material comprises the FMA (or is associated with the agent) and coats the fecal mass as the foam is generated and its volume increases.

The FMAs may also be held on or within macro-particulate elements 170, as described below. These macro-particulate elements 170 may be contained in a waste management element 120, attached to a topsheet, cuff, or other feature of the article (releasably or not), or loose in a separate article attached independently to the body. Some exemplary macro-particulate structures are shown in FIGS. 18–21. Further, any of the structures that hold, carry, deliver, or mix the FMA may comprise protrusions or other three-dimensional geometries designed to increase contact area of the FMA and the feces and/or to promote mixing.

In preferred embodiments, the FMA is associated with the topsheet of the absorbent structure or article. However, the FMA may be associated with a layer underneath the topsheet, such as an acquisition layer. In embodiments where the FMA is disposed in a layer underneath a topsheet, such as in a waste management element 120, feces must readily penetrate the topsheet, sublayer, and any other overlying structure for the agent to be available in an effective amount. Thus, it is preferred that such structures have an Acceptance Under Pressure of at least about 0.50 g/cm2/J, and preferably at least about 1.0 g/cm2/J, as described in the Test Methods section below. In any case the agent is preferably located near the region of the article generally associated with the wearer's perianal region.

Figure 18:
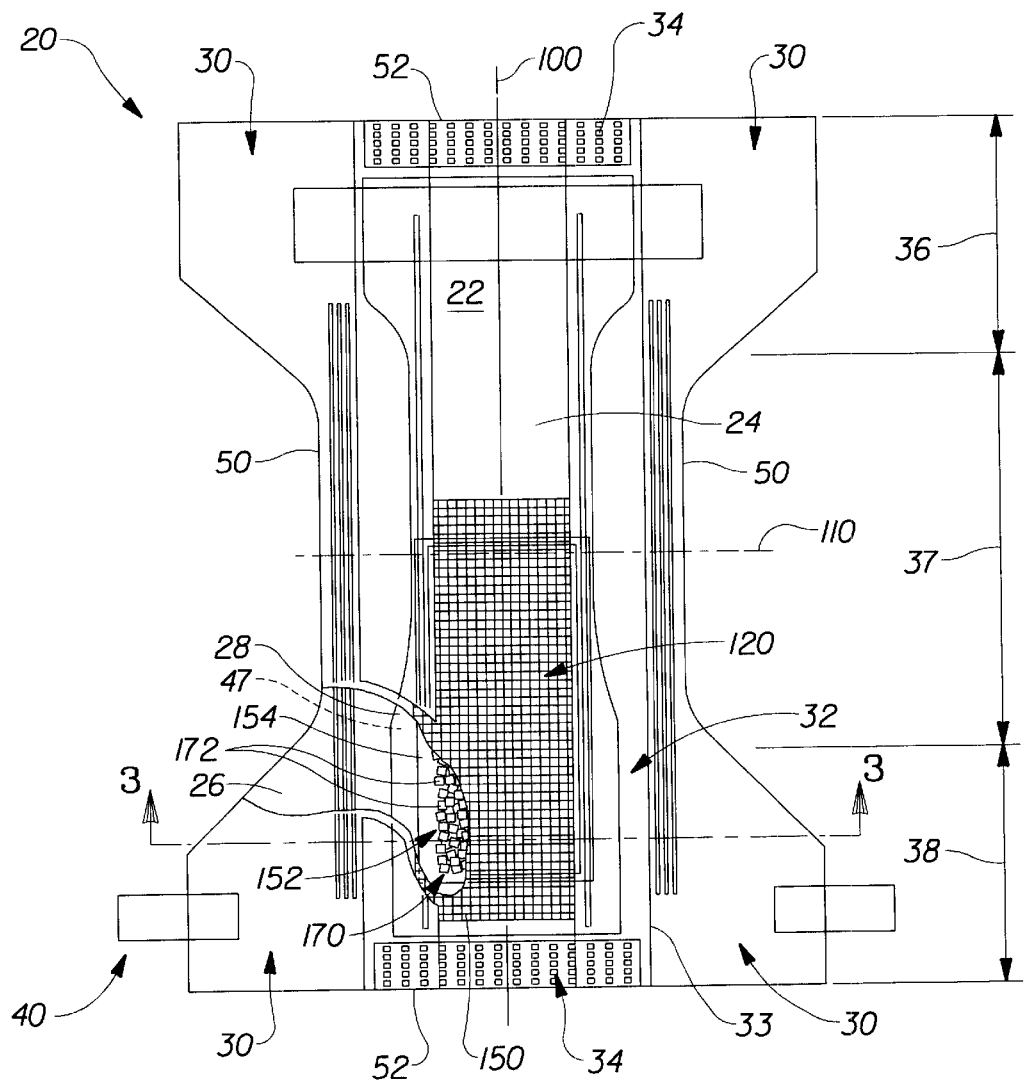
FIG. 18 is a plan view of an absorbent article embodiment of the present invention having portions cut away to reveal the underlying structure, the body-facing surface of the diaper facing the viewer.
Figure 19:
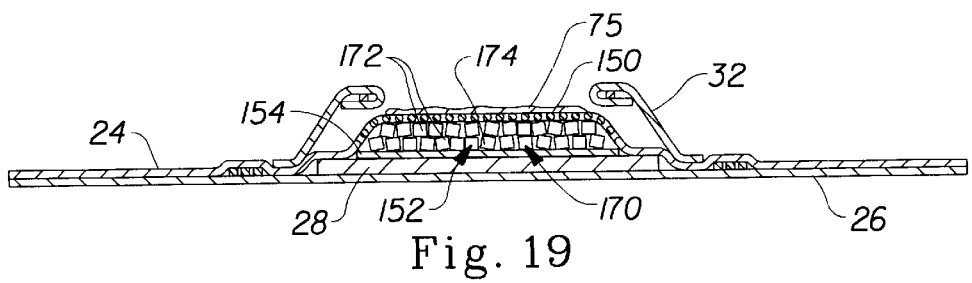
FIG. 19 is a cross sectional view of an absorbent article embodiment of the present invention taken through the section lines 3—3.
Figure 20:
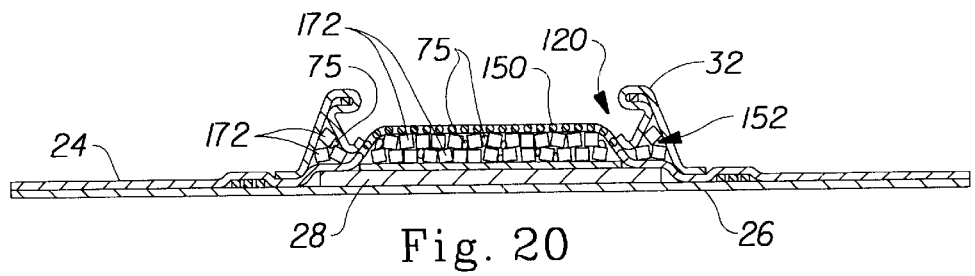
FIG. 20 is a cross sectional view of an alternative embodiment of an absorbent article of the present invention.

As shown in FIG. 18, the present invention may include a waste management element 120. The waste management element 120 is designed to help manage the acceptance, storage and/or immobilization of the viscous fluid bodily waste. The waste management element 120 can be located anywhere in the article, including the crotch region or either waist region, or may be associated with or be included in any structure or element such as the core 28, a leg cuff, etc. In preferred embodiments, the waste management element 120 is located in the region of the article that is near the wearer's perianal region when worn. This helps ensure that any waste discharged is deposited on or near the waste management element 120, Although structures which accept, store and immobilize viscous fluid bodily wastes are preferred, in certain embodiments of the present invention, the waste management element 120 may comprise only an acceptance element, a storage element or an immobilization element, or may include a combination of two of the elements, but not the third. Also, in certain embodiments, one element may perform more than one function (e.g., a storage element may perform both the storage and immobilization functions). For example, the absorbent article of the present invention may include an acceptance and a storage element to manage viscous fluid bodily wastes without a separate immobilization element, per se.

The acceptance element 150 may be any material or structure capable of accepting bodily exudates. (As used herein, the term "accept" or "acceptance" refers to the penetration of a structure by materials deposited thereon. Penetration is defined by the passage of materials through the surface of the structure upon which the material was deposited. Penetration of nonuniform structures can be defined as the passage of a material through a plane defining the surface upon which the material was deposited.) The acceptance element 150 may include a single material or a number of materials operatively associated with each other. Further, the acceptance element 150 may be integral with another element of the diaper 20 or may be one or more separate elements joined directly or indirectly with one or more elements of the diaper 20. Further, any or all of the acceptance element 150 may be removable from the absorbent article for separate disposal, if desirable.

The acceptance element 150 is preferably disposed at least partially in the crotch region 37 of the diaper 20 adjacent the body surface 47 of the core 28, although in some alternate embodiments, the acceptance element 150 may include at least a portion of a leg cuff, waistband, fecal waste containment pocket, or the like, or may be operatively associated with any such features. Preferably, at least the portion of the acceptance element 150 located in the region of diaper 20 which is near the anus of the wearer during use is unobstructed by overlying layers of structures, such as the topsheet 24. Thus, it may be desirable to cut out a portion of the topsheet 24 in the region of the article intended to be located near the wearer's anus and to provide an acceptance element 150 as the body-side liner in that region. Alternatively, any or all of the topsheet 24 may be made or treated to act as the acceptance element 150. In one embodiment, as shown in FIG. 18, the acceptance element 150 includes at least a portion of the topsheet 24. In other embodiments, the acceptance element 150 may include at least a portion of other elements of the diaper such as the absorbent core 28 or the storage element (described below).

In some embodiments, it may be desirable to provide the diaper 20 with different acceptance capability in different portions of the diaper. This may be accomplished by providing different acceptance elements in the different regions of the diaper 20 or by providing a single acceptance element 150 which has been manufactured or treated to have regions of differing acceptance characteristics. Further, the acceptance element 150 may be elevated above the plane of the body-facing surface of the article so as to be in better control of exuded viscous fluid bodily wastes. In some embodiments, it may even be desirable to have the acceptance element 150 in contact with skin of wearer in proximity of the viscous bodily waste source (e.g., the perianal region).

Suitable materials and structures for use as the acceptance element 150 may be absorbent or nonabsorbent and may include apertured nonwoven webs, apertured films, apertured formed films, scrims, woven webs, scrim, netting, macroporous thin foams, and the like. One particularly preferred material is a woven nylon netting having a basis weight of about 27.3 g/m$^2$, an effective open area of about 60% and a primary aperture size of about 5.0 mm$^2$ (Effective open area and primary aperture size are measured as described in U.S. Pat. No. 5,342,338, which is hereby incorporated by reference herein.) One such material is available as a Toy Tub Bag from Dollar Tree Dist., of Norfolk, Va. Further, the acceptance element 150, or any portion thereof, may be coated with a lotion or other known substances to add, enhance or change the performance or other characteristics of the element. For example, the acceptance element 150 may be hydrophobic or hydrophilic or treated to be either.

As described above, the FMA may be associated with the acceptance element preferably in the wearer's perianal region. In certain preferred embodiments, the FMA is releasably attached to the acceptance element by the means described above. In alternative embodiments, the agent is releasably encapsulated in a structure associated with at least a portion of the acceptance element 150. The agent may be released to the feces upon contact with water, heat, or pressure/wearer motion. The agent may alternatively first be transferred to the wearer's skin or another portion of the article (e.g., leg cuff) prior to deposition onto the feces. For example, urine may effect the release of a releasably encapsulated agent or composition. The agent may transfer to the wearer's skin by body contact and/or pressure. Upon subsequent contact with feces, the agent will transfer from the skin to the surface of the feces.

Once viscous bodily waste has penetrated the waste management element 120, it is desirable to store or hold the waste away from the wearer during the remainder of the wearing cycle and away from the caregiver during the changing process. As used herein, the term "store" refers to the physical separation of material deposited in a diaper from the body-facing surface of the article such that the material deposited in the diaper is not immediately in contact with or accessible to the wearer's skin. Adequate storage capacity is essential to reduce the probability of leakage and the area of skin contaminated by viscous bodily waste because viscous bodily waste that has been stored is less likely to be available to the body-facing surface of the structure for leakage and migration within the article.

The storage element 152 may be located anywhere in the diaper 20. However, it is preferred that the storage element 152 be operatively associated with the acceptance element 150 and/or topsheet 24, if any, such that viscous bodily waste accepted by the acceptance element 150 may enter the storage element 152. (Embodiments are contemplated wherein the diaper 20 has no topsheet 24 or acceptance element 150. In such cases, the bodily waste may enter the storage element 152 directly, without passing through any overlying structure.) In any case, it is preferred that the storage element 152 be located in the region of the diaper 20 which is located near the wearer's anus when the diaper 20 is worn. Accordingly, it is preferred that at least a portion of the storage element 152 be disposed in the crotch region 37 of the absorbent article. However, in some alternate embodiments, the storage element 152 may include at least a portion of either waist region, a leg cuff, the waistband, a fecal waste containment pocket, or the like, or may be operatively associated with any such features. Further, the storage element 152 may be elevated above the plane of body-facing surface of the article so as to be in better control of exuded viscous bodily wastes. In some embodiments, it may even be desirable to have the storage element 152 in contact with skin of wearer in proximity of the viscous bodily waste source (e.g., the perianal region).

The storage capability of the storage element 152 may be uniform or may vary throughout the diaper 20. Such variations may be accomplished by employing multiple storage elements 152 in the diaper 20 or by providing a single storage element 152 with regions of different storage properties. Further, any or all of the storage element 152 may be removable from the absorbent article for separate disposal, if desired.

The storage element 152 may be any material or structure capable of storing bodily exudates, as described above. Thus, the storage element 152 may include a single material or a number of materials operatively associated with each other. Further, the storage element 152 may be integral with another element of the diaper 20 or may be one or more separate elements joined directly or indirectly with one or more elements of the diaper 20. In one embodiment, as shown in FIG. 18, the storage element 152 includes a structure that is separate from the core 28. However, embodiments are contemplated wherein the storage element 152 includes at least a portion of the core 28.

Suitable materials for use as the storage element 152 may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. (As used herein, the term "microporous" refers to materials which are capable of transporting fluids by capillary action. The term "macroporous" refers to materials having pores too large to effect capillary transport of fluid, generally having pores greater than about 0.5 mm in diameter and more specifically, having pores greater than about 1.0 mm in diameter.) One embodiment includes a mechanical fastening loop landing element, having an uncompressed thickness of about 1.5 millimeters available as XPL-7124 from the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga. The storage element 152, or any portion thereof, may include or be coated with a lotion or other known substances to add, enhance or change the performance or other characteristics of the element.

An alternate embodiment of a storage element 152 includes a macro-particulate structure 170 comprising a multiplicity of discrete particles 172, nonlimiting examples of which are shown as FIGS. 18–21. The macro particles 172 preferably have a nominal size, preferably between about 1.0 mm and about 25.4 mm, and more preferably between about 2 mm and about 16 mm. However, particles as small as 0.5 mm and smaller, and particles larger than about 25.4 mm are contemplated. Particles having a nominal size of about 1.0 mm or greater are those which are generally retained on the surface of a U.S. Standard No. 18 mesh sieve screen. Particles having a nominal size of less than about 25.4 mm are those which generally pass through a U.S. Standard 25.4 mm sieve screen. Particles having a nominal size of 16 mm or greater are those which are generally retained on the surface of a U.S. Standard No. 16 mm sieve screen. The nominal particle size is measured prior to incorporating the particles into a storage element 152 for testing or use. Particles having a nominal size of 8 mm or greater are those which are generally retained on the surface of a U.S. Standard 8 mm sieve screen.

The macro-particulate structure 170 may include any number of particles 172. Further, the particles 172 may be unjoined and free to move within the structure 170 or may be joined to each other by any known means. Alternatively, the structure 170 may include an external support, such as a meltblown hot-melt glue, a web, a netting, a scrim, a thread or other adhesive or nonadhesive entangling supports. Any of the particles 172 may also be joined with any other portion of the diaper structure, such as the topsheet or the core. The particles 172 may also be constrained in patterned, three-dimensional regions such as pleats, "pillows", and pockets.

The individual particles 172 may be made from any material suitable for use in absorbent articles, including the materials described above with regard to the absorbent core 28 or the storage element 152. The materials used in the particles 172 may be absorbent, nonabsorbent, microporous, macroporous, resilient, nonresilient, etc. or may have any other desirable characteristic. Examples of macroporous absorbent materials suitable for use in the particles 172 include highloft nonwovens, open cell foams, bundles of fibers, sponges and the like. Other absorbent materials include cellulosic batts, capillary channel fibers, osmotic storage materials such as superabsorbent polymers, etc. Nonabsorbent particles 172 may comprise plastic, metal, ceramic, glass, closed cell foams, column packing materials, synthetic fibers, gels, encapsulated gas, liquids and the like. Further, any or all of the particles 172 may include odor absorbents, lotions, skin care formulations, antimicrobials, pH buffers, enzyme inhibitors, and the like.

The storage element 152 may comprise a single type of particle 172 (size, shape, material, etc.) or may include a mixture of different particles 172. The mixture may be homogeneous; heterogeneous, as when particles 172 having different properties are disposed in certain areas of the storage element 152; layered; or any other desirable configuration. In some embodiments, more than one type of mixture may be employed (e.g., macroporous and nonabsorbent particles 172 may be homogeneously mixed in one layer while another layer includes only absorbent particles.) Different layers of particles may be directly adjacent each other or may be separated by one or more materials, such as netting, scrim, nonwoven or woven webs, film, foam, adhesive, and the like.

The macro-particulate structure 170 preferably includes a continuous interstitial void space 174 that is defined by the space between the particles 172. By varying the size and/or shape of the particles 172, the interstitial void space 174 can be controlled. The particles may be of any known shape, including spheres, oblate spheroids, rectangular and polygonal solids, and the like.

In addition to its storage function, the storage element 152 may transport viscous bodily waste within the absorbent article 20 in directions generally parallel to the plane of the backsheet 26. The transport may be active, such that capillary or other forces result in the movement of the viscous bodily waste or components thereof (e.g., free water). In other embodiments, the transport may be passive whereby viscous fluid bodily waste or components thereof move through the structure under the influence of externally applied forces, such as gravity, wearer pressure or wearer motion. In the case of passive transport, the storage element 152 should have relatively large, interconnected channels, or the like, such that the viscous bodily waste may readily move through the structure with minimum energy input.

The FMA of the present invention may be associated with any portion of the storage element 152, including the macro-particulate structures. In certain preferred embodiments wherein the storage element 152 has raised regions, the FMA is associated with the raised regions of the element. Viscous bodily waste penetrating the acceptance element may contact the FMA and carry it to the "lower" regions of the storage element 152, providing enhanced mixing. For example, the raised tops of loop type storage elements may be slightly wetted or dampened and subsequently contacted with the FMA to releasably affix the FMA to the raised portions, and subsequently dried. The releasable attachment may also be effected via water soluble adhesives. In macro-particulate embodiments, the agent may be held within a macro-porous particle. In alternate embodiments, the agent may be releasably affixed to the exterior surface of the particulate elements. Fecal contact with the FMA preferably effects a release of the agent from the storage element and allows mixing with the feces.

Viscous bodily waste that is accepted by, or penetrates, the absorbent article is preferably also retained in the diaper away from the wearer. One preferred way to retain bodily waste, especially viscous bodily waste, is to immobilize the waste in a location away from the wearer. As used herein, the term "immobilize" refers to the ability of the material or structure to retain stored viscous bodily waste under an applied pressure and/or the influence of gravitational forces.

The immobilization element 154 may be any material or structure capable of reducing the proclivity of viscous bodily waste that has penetrated the immobilization element 154 from leaving the structure. Thus, the immobilization element 154 may include a single material or a number of materials operatively associated with each other. Further, the immobilization element 154 may be integral with another element of the diaper 20 or may be one or more separate elements joined directly or indirectly with one or more elements of the diaper 20. For example, the immobilization element 154 may be an unjoined layer of material disposed under the storage element 152 or may include all or a portion of the storage element 152 which is able to immobilize and retain viscous bodily waste, as described above. In any case, it is preferred that the immobilization element 154 be operatively associated with the storage element 152 and the acceptance element 150. This is necessary to ensure that viscous bodily waste accepted and/or stored by the article passes into or comes in contact with the immobilization element 154. Accordingly, it may be desirable to locate the immobilization element 154 below the storage element 152 and the acceptance element 150, in at least a portion of the crotch region 37 of the article. However, as noted above if the storage element 152 has transportation capabilities, the immobilization element 154 may be located anywhere in the diaper 20 such that the viscous fluid bodily waste accepted and/or stored can be transported to the immobilization element 154. Further, as with the acceptance and storage elements 150 and 152, the diaper 20 may have uniform or nonuniform immobilization capability. Thus, one or more immobilization elements 154 may incorporated in the article having regions of different immobilization and/or retention performance. Further, any or all of the immobilization element 154 may be removable from the absorbent article for separate disposal, if desirable.

Suitable materials for use in the immobilization element 154 include microporous foams, superabsorbent polymer particles or fibers, cellulosic fibers, capillary channel fibers, entangled synthetic fiber batts and the like. Some preferred materials include foam absorbent materials such as those described in U.S. Pat. Nos. 5,260,345; 5,387,207; and 5,625,222. Other preferred materials include absorbent gelling materials such as those described in U.S. Pat. No. 5,147,345 entitled "High Efficiency Absorbent Articles For Incontinence Management" issued to Young et al. on Sep. 15, 1992. Each of these patents is hereby incorporated by reference herein.

The FMA may be associated with the immobilization element 154. In these embodiments, the modifying agent may act to enhance the efficacy and efficiency of the immobilization element 154 by facilitating the removal of water from the feces, and thereby increasing the speed of the immobilization process and/or reducing the final mobility of the remaining solid fraction of feces. The FMA may alternatively serve to increase the viscosity of the feces within the immobilization via a direct thickening mechanism. The FMA may be loosely associated with the immobilization element or may be releasably affixed (i.e., such that feces water may effect its release) to the immobilization element 154.

Preferred Embodiments

As noted above, the present invention is applicable to many types of absorbent articles such as diapers, training pants, incontinence briefs, incontinence undergarments or pads, absorbent inserts, diaper holders and liners, feminine hygiene garments, wipes, disposable mops, bandages and the like and separate articles attached to a wearer over the perianal region. Thus, the following examples of preferred embodiments of the present invention should not construed to limit the scope of the invention.

One preferred embodiment of the present invention is the absorbent article 20 illustrated in FIG. 18. The absorbent article 20 has a first waist region 36, a second waist region 38 and a crotch region 37 located between the first waist region 36 and the second waist region 38. The diaper 20 includes a topsheet 24, a backsheet 26 and an absorbent core 28 disposed between the topsheet 24 and the backsheet 26. The topsheet 24 is disposed in at least a portion of the first waist region 36 adjacent the body facing surface 47 of the core 28 The diaper 20 also includes an acceptance element 150 joined with the topsheet 24 and extending longitudinally away from the topsheet 24 through at least a portion of the crotch region 37 and at least a portion of the second waist region 38. The acceptance element 150 includes a woven netting available as a Tub Toy Bag from Dollar Tree Dist., of Norfolk, Va.

The diaper 20 preferably further includes a storage element 152 located between the acceptance element 150 and the backsheet 26. The storage element 152 is located in at least a portion of the crotch region 37 and at least a portion of the second waist region 38. In this embodiment, the storage element 152 includes a macro-particulate structure 170 comprising particles 172. Specifically, the macro-particulate structure 170 includes about two grams of the scrubber particles mixed with about 0.35 grams of strips of foam absorbent material having a basis weight of 45 grams per square meter, as described in U.S. Pat. No. 5,260,345. (The scrubber particles can be made by cutting the abrasive nonwoven highloft side of a scrubbing pad (e.g., available as Light Duty Scrubbers #00065 from the Libman Company of Arcola, Ill.) into particles of about 8 mm×about 7 mm×about 5 mm.) The strips have dimensions of about 19 millimeters in length, 6.4 millimeters in width, and 2 millimeters in thickness. The scrubber particles are distributed over a 2.5 inch×6.4 inch (16 square inch) area disposed along the longitudinal axis of the article of approximately 0.8 mm thick "thin until wet" foam absorbent material (described in U.S. Pat. No. 5,387,207 which is incorporated herein by reference) having a basis weight of 126 grams per square meter. The scrubber particles are relatively homogeneously mixed with the absorbent foam strips and are free to move within the area circumscribed by the layer of "thin-until-wet" absorbent foam material. The particles and strips are preferably not bonded to the woven netting topsheet or any other layer. A FMA is preferably associated with the particulate elements of the storage layer via any of the means described herein. The acceptance element 150 is bonded to the underlying layers outside the periphery of the layer of "thin-until-wet" absorbent foam.

Figure 21:
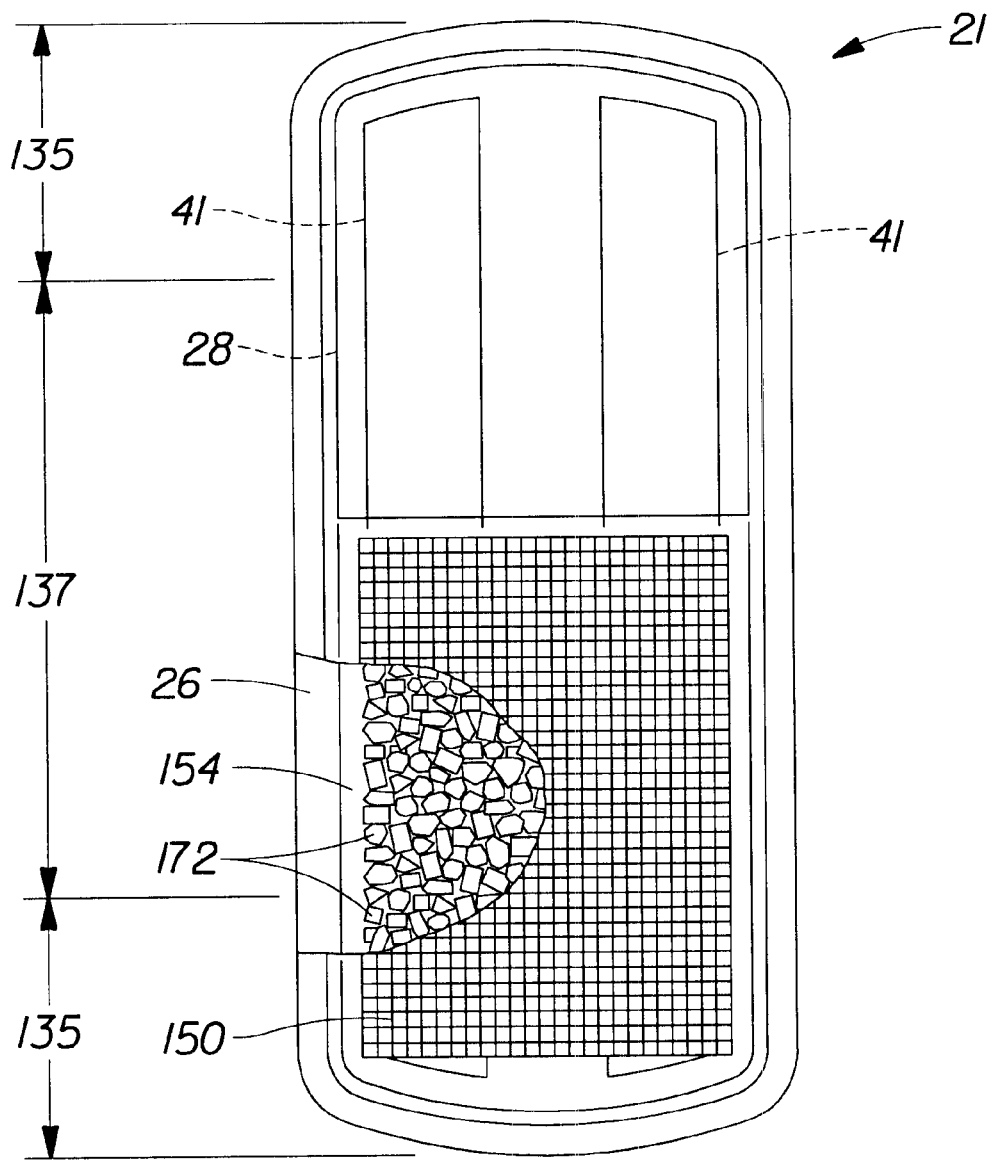
FIG. 21 is a plan view of a sanitary napkin embodiment of the present invention with portions cut away to review the underlying structure.

In another embodiment, as shown in FIG. 21, the absorbent article of the present invention may be an insert 21 or sanitary napkin which is intended to be applied separately to the wearer or to be placed in the wearer's underwear, an outer cover or the like. Thus, the insert 21 is generally not intended to take the form of a pant, but rather is to be used in conjunction with a pant or other structure which holds the insert 21 in place about the wearer. The absorbent insert 21 has a pair of opposed end regions 135 separated by a central region 137 and includes an absorbent assembly 27 which may include an absorbent core 28, an acceptance element 150, a storage element 152 and/or an immobilization element 154. The insert 21 may also include one or more attachment element(s) 41 to hold the insert 21 in place in the pant or outer cover 29 during use. The attachment element 41 may comprise adhesive, cohesive, hooks, snaps, buckles, buttons, ties, magnetic, electronic and/or any other know means for attaching absorbent articles to undergarments.

Test Methods

Viscosity

The viscosity may be determined by a controlled stress rheometer. A suitable rheometer is available from T. A. Instruments, Inc. of New Castle, Del., as model number SC$^2$100. The rheometer utilizes a stainless steel parallel plate fixture. The rheometer has a rigid horizontal first plate onto which the sample is placed and a second plate mounted over the first plate such that the axis of said second plate is perpendicular to the first plate. The second plate is 2 or 4 centimeters in diameter. A two centimeter (2 cm) parallel plate is used for firm, pasty, or highly mucousy samples, while the four centimeter (4 cm) parallel plate is used for very runny or "water-like" fecal samples. The first and second plates are spaced apart up to 2000 microns during the measurement process. The second plate is connected to a drive shaft for axial rotation. The drive motor and strain sensor are also mounted on the drive shaft.

A suitable sample (typically 2 to 3 grams) of an analog to be tested is centered on the first plate and generally centered beneath the axis of the second plate.

Prior to the test, any large pieces of undigested food material (e.g., seeds) are removed. The first plate is raised into position. Excess amounts of the sample which are displaced beyond the diameter of the second plate are removed using a spatula.

Water is then misted around the edges of the sample to prevent edge effects due to moisture loss during the measurement process. A programmed application of a shear stress, from 50 to 50,000 dynes/cm$^2$ for pasty and firm samples, is applied to the sample by the rheometer. For runny and watery samples, a shear stress range of 5 to 5000 dynes/cm$^2$ was used instead. The data is fitted to a power law function where the apparent viscosity=$kj^{(n-1)}$, k=consistency (units of cP×sec$^{(n-1)}$, j=shear rate (Units of 1/sec), and n=shear index (dimensionless). Therefore, when j=one 1/sec, the viscosity=k. (The plates are maintained at 35 degrees C. throughout the test.)

Hardness Method

Hardness is measured using a Stevens-Farnell QTS-25 Texture Analyzer, model 7113-5 kg, and associated software on an Intel-based machine having a 486 processor or higher. A ½ inch stainless steel spherical probe and an analog receptacle are provided. A suitable probe is the TA18 probe available from Leonard Farnell Co. of Hatfield, England. The analog receptacle can be made by cutting a 7 milliliter linear low density polyethylene scintillation vial (having an inside diameter of 0.55 inches+/−0.005 inches) to about 16 millimeter length. Suitable vials are available from Kimble Glass Company of Vineland, New Jersey as #58503-7 vials. The analog receptacle is filled to the top edge (level) with the analog (Analog A or B, as described below) or feces to be tested. If a modification agent is to be evaluated, the sample is prepared via the Sample Preparation Method described below. The vial is centered under the ½ inch spherical stainless steel probe. The probe is lowered such that it just contacts the surface of the analog in the vial. The probe 162 is moved downward 7 millimeters at about 100 millimeters per minute and then stopped. The Hardness is the maximum recorded resistive force encountered by the probe on its 7 millimeter stroke. (The temperature of the room and the analog should be between about 65 to 75 degrees Fahrenheit during the course of the measurement.) For reference, Hardness has been found to relate strongly to the complex modulus of the material, which is a combination of the viscous and elastic moduli of the material.

Method for Making Analog A 1.5 grams of Ultra Dawn dishwashing liquid (available from the Procter & Gamble Co, Cincinnati, Ohio) is added to an empty metal mixing bowl. 10 grams each of Feclone FPS-2 and Feclone FPS-4 are added into the bowl containing the Dawn. (Both Feclone materials are available from Siliclone Studios, Valley Forge, Pa.) Then 200 milliliters of distilled water heated to 200° F. is added to the mixing bowl. The resultant mixture is then carefully stirred by hand, to avoid introducing air bubbles to the mixture, using a rubber or plastic spatula until homogenous, (usually about 3–5 minutes). If prepared properly, the Analog A will have a Hardness between about 7 and 10 grams as measured by the above Hardness Method.

Method for Making Analog B 5 grams each of Feclone FPS-4, Feclone FPS-6, and Feclone FPS-7 are added into an empty metal mixing bowl. (Both Feclone materials are available from Siliclone Studios, Valley Forge, Pa.). Then 0.67 grams of Carbopol 941 (available from the B.F. Goodrich Corp. of Brecksville, Ohio) is added into the bowl and these four ingredients are stirred until they are homogeneously mixed using a rubber or plastic spatula to ensure adequate dispersion of the powder materials upon mixing in water. Next, 60 milliliters of water heated to 200° F. is added to the mixing bowl. The resultant mixture is mixed manually, and is stirred carefully to avoid introducing air bubbles to the mixture, using a rubber or plastic spatula until homogenous (usually about 3–5 minutes). If prepared properly, the Analog A will have a Hardness between about 600 and 650 grams.

Method for Making Analog C

Analog C is a fecal material analog made by mixing 10 grams of Carbopol 941 available from the B.F. Goodrich Corporation of Brecksville, Ohio or an equivalent acrylic polymer in 900 milliliters of distilled water. The Carpobol 941 and distilled water are weighed and measured separately. A 3-bladed marine-type propeller having a 2 inch diameter paddle, (available from VWR Scientific Products Corp. of Cincinnati, Ohio, Catalog #BR4553-64, affixed to a ⅜" stirring shaft BR4553-52), is used to stir the distilled water. The propeller speed should be constant at 450 rpm during mixing. The mixer should form a vortex without splashing. The Carbopol is slowly sieved into the water so that it is drawn into the vortex and mixed without forming white clumps, or "fish eyes". The mixture is stirred until all of the Carbopol has been added, and then for a period of 2 minutes thereafter. The sides of the bowl containing the mixture should be scraped and the bowl should be rotated as needed to achieve a homogeneous mixture. (The mixture will likely be slightly cloudy with air bubbles). One hundred grams of a 1.0 N volumetric NaOH solution, available from J. T. Baker Co., Phillipsburg, N.J., is then slowly measured into the mixture and the mixture is stirred until homogeneous. The mixture should become thick and clear. The mixture should be stirred for 2 minutes after the addition of the alkali solution. The neutralized mixture should be allowed to equilibrate for at least 12 hours and should be used for the Acceptance Under Pressure test within 96 hours thereafter. Before the Carbopol mixture is used, it should be stirred in the container at low speed (about 50 rpm) for about 1 minute to ensure the mixture is homogeneous.

Analog C should, if prepared correctly, have a "Hardness" value between 55 and 65 grams. Hardness is measured using a Stevens-Farnell QTS-25 Texture Analyzer, model 7113-5 kg, and associated software on an Intel-based machine having a 486 processor or higher. A ½ inch stainless steel spherical probe and an analog receptacle are provided. A suitable probe is the TA18 probe available from Leonard Farnell Co. of Hatfield, England. The analog receptacle can be made by cutting a 7 milliliter linear low density polyethylene scintillation vial (having an inside diameter of 0.55 inches +/−0.005 inches) to a 15 millimeter length. Suitable vials are available from Kimble Glass Company of Vineland, New Jersey as #58503-7 vials. The analog receptacle is filled to within 2 millimeters of the top edge with the analog to be tested. The vial is centered under the ½ inch spherical stainless steel probe. The probe is lowered to a distance of about 1 millimeter from the surface of the analog in the vial. The probe 162 is moved downward 7 millimeters at 100 millimeters per minute and then stopped. The Hardness is the maximum recorded resistive force encountered by the probe on its 7 millimeter stroke. (The temperature of the room and the analog should be between about 65 to 75 degrees Fahrenheit during the course of the measurement.)

Sample Preparation Method

A 250 mL Precleaned VWRbrand TraceClean jar (VWR #15900-196) is placed on a balance and tared. The desired amount of chemical agent is measured into the cup and its exact weight is recorded. After the chemical weight is recorded the balance is tared again. The desired amount of feces or fecal analog is measured into the cup containing the chemical agent. The exact amount of feces or fecal analog is recorded and the chemical agent and feces or fecal analog is stirred vigorously using the spatula end of a Standard Ayre Cervi-Scraper (VWR #15620-009) until homogeneous (total stirring time is generally about 2 minutes). For the purposes of this method, the beginning of the stirring process is defined as t=0 minutes. After the sample is mixed it is allowed to sit for the remainder of the desired reaction time. For the data presented herein, this reaction time is set at t=three minutes elapsed from the beginning of the stirring process. It is then loaded into the 16 mm receptacle described above in the Hardness Method using the spatula end of a Standard Ayre Crevi-Scraper, and the Hardness test is performed (starting at t=3 min. from the beginning of the stirring process, as described above).

Acceptance Under Pressure

Figure 22:
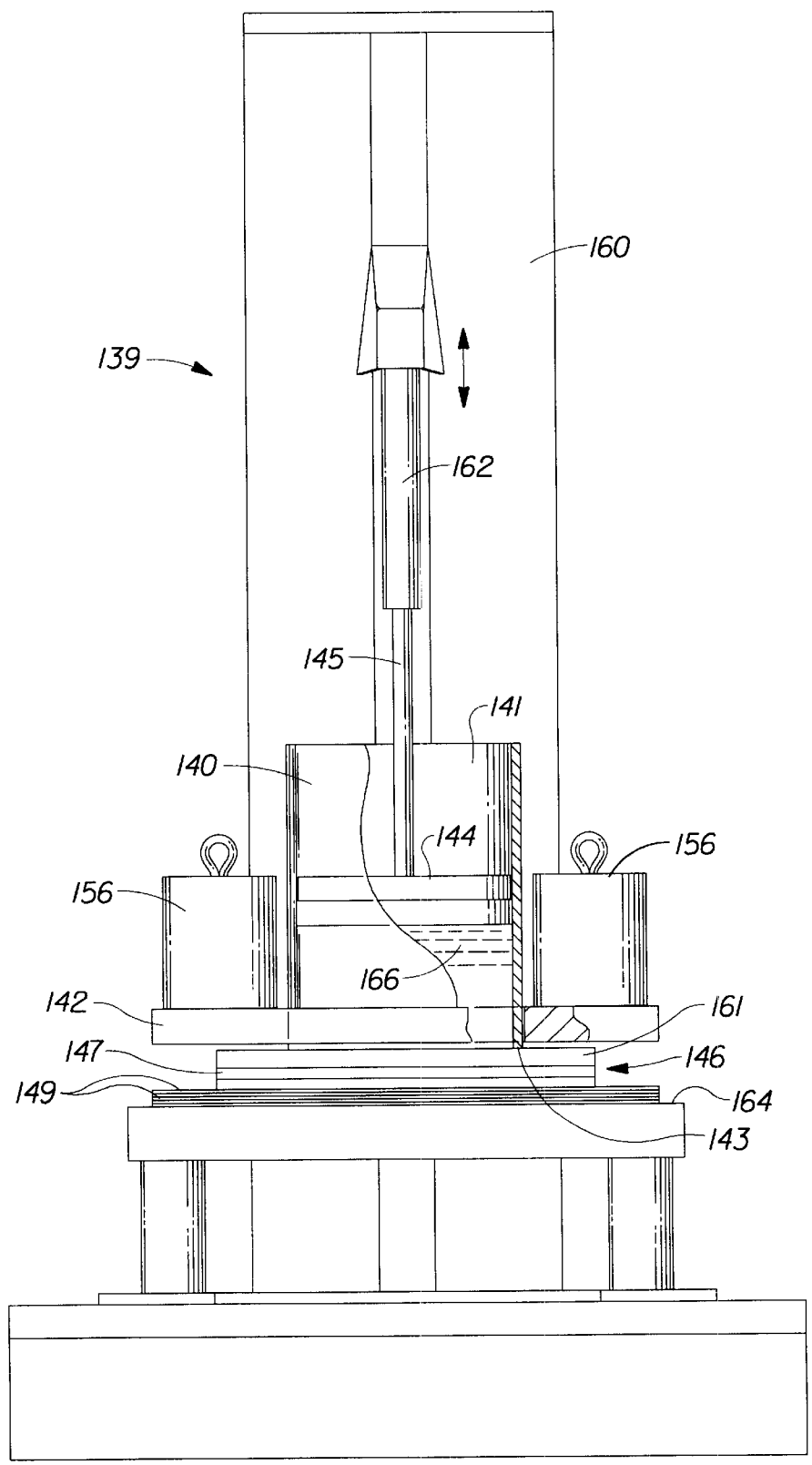
FIG. 22 is a schematic front view of an apparatus which may be used to measure Acceptance Under Pressure characteristics of certain structures.

Acceptance Under Pressure is measured by the following test which uses the apparatus 139 illustrated in FIG. 22. A hollow plexiglas cylinder 140 is provided mounted on a stainless steel plate 142 about 9.5 mm thick. The plate 142 is a square, about 10.16 cm×10.16 cm (about 4 in.×4 in.). The cylinder 140 and plate combination has a height of 7.6 centimeters (about 3.0 inches), an inside diameter of 5.08 centimeters (about 2.00 inches) and an outside diameter of 6.3 centimeters (about 2.48 inches). The bottom of the cylinder 140 extends below the plate 142 a distance of about 3.5 millimeters. The lip 143 prevents the test fluid 166 from leaking outside the designated test area. Two 625 gram weights 156 are also provided, each having a diameter of 5.08 cm (about 2.0 inches).

A cylindrically shaped 24.6 gram plexiglas weight 144 is provided. The weight 144 has a diameter of 5.08 centimeters (about 2.0 inches), so that the weight 144 fits with close tolerance within the cylinder 140 but can freely slide throughout the hole 141 in the cylinder 140. This arrangement provides a pressure of about 119 Pascals (Pa) (about 0.017 pounds per square inch) and a test area of about 20.27 square cm (about 3.142 square inches). If desired, the weight 144 may have a handle 145 to allow it to be easily inserted into and removed from the cylinder 140. In such cases, the combined mass of the handle 145 and the cylindrical weight 144 should equal 24.6 grams.

Figure 23:
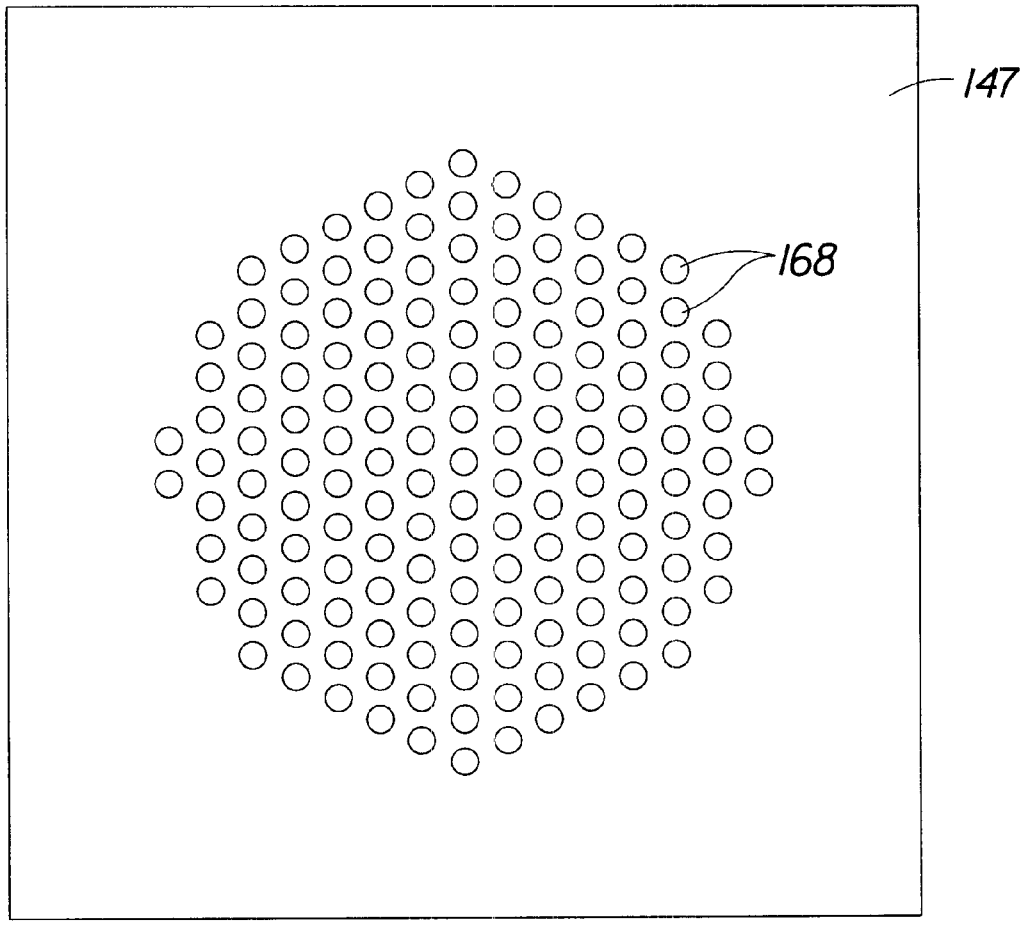
FIG. 23 is a plan view of a piece of the apparatus shown in FIG. 22.

A sample 146 of the structure to be tested for Acceptance Under Pressure properties is provided. The sample 146 may be cut from an existing diaper or may be constructed from material which has not been formed into a diaper. The sample 146 includes the entire structure intended for use in an article or the entire structure of the article to be evaluated, including the top layer 161. (In order to measure the Acceptance Under Pressure performance of discrete acceptance elements, as described in the Acceptance Element section above, the Acceptance Under Pressure test is performed using a standard storage element 147 in place of any underlying structure or layers. The standard storage element 147 used herein includes a 4 inch square 1.6 mm thick aluminum plate having a pattern of 153 regularly spaced 4.3 mm diameter holes 168, as shown in FIG. 23. The holes are arranged such that there are about 26 holes per square inch.) The sample 146 should be cut into a square measuring 10.16 centimeters by 10.16 centimeters (about 4 inches by 4 inches).

Five layers of a high basis weight blotter 149 measuring 4 inches×4 inches are provided. The top layer 161 of the sample 146 is removed and the remaining components, or layers, of the sample 146 (if there are multiple components or layers) and the five sheets of blotter material 149 are weighed to the nearest 0.01 grams. Thus, if the sample 146 is being taken from a diaper, the layers of the diaper such as topsheets, secondary topsheets, acquisition layers, absorbent cores etc., should be separated prior to weighing. (In some cases, a single layer may comprise two or more permanently bonded components.) In so doing, care must be taken not to destroy the sample 146 or cause unintended gross deformation of any parts of the sample 146. The layers of the sample 146 may be frozen to aid their separation from adjacent layers of the sample 146. Freezing may be accomplished using PH100-15 circuit refrigerant made by Philips ECG, Inc. of Waltham, Mass.

The sample 146 should be reassembled as originally configured on top of 5 stacked layers of blotter material 149 with the side of the sample 146 intended to face the wearer oriented facing up and away from the blotter material 149. The blotter material 149 is preferably filtration grade paper, available from Ahlstrom Filtration, Inc. of Mt. Holly Springs, Pa. as #632-025, having a basis weight of about 90 grams per meter.

The combined assembly of the sample 146 and the blotter material 149 is centered on the work surface 164 of a Stevens-Farnell QTS-25 Model 7111-5 kg Texture Analyzer 160 (available from Leonard Farnell Co. of Hatfield, England), under the probe 162. A suitable probe 162 is a 100 cm flat-ended cylindrical aluminum extension rod "QTSM3100" available from the Leonard Farnell Co. of Hatfield England. The cylinder 140 is centered on the sample 146. The two 625 gram weights 156 are placed on opposite corners (diagonally) of the plate 142 to stabilize it. A syringe having an opening of about 4 to 6 millimeters is used to dispense approximately 10 cubic centimeters of viscous fluid bodily waste analog 166 (Analog C as described below) through the hole 141 in the cylinder 140 onto the top of the sample 146.

Once the proper amount of feces analog 166 (Analog C) has been measured into the cylinder 140, the 24.6 gram weight 144 is inserted slowly and gently into the hole 140 in the cylinder 140 until it rests on the surface of the analog, and subsequently gently rotated one rotation clockwise followed by one rotation counter-clockwise, both rotations performed while carefully avoiding the application of any downward force on the weight. The Texture Analyzer 160 is activated so the probe 162 depresses the cylindrical weight 144 at a rate of 10 millimeters per minute until a resisting force of about 144.6 grams is reached. The Texture Analyzer 160 is set to stop the downward stroke once the resistance force of 144.6 grams is reached. The recorder is set to trigger at a resistive force of 5 grams. (The maximum resisting force of 144.6 grams corresponds to an applied pressure of 700 Pascals or 0.1 pounds per square inch). Once a resistive force of 144.6 grams is reached, the probe 162 is retracted to its starting position.

The weight 144 is removed from the cylinder 140, and then the cylinder 140 is removed from the surface of the sample 146, taking care not to drip any Analog C remaining in the cylinder 140 onto the sample. The top layer 161 of the sample 146 is then removed from the underlying layer(s) of the sample 146 by dragging the top layer 161 parallel to the surface of the underlying layers, if possible taking care not to drip any Analog C onto the blotter paper. For certain structures where the top layer 161 is difficult to remove by dragging parallel to the underlying layers, the top layer 161 may be peeled or lifted away from the underlying layers of sample 146. If the sample 146 comprises only a single layer, the standard acceptance element 151, described below, is utilized as the top layer 161 of the sample 146. The underlying layers of the sample 146 and the blotter material 149 are then weighed. The amount of test Analog C accepted by the sample 146 equals the increase in combined weight of the underlying layer(s) of the sample 146 and the blotter material 149 caused by the test Analog C penetrating through the top surface layer of the sample 146 per unit work performed (in milliJoules) on a unit area basis. The area under the force vs. distance curve, used in calculating the unit work, is calculated by integrating the force resisting the probe on its downward stroke over the total distance traveled until the maximum force of 144.6 grams is registered. The unit work is calculated using the following equation:

Unit Work (mJ)=Area under the force vs. distance curve (g/mm) $(9.81 \text{ m/s}^2)/(1000 \text{ mm/m})$ While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article adapted to receive feces from a wearer having a skin, the absorbent article comprising:
   a liquid pervious topsheet;
   a backsheet joined to at least a portion of the topsheet;
   an absorbent core disposed between at least a portion of the topsheet and the backsheet;
   a responsive system comprising at least one sensor and at least one actuator; and
   an effective amount of an available feces modifying agent;
   wherein the responsive system performs one or more functions selected from the group consisting of delivering the feces modifying agent to the feces, delivering the feces modifying agent to the skin of the wearer, and mixing the feces modifying agent with the feces.

2. The absorbent article of claim 1 wherein the feces modifying agent is a viscosity decreasing agent.

3. The absorbent article of claim 1 wherein the viscosity decreasing agent is a reducing agent.

4. The absorbent article of claim 3 wherein the reducing agent is selected from the group consisting of sulfites, thiols, thiol alcohols, mercaptoacetic acid, sodium thioglycolate, thiolactic acid, thioglycoamide, glycerol monothioglycolate, borohydrides, ternary amines, thiocyanates, thiosulfates, cyanides, thiophosphates, arsenites, phosphines, phenols, betaines, lithium aluminumhydride, aluminum chloride, guanidine hydrochloride, stannous chloride, hydroxylamine, and $LiHB(C_2H_5)_3$.

5. The absorbent article of claim 1 wherein the feces modifying agent is a feces water-liberating agent.

6. The absorbent article of claim 5 wherein the feces water liberating agent is a flocculant.

7. The absorbent article of claim 5 wherein the feces water liberating agent includes an inorganic flocculant.

8. The absorbent article of claim 7 wherein the inorganic flocculant is selected from the group including divalent and trivalent metal salts.

9. The absorbent article of claim 8 wherein the metal salts are selected from the group consisting of: iron, aluminum, calcium, and sodium salts and mixtures thereof.

10. The absorbent article of claim 8 wherein the metal salts are selected from the group consisting of ferrous chloride, ferric chloride, aluminum potassium sulfate, aluminum sulfate, sodium aluminate, ferrous sulfate, aluminum chloride hydroxide and poly aluminum silicate sulfate.

11. The absorbent article of claim 5 wherein the feces water liberating agent includes an organic flocculant.

12. The absorbent article of claim 11 wherein the organic flocculant is selected from the group consisting of: water soluble polyamides and derivatives, polyacrylics and derivatives, polyamines, and polyvinylpyrollidone.

13. The absorbent article of claim 1 wherein the feces modifying agent is a calcium-based modifying agent.

14. The absorbent article of claim 13 wherein the feces modifying agent is selected from the group consisting of: calcium oxide, calcium hydroxide, and calcium chloride.

15. The absorbent article of claim 1 wherein the feces modifying agent includes a viscosity increasing agent.

16. The absorbent article of claim 15 wherein the viscosity increasing agent includes a thickener.

17. The absorbent article of claim 16 wherein the thickener is selected from the group including: carboxymethyl cellulose, xanthan gum, polyacrylic acid and salts thereof, polyacrylamide, polyethyleneimines.

18. The absorbent article of claim 15 wherein the viscosity increasing agent includes an ionic complexing agent.

19. The absorbent article of claim 18 wherein the ionic complexing feces modifying agent is selected from the group consisting of: ZnO, MgO, MnO, CaO, calcium hydroxide, ethanolamines, quaternary ammonium salts, and $Al_2O_3$, alginates, zinc salts, aluminum salts and combinations thereof.

20. The absorbent article of claim 18 wherein the ionic complexing agent includes a crosslinking agent.

21. The absorbent article of claim 1 wherein the feces modifying agent reduces the Hardness of the feces by at least about 25% at a concentration of no more than about 0.5 weight percent.

22. The absorbent article of claim 1 wherein the feces modifying agent increases the Hardness of the feces by greater than or equal to about 100% at a concentration of no more than about 0.5 weight percent of the feces to be treated.

23. The absorbent article of claim 1 wherein the feces modifying agent is present in concentration of greater than or equal to about 0.01% by weight of the article.

24. The absorbent article of claim 1 wherein the responsive system moves a carrier structure comprising the feces modifying agent into contact with the feces.

25. The absorbent article of claim 1 wherein the actuator comprises a mechanical actuator.

26. The absorbent article of claim 1 wherein the actuator comprises:
   a pressure differentiation device having an exterior and at least one inner chamber, the pressure differentiation device maintaining the inner chamber at
   a pressure lower than an ambient pressure; and
   at least two resilient elements disposed in the inner chamber of the pressure differentiation device and held under vacuum compression.

27. The absorbent article of claim 26 further comprising a trigger mechanism capable of increasing the lower pressure of the inner chamber.

28. The absorbent article of claim 27 wherein the trigger mechanism is selected from the group of a sensor or an actuator.

29. The absorbent article of claim 26 wherein the article includes a urine loading zone into which the wearer urinates, at least a portion of the trigger mechanism being disposed at least partially in the urine loading zone.

30. The absorbent article of claim 1 wherein the sensor is selected from the group of: an electrical sensor, a mechanical sensor, a chemical sensor, a biosensor, a water soluble film, a water soluble pH sensitive film, and a closed system liquid transport member.

31. The absorbent article of claim 1 wherein the sensor comprises a vacuum-sealed bag, at least a portion of the vacuum sealed bag being water soluble.

32. The absorbent article of claim 1 wherein the responsive system performs a discontinuous response.

33. The absorbent article of claim 1, wherein the absorbent article is selected from the group of: a diaper, a training pant, a sanitary napkin, a tampon and an adult incontinence device.

34. A disposable article for receiving bodily waste comprising feces from a wearer having a skin, the disposable article including:
   a bag including an opening, means for joining the bag to the wearer, a responsive system operatively associated with at least a portion of the bag, the responsive system comprising at least one sensor and at least one actuator, and an effective amount of a feces modifying agent.

35. The disposable article of claim 34, wherein the article is selected from the group of a colostomy bag or a waste bag.

36. The disposable article of claim 34 wherein the feces modifying agent is a viscosity decreasing agent.

37. The disposable article of claim 34 wherein the feces modifying agent is a feces water-liberating agent.

38. The disposable article of claim 34 wherein the feces modifying agent is a calcium-based modifying agent.

39. The disposable article of claim 34 wherein the feces modifying agent includes a viscosity increasing agent.

40. The disposable article of claim 34 wherein the feces modifying agent reduces the Hardness of the feces by at least about 25% at a concentration of no more than about 0.5 weight percent.

41. The disposable article of claim 34 wherein the responsive system performs one or more functions selected from the group consisting of: delivering the feces modifying agent to the feces, delivering the feces modifying agent to the skin of the wearer, and mixing the feces modifying agent with the feces.

42. The disposable article of claim 41 wherein the responsive system moves a carrier structure comprising the feces modifying agent into contact with the feces.

43. The disposable article of claim 34 wherein the actuator comprises a mechanical actuator.

* * * * *

UNITED STATES PATENT AND TRADEMARK OFFICE
CERTIFICATE OF CORRECTION

PATENT NO. : 6,395,955 B1
DATED : May 28, 2002
INVENTOR(S) : Donald C. Roe et al.

It is certified that error appears in the above-identified patent and that said Letters Patent is hereby corrected as shown below:

Column 8,
Line 64, after "thereof" insert -- . -- (a period).

Column 22,
Line 16, "hag" should read -- has --.
Lines 33 and 37, after "thereof" insert -- . -- (a period).

Column 24,
Line 49, after "invention" insert -- . -- (a period).

Column 29,
Line 20, "gag" should read -- gas --.
Line 56, after "permeability" insert -- . -- (a period).

Column 31,
Lines 16, 39 and 42, after "thereof" insert -- . -- (a period).

Column 32,
Line 52, after "thereof" insert -- . -- (a period).

Column 33,
Line 12, after "material" insert -- . -- (a period).

Column 35,
Line 4, after "off" insert -- . -- (a period).

Column 42,
Line 30, "," (a comma) should be -- . -- (a period).

UNITED STATES PATENT AND TRADEMARK OFFICE
CERTIFICATE OF CORRECTION

PATENT NO. : 6,395,955 B1
DATED : May 28, 2002
INVENTOR(S) : Donald C. Roe et al.

It is certified that error appears in the above-identified patent and that said Letters Patent is hereby corrected as shown below:

<u>Column 43,</u>
Line 61, "," (a comma) should be -- . -- (a period).

Signed and Sealed this

Twenty-fifth Day of March, 2003

JAMES E. ROGAN
*Director of the United States Patent and Trademark Office*